United States Patent
Ikegami

(10) Patent No.: US 7,211,545 B2
(45) Date of Patent: May 1, 2007

(54) IMIDAZO[1,2-A]PYRIMIDINE AND FUNGICIDAL COMPOSITIONS CONTAINING THEREOF

(75) Inventor: Hiroshi Ikegami, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 451 days.

(21) Appl. No.: 10/488,273

(22) PCT Filed: Aug. 29, 2002

(86) PCT No.: PCT/JP02/08718

§ 371 (c)(1),
(2), (4) Date: Mar. 2, 2004

(87) PCT Pub. No.: WO03/022850

PCT Pub. Date: Mar. 20, 2003

(65) Prior Publication Data

US 2004/0235865 A1    Nov. 25, 2004

(30) Foreign Application Priority Data

Sep. 4, 2001  (JP)  ............................. 2001-266881

(51) Int. Cl.
  C07D 487/04    (2006.01)
  C07D 413/04    (2006.01)
  C07D 417/04    (2006.01)
  A01N 43/72     (2006.01)
  A01N 43/84     (2006.01)
  A01N 43/90     (2006.01)

(52) U.S. Cl. .................. 504/241; 544/281; 544/117; 544/61; 504/221; 504/225

(58) Field of Classification Search ............... 544/281, 544/117, 61; 514/259.1, 233.2, 228.5; 504/221, 504/225, 241
See application file for complete search history.

(56) References Cited

U.S. PATENT DOCUMENTS

| 3,923,811 A | 12/1975 | Harrington et al. |
| 5,137,131 A | 8/1992 | Enomoto |
| 5,994,360 A | 11/1999 | Pfrengle |

FOREIGN PATENT DOCUMENTS

| EP | 0 547 568 A1 | 6/1993 |
| EP | 0 550 113 A2 | 7/1993 |
| EP | 0 770 615 A1 | 5/1997 |
| JP | 2001-19693 A | 1/2001 |
| JP | 2001-043978 A | 2/2001 |
| WO | WO 98/46607 A1 | 10/1998 |
| WO | WO 02/48151 A1 | 6/2002 |

OTHER PUBLICATIONS

Translation of JP 2001 043978 A.*
M.T. Lugari et al., "High-performance liquid chromatography of phytotoxic substances", *Journal of Chromatography*, 315, (1984), pp. 384-388.
C.A. Maggiali et al., "Proprietá biologiche di imidazopirimidine", *Acta Naturalia de ((l'Ateneo Parmense))*. 18, (1982), pp. 93-101.
C.A. Maggiali et al., "Imidazopirimidine Ad Attivita Citochininica", *Farmaco—Ed. Sc.*, vol. 38, (1983), pp. 865-868.
Ganapathi R. Revankar et al., "Synthesis and Antimicrobial Activity of Certain Imidazo[1,2-a]pyrimidines", *Journal of Medicinal Chemistry*, vol. 18, No. 12, (1975), pp. 1253-1255.
Thomas Novinson et al., "Novel Heterocyclic Nitrofurfural Hydrazones. In Vivo Antitrypanosomal Activity", *Journal of Medicinal Chemistry*, vol. 19, No. 4, (1976), pp. 512-516.

* cited by examiner

*Primary Examiner*—Mark L. Berch
*Assistant Examiner*—Susanna Moore
(74) *Attorney, Agent, or Firm*—Foley & Lardner LLP

(57) ABSTRACT

The imidazo[1,2-a]pyrimidines given by the following formula [I]:

[wherein $R^1$ and $R^2$ represent a C1–C6 alkyl group optionally substituted by one or more selected from the group consisting of C1–C4 alkoxy group, C2–C8 dialkylamino group, C1–C4 alkylthio group, C2–C5 alkoxycarbonyl group, cyano group and halogen atoms; or $R^1$ and $R^2$ represent a 3–8 membered heterocyclic group together with the nitrogen atom bonded with $R^1$ and $R^2$; $R^3$ represents a halogen atom or C1–C4 alkyl group; and Ar represents a phenyl group optionally substituted by a halogen atom or atoms; and the like] have excellent activity for controlling plant diseases.

23 Claims, No Drawings

IMIDAZO[1,2-A]PYRIMIDINE AND FUNGICIDAL COMPOSITIONS CONTAINING THEREOF

TECHNICAL FIELD

The present invention relates to imidazo[1,2-a]pyrimidine and fungicidal composition containing thereof.

BACKGROUND ART

Japan unexamined patent application 2001-19693 discloses pyrazolo[1,5-a]pyrimidines given by the following formula:

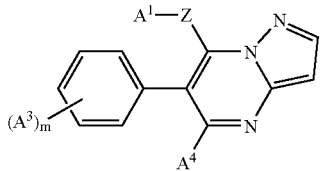

[wherein Z represents O, S, $NA^2$ or a single bond; $A^1$ represents an optionally substituted alkyl, alkenyl, alkynyl, alkadienyl, haloalkyl, aryl, heteroaryl, cycloalkyl, bicycloalkyl or heterocyclic group; $A^2$ represents a hydrogen atom or optionally substituted alkyl, alkenyl, alkynyl, alkadienyl, haloalkyl, aryl, heteroaryl, cycloalkyl, bicycloalkyl or heterocyclic group; m is 0 or an integer of 1 to 4; each of $A^3$'s represents independently a halogen atom, alkyl, alkoxy or nitro group; and $A^4$ represents a halogen atom]

It is described that said compounds have excellent fungicidal activity against many kinds of Eumycetes.

Further, with regard to imidazo[1,2-a]pyrimidines which are isomers of pyrazolo[1,5-a]pyrimidines, a kind of imidazo[1,2-a]pyrimidines having herbicidal activity or fungicidal activity are disclosed. [Acta Nat. de l'Ateneo Parmense, 18 (1982) 93, J. Med. Chem. (1975) 8, 1253, etc.] However, the imidazo[1,2-a]pyrimidines having a substituent on the 6-position are not disclosed.

The present invention was made for providing novel imidazo[1,2-a]pyrimidines having excellent activity for controlling plant diseases.

DISCLOSURE OF THE INVENTION

The present inventor has earnestly studied, found that the 6-phenylimidazo[1,2-a]pyrimidines given by the formula [I] have excellent effect for controlling plant diseases and completed the present invention.

Namely, the present invention provides the imidazo[1,2-a]pyrimidine [I] (hereinafter referred to as the present compound) given by the following formula:

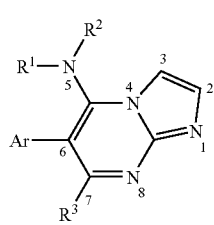

(I)

[wherein $R^1$ represents a hydrogen atom; C1–C6 alkyl group optionally substituted by one or more selected from the group consisting of C1–C4 alkoxy group, C2–C8 dialkylamino group, C1–C4 alkylthio group, C2–C5 alkoxycarbonyl group, cyano group and halogen atoms; C3–C6 alkenyl group optionally substituted by a halogen atom or atoms; C3–C6 alkynyl group optionally substituted by a halogen atom or atoms; C3–C8 cycloalkyl group optionally substituted by one or more selected from the group consisting of C1–C4 alkyl group and halogen atoms; phenyl group or phenyl C1–C2 alkyl group optionally substituted by one or more selected from the group consisting of C1–C4 alkyl group, C1–C4 alkoxy group, C1–C4 alkylthio group, C1–C3 haloalkyl group, C1–C3 haloalkoxy group, halogen atoms, nitro group, cyano group and C2–C5 alkoxycarbonyl group on the benzene ring; 5 or 6 membered heterocyclic group optionally substituted by one or more selected from the group consisting of C1–C4 alkyl group, C1–C4 alkoxy group, C1–C4 alkylthio group, C1–C3 haloalkyl group, halogen atoms, nitro group, cyano group and C2–C5 alkoxycarbonyl group; $R^2$ represents a hydrogen atom; C1–C6 alkyl group optionally substituted by one or more selected from the group consisting of C1–C4 alkoxy group, C2–C8 dialkylamino group, C1–C4 alkylthio group, C2–C5 alkoxycarbonyl group, cyano group and halogen atoms; C3–C6 alkenyl group optionally substituted by a halogen atom or atoms; C3–C6 alkynyl group optionally substituted by a halogen atom or atoms; C3–C8 cycloalkyl group optionally substituted by one or more selected from the group consisting of C1–C4 alkyl group and halogen atoms; phenyl group or phenyl C1–C2 alkyl group optionally substituted by one or more selected from the group consisting of C1–C4 alkyl group, C1–C4 alkoxy group, C1–C4 alkylthio group, C1–C3 haloalkyl group, C1–C3 haloalkoxy group, halogen atoms, nitro group, cyano group and C2–C5 alkoxycarbonyl group on the benzene ring; 5 or 6 membered heterocyclic group optionally substituted by one or more selected from the group consisting of C1–C4 alkyl group, C1–C4 alkoxy group, C1–C4 alkylthio group, C1–C3 haloalkyl group, halogen atoms, nitro group, cyano group and C2–C5 alkoxycarbonyl group; amino group optionally substituted by one or more selected from the group consisting of C1–C6 alkyl group, pheny group and benzyl group (said pheny group and benzyl group may be substituted by one or more selected from the group consisting of C1–C4 alkyl group, C1–C3 haloalkyl group and halogen atoms on the benzene ring); C1–C4 alkoxy group; phenoxy group; benzyloxy group; or $R^1$ and $R^2$ together with the nitrogen atom bonded with $R^1$ and $R^2$ represent 3–8 membered heterocyclic group (said heterocyclic group may be substituted by C1–C4 alkylene group or C2–C4 alkenylene group to represent polycyclic heterocyclyl group, and substituted by one or more selected from the group consisting of C1–C4 alkyl group, C1–C4 alkoxy group, C1–C4 alkylthio group, C1–C3 haloalkyl group, C1–C4 acyl group, halogen atoms, hydroxy group, nitro group, cyano group and C2–C5 alkoxycarbonyl group); $R^3$ represents a halogen atom or C1–C4 alkyl group; Ar represents a phenyl group optionally substituted by one or more selected from the group consisting of halogen atoms, C1–C4 alkyl group, C1–C4 alkoxy group and C1–C3 haloalkyl group], fungicidal composition containing thereof and method for controlling plant diseases by applying it to the plants.

The present invention also provides the imidazo[1,2-a] pyrimidine [II] given by the following formula:

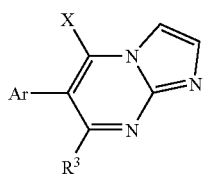

(II)

[wherein X represents a halogen atom, and Ar and $R^3$ represent as defined above], the imidazo[1,2-a]pyrimidine [III] given by the following formula:

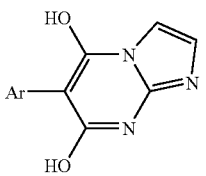

(III)

[wherein Ar represents as defined above] and

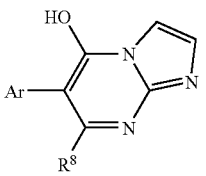

(IV)

[wherein R8 represents a C1–C4 alkyl group and Ar represents as defined above], which are useful as intermediates for producing the present compounds.

In the present invention, examples of the C1–C6 alkyl group optionally substituted by one or more selected from the group consisting of C1–C4 alkoxy group, C2–C8 dialkylamino group, C1–C4 alkylthio group, C2–C5 alkoxycarbonyl group, cyano group and halogen atoms for $R^1$ and $R^2$ include methyl group, ethyl group, propyl group, butyl group, pentyl group, hexyl group, isopropyl group, sec-butyl group, isobutyl group, t-butyl group, 1-methylbutyl group, 1-ethylpropyl group, 2-methylbutyl group, 3-methylbutyl group, 1,2-dimethylpropyl group, 1,1-dimethylpropyl group, 1,3-dimethylbutyl group, 3,3-dimethylbutyl group, 2,2-dimethylpropyl group, 2-methoxyethyl group, 3-methoxypropyl group, 2-ethoxyethyl group, 3-ethoxypropyl group, 3-butoxypropyl group, 3-isopropoxypropyl group, 2,2-dimethoxyethyl group, 2,2-diethoxyethyl group, 2-(dimethylamino)ethyl group, 2-(diethylamino)ethyl group, 2-(dipropylamino)ethyl group, 2-(dibutylamino)ethyl group, 3-(dimethylamino)propyl group, 3-(diethylamino)propyl group, 3-(dipropylamino)propyl group, 3-(dibutylamino)propyl group, 2-(methylthio)ethyl group, 2-(ethylthio)ethyl group, methoxycarbonylmethyl group, ethoxycarbonylmethyl group, t-butoxycarbonylmethyl group, 1-(methoxycarbonyl)ethyl group, 1-(ethoxycarbonyl)ethyl group, 2-(ethoxycarbonyl)ethyl group, 1-(methoxycarbonyl)-2-methyl-1-propyl group, di(ethoxycarbonyl)methyl group, cyanomethyl group, 2-cyanoethyl group, 2-fluoroethyl group, 2,2,2-trifluoroethyl group, 2-chloroethyl group, 2-bromoethyl group, 3-chloropropyl group, 3-bromopropyl group, 2,5-dichloropentyl group and 1-methyl-2,2,2-trifluoroethyl group. Examples of the C3–C6 alkenyl group optionally substituted by a halogen atom or atoms for $R^1$ and $R^2$ include 2-propenyl group, 2-methy-2-propenyl group, 2-chloro-2-propenyl group, 3-chloro-2-propenyl group and 3,3-dichloro-2-propenyl group. Examples of the C3–C6 alkynyl group optionally substituted by a halogen atom or atoms for $R^1$ and $R^2$ include 2-propynyl group and 3-chloro-2-propynyl group. Examples of the C3–C8 cycloalkyl group optionally substituted by one or more selected from the group consisting of C1–C4 alkyl group and halogen atoms for $R^1$ and $R^2$ include cyclopropyl group, cyclobutyl group, cyclopentyl group, cyclohexyl group, 2-methylcyclohexyl group, 3-methylcyclohexyl group, 4-methylcyclohexyl group, 2,3-dimethylcyclohexyl group, cycloheptyl group, cyclooctyl group and 4-chlorocyclohexyl group. Examples of the phenyl group optionally substituted by one or more selected from the group consisting of C1–C4 alkyl group, C1–C4 alkoxy group, C1–C4 alkylthio group, C1–C3 haloalkyl group, C1–C3 haloalkoxy group, halogen atoms, nitro group, cyano group and C2–C5 alkoxycarbonyl group on the benzene ring for $R^1$ and $R^2$ include phenyl group substituted by methyl group, ethyl group, propyl group, isopropyl group, t-butyl group, methoxy group, ethoxy group, propoxy group, butoxy group, sec-butoxy group, methylthio group, trifluoromethyl group, trifluoromethoxy group, 1,1,2,2-tetrafluoroethoxy group, fluorine atom, chlorine atom, bromine atom, iodine atom, nitro group, cyano group, methoxycarbonyl group, ethoxycarbonyl group, propyloxycarbonyl group, butyloxycarbonyl group and so on as well as unsubstituted phenyl group. Examples of the phenyl C1–C2 alkyl group optionally substituted by one or more selected from the group consisting of C1–C4 alkyl group, C1–C4 alkoxy group, C1–C4 alkylthio group, C1–C3 haloalkyl group, C1–C3 haloalkoxy group, halogen atoms, nitro group, cyano group and C2–C5 alkoxycarbonyl group on the benzene ring for $R^1$ and $R^2$ include benzyl group substituted by methyl group, trifluoromethyl group, fluorine atom, chlorine atom, bromine atom, iodine atom, methoxy group, ethoxy group, trifluoromethoxy group, nitro group, ethoxycarbonyl group, cyano group and so on as well as unsubstituted benzyl group, 1-phenylethyl group and 2-phenylethyl group. In the 5 or 6 membered heterocyclic group optionally substituted by one or more selected from the group consisting of C1–C4 alkyl group, C1–C4 alkoxy group, C1–C4 alkylthio group, C1–C3 haloalkyl group, halogen atoms, nitro group, cyano group and C2–C5 alkoxycarbonyl group for $R^1$ and $R^2$, examples of the 5 or 6 membered heterocyclic group include pyrrolidin-1-yl group, piperidin-1-yl group, piperidin-3-yl group, morpholin-4-yl group, piperadin-1-yl group, 2-thiazolin-2-yl group, isoxazol-5-yl group, isoxazol-3-yl group, isothiazol-5-yl group, thiazol-2-yl group, 1,3,4-thiadiazol-2-yl group, pyridin-2-yl group, pyridin-3-yl group, pyridin-4-yl group, pyrimidin-2-yl group, pyrimidin-4-yl group, pyrimidin-5-yl group, pyrazin-2-yl group and 1,2,4-triazin-3-yl group. These heterocyclic group may be substituted by one or more selected from the group consisting of C1–C4 alkyl group, C1–C4 alkoxy group, C1–C4 alkylthio group, C1–C3 haloalkyl group, halogen atoms, nitro group, cyano group and C2–C5 alkoxycarbonyl group, and examples of said substituents include methyl group, ethyl group, fluorine atom, chlorine atom, bromine atom, methoxy group, nitro group, trifluoromethyl group, methylthio group, ethylthio group, nitro group and ethoxycarbonyl group.

In the present invention, examples of the amino group optionally substituted by one or more selected from the group consisting of C1–C6 alkyl group, phenyl group and benzyl group (said phenyl group and benzyl group may be substituted by one or more selected from the group consisting of C1–C4 alkyl group, C1–C3 haloalkyl group and halogen atoms on the benzene ring) for $R^2$ include amino group, methylamino group, dimethylamino group, t-butylamino group, phenylamino group, diphenylamino group, N-phenyl-N-methylamino group, 4-methylphenylamino group, 4-chlorophenylamino group, 3-(trifluoromethyl)phenylamino group. Examples of the C1–C4 alkoxy group for $R^2$ include methoxy group, ethoxy group and t-butoxy group.

In the present invention, examples of the 3–8 membered heterocyclic group represented by $R^1$ and $R^2$ together with the nitrogen atom bonded with $R^1$ and $R^2$ include 3–8 membered heterocyclic groups containing only one nitrogen atom as a hetero atom such as aziridin-1-yl group, azetidin-1-yl, pyrrolidin-1-yl group, 3-pyrrolin-1-yl group, pyrrol-1-yl group, piperidin-1-yl group, 1,2,3,6-tetrahydropyridin-1-yl group, hexamethyleneimin-1-yl group, heptamethyleneimin-1-yl group and so on; 3–8 membered heterocyclic groups containing two or more nitrogen atoms as hetero atoms such as 2-imidazolin-1-yl group, pyrazol-1-yl group, imidazol-1-yl group, 1,2,3-triazol-1-yl group, piperazin-1-yl group, 1,4,5,6-tetrahydropyrimidin-1-yl group, 1,2,4-triazol-1-yl group, tetrazol-1-yl group and so on; and 3–8 membered heterocyclic groups containing one nitrogen atom and one or more other hetero atoms as hetero atoms such as morpholin-4-yl group, thiazolidin-3-yl group, thiomorpholin-4-yl group and so on. Said heterocyclic groups may be substituted by C1–C4 alkylene group (methylene group, ethylene group, trimethylene group, tetramethylene group) or C2–C4 alkenylene group (vinylene group, propenylene group, 2-butenylene group, 1,3-butadienylene group) and examples of the polycyclic hetrocyclyl group formed of the 3–8 membered heterocyclic group substituted by said C1–C4 alkylene group or C2–C4 alkenylene group include 2-azabicyclo[2.2.1]heptan-2-yl group, 7-azabicyclo[2.2.1]heptan-7-yl group, 2-azabicyclo[2.2.2]octan-2-yl group, 3-azabicyclo[3.2.1]octan-3-yl group, 2-azabicyclo[3.2.1]octan-2-yl group, 6-azabicyclo[3.2.1]octan-6-yl group, 8-azabicyclo[3.2.1]octan-8-yl group, 3-azabicyclo[3.2.2]nonan-3-yl group, 6-azabicyclo[3.2.2]nonan-6-yl group, 2-azabicyclo[3.3.0]octan-2-yl group, 3-azabicyclo[3.3.0]octan-3-yl group, 2-azabicyclo[4.3.0]nonan-2-yl group, 3-azabicyclo[4.3.0]nonan-3-yl group, 7-azabicyclo[4.3.0]nonan-7-yl group, 8-azabicyclo[4.3.0]nonan-8-yl group, 2-azabicyclo[4.4.0]decan-2-yl group, 3-azabicyclo[4.4.0]decan-3-yl group, indolin-1-yl group, 1,2,3,4-tetrahydroquinolin-1-yl group, 1,2,3,4-tetrahydroisoquinolin-2-yl group, indol-1-yl group, indazol-1-yl group and benzimidazol-1-yl group. These heterocyclic group may be further substituted by one or more selected from the group consisting of C1–C4 alkyl group (e.g. methyl group, ethyl group, propyl group, isopropyl group), C1–C4 alkoxy group (e.g. methoxy group), C1–C4 alkylthio group (e.g. methylthio group), C1–C3 haloalkyl group (e.g. trifluoromethyl group), C1–C4 acyl group (e.g. formyl group, acetyl group), halogen atoms (e.g. chlorine atom, bromine atom, iodine atom), hydroxy group, nitro group, cyano group and C2–C5 alkoxycarbonyl group (e.g. methoxycarbonyl group, ethoxycarbonyl group, propyloxycarbonyl group, t-butoxycarbonyl group).

Preferable embodiments for $R^1R^2N$ in the present compounds are ones wherein $R^1$ and $R^2$ independently represent a hydrogen atom; C1–C6 alkyl group optionally substituted by one or more selected from the group consisting of C1–C4 alkoxy group, C2–C8 dialkylamino group, C1–C4 alkylthio group, C2–C5 alkoxycarbonyl group, cyano group and halogen atoms; C3–C6 alkenyl group optionally substituted by a halogen atom or atoms; C3–C6 alkynyl group optionally substituted by a halogen atom or atoms; C3–C8 cycloalkyl group optionally substituted by one or more selected from the group consisting of C1–C4 alkyl group and halogen atom; or wherein $R^1$ and $R^2$ together with the nitrogen atom bonded with $R^1$ and $R^2$ represent 3–8 membered heterocyclic group optionally substituted by C1–C4 alkylene group or C2–C4 alkenylene group, or optionally substituted by one or more selected from the group consisting of C1–C4 alkyl group, C1–C4 alkoxy group, C1–C4 alkylthio group, trifluoromethyl group, C1–C4 acyl group, halogen atoms, hydroxy group, nitro group, cyano group and C2–C5 alkoxycarbonyl group. More preferable embodiments are ones wherein $R^1$ and $R^2$ independently represent C1–C6 alkyl group optionally substituted by a halogen atom or atoms; C3–C6 alkenyl group optionally substituted by a halogen atom or atoms; C3–C6 alkynyl group optionally substituted by a halogen atom or atoms; C3–C8 cycloalkyl group optionally substituted by one or more selected from the group consisting of C1–C4 alkyl group and halogen atoms; wherein $R^1$ and $R^2$ together with the nitrogen atom bonded with $R^1$ and $R^2$ represent pyrrolidin-1-yl group, 3-pyrrolin-1-yl group, piperidin-1-yl group, 1,2,3,6-tetrahydropyridin-1-yl group, hexamethyleneimin-1-yl group, piperazin-1-yl group, morpholin-4-yl group and thiomorpholin-4-yl group optionally substituted by a C1–C4 alkyl group or groups.

In the present invention, examples of the halogen atom for $R^3$ include fluorine atom, chlorine atom, bromine atom and iodine atom. Examples of the C1–C4 alkyl group for $R^3$ include methyl group, ethyl group, propyl group, isopropyl group and t-butyl group.

Preferable embodiments for $R^3$ in the present compounds are a chlorine atom or methyl group.

In the present invention, examples of the phenyl group optionally substituted by one or more selected from the group consisting of C1–C4 alkyl group, C1–C4 alkoxy group and C1–C3 haloalkyl group for Ar include phenyl groups substituted by fluorine atom, chlorine atom, bromine atom, iodine atom, methyl group, ethyl group, propyl group, isopropyl group, t-butyl group, methoxy group, ethoxy group, propyloxy group, isopropyloxy group, t-butyloxy group, trifluoromethyl group and so on as well as unsabstituted phenyl group Preferable embodiments for Ar in the present compounds are phenyl groups substituted by a halogen atom or atoms at one or more of 2-, 4- and 6-positions, and more preferable embodiments are phenyl groups substituted by fluorine atoms or chlorine atoms at two or more of 2-, 4- and 6-positions and unsubstituted at 3- and 5-positions. Typical examples are 2-chlorophenyl group, 2-fluorophenyl group, 2,6-dichlorophenyl group, 2,6-difluorophenyl group, 2,4-dichlorophenyl group, 2,4-difluorophenyl group, 2-chloro-6-fluorophenyl group, 2,4,6-trifluorophenyl group, 4-chloro-2,6-difluorophenyl group, 2-chloro-4,6-difluorophenyl group, 2,6-dichloro-4-fluorophenyl group, 2,4-dichloro-6-fluorophenyl group and 2,4,6-trichlorophenyl group.

The present compounds may have asymmetric carbon atom(s) and double bond(s), and the scope of the present invention include mixtures at any ratio of the optical isomers ((+)-form, (−)-form) and geometrical isomers and each of the pure isomers. Further, the salts of the present compounds are also within the scope of the present invention.

Examples of the present compounds having excellent effect for controlling plant diseases include 5-(piperidin-1-yl)-6-(2,4,6-trifluorophenyl)-7-chloroimidazo[1,2-a]pyrimidine, 5-(4-methylpiperidin-1-yl) -6-(2,4,6-trifluorophenyl)-7-chloroimidazo[1,2-a]pyrimidine, 5-(2-methylpiperidin-1-yl)-6-(2,4,6-trifluorophenyl)-7-chloroimidazo[1,2-a]pyrimidine, 5-(morpholin-4-yl) -6-(2,4,6-trifluorophenyl)-7-chloroimidazo[1,2-a]pyrimidine, 5-(thiomorpholin-4-yl)-6-(2,4,6-trifluorophenyl)-7-chloroimidazo[1,2-a]pyrimidine, 5-(hexamethyleneimin-1-yl)-6-(2,4,6-trifluorophenyl)-7-chloroimidazo[1,2-a]pyrimidine, 5-(2,5-dimethylpyrrolidin-1-yl)-6-(2,4, 6-trifluorophenyl)-7-chloroimidazo[1,2-a]pyrimidine, 5-dipropylamino-6-(2,4,6-trifluorophenyl)-7-chloroimidazo[1,2-a]pyrimidine, 5-diallylamino-6-(2,4,6-trifluorophenyl)-7-chloroimidazo[1,2-a]pyrimidine, 5-(piperidin-1-yl)-6-(2,4,6-trifluorophenyl)-7-methylimidazo[1,2-a]pyrimidine, 5-(4-methylpiperidin-1-yl)-6-(2,4,6-trifluorophenyl)-7-methylimidazo[1,2-a]pyrimidine, 5-(2-methylpiperidin-1-yl)-6-(2,4,6-trifluorophenyl)-7-methylimidazo[1,2-a]pyrimidine, 5-(morpholin-4-yl)-6-(2,4,6-trifluorophenyl)-7-methylimidazo[1,2-a]pyrimidine, 5-(thiomorpholin-4-yl)-6-(2,4,6-trifluorophenyl)-7-methylimidazo[1,2-a]pyrimidine, 5-(hexamethyleneimin-1-yl)-6-(2,4,6-trifluorophenyl)-7-methylimidazo[1,2-a]pyrimidine, 5-(2,5-dimethylpyrrolidin-1-yl)-6-(2,4,6-trifluorophenyl)-7-methylimidazo[1,2-a]pyrimidine, 5-dipropylamino-6-(2,4, 6-trifluorophenyl)-7-methylimidazo[1,2-a]pyrimidine, 5-diallylamino-6-(2,4,6-trifluorophenyl)-7-methylimidazo[1,2-a]pyrimidine, 5-(piperidin-1-yl)-6-(2-chloro-6-fluorophenyl)-7-chloroimidazo[1,2-a]pyrimidine, 5-(4-methylpiperidin-1-yl)-6-(2-chloro-6-fluorophenyl)-7-chloroimidazo [1,2-a]pyrimidine, 5-(2-methylpiperidin-1-yl)-6-(2-chloro-6-fluorophenyl)-7-chloroimidazo[1,2-a]pyrimidine, 5-(morpholin-4-yl)-6-(2-chloro-6-fluorophenyl)-7-chloroimidazo[1,2-a]pyrimidine, 5-(thiomorpholin-4-yl)-6-(2-chloro-6-fluorophenyl)-7-chloroimidazo[1,2-a]pyrimidine, 5-(hexamethyleneimin-1-yl)-6-(2-chloro-6-fluorophenyl)-7-chloroimidazo[1,2-a]pyrimidine, 5-(2,5-dimethylpyrrolidin-1-yl)-6-(2-chloro-6-fluorophenyl)-7-chloroimidazo[1,2-a]pyrimidine, 5-dipropylamino-6-(2-chloro-6-fluorophenyl)-7-chloroimidazo[1,2-a]pyrimidine, 5-diallylamino-6-(2-chloro-6-fluorophenyl)-7-chloroimidazo[1,2-a]pyrimidine, 5-(piperidin-1-yl)-6-(2-chloro-6-fluorophenyl)-7-methylimidazo[1,2-a]pyrimidine, 5-(4-methylpiperidin-1-yl)-6-(2-chloro-6-fluorophenyl)-7-methylimidazo [1,2-a]pyrimidine, 5-(2-methylpiperidin-1-yl)-6-(2-chloro-6-fluorophenyl)-7-methylimidazo[1,2-a]pyrimidine, 5-(morpholin-4-yl)-6-(2-chloro-6-fluorophenyl)-7-methylimidazo[1,2-a]pyrimidine, 5-(thiomorpholin-4-yl)-6-(2-chloro-6-fluorophenyl)-7-methylimidazo[1,2-a]pyrimidine, 5-(hexamethyleneimin-1-yl)-6-(2-chloro-6-fluorophenyl)-7-methylimidazo[1,2-a]pyrimidine, 5-(2,5-dimethylpyrrolidin-1-yl)-6-(2-chloro-6-fluorophenyl)-7-methylimidazo[1,2-a]pyrimidine, 5-dipropylamino-6-(2-chloro-6-fluorophenyl)-7-methylimidazo [1,2-a]pyrimidine, 5-diallyamino-6-(2-chloro-6-fluorophenyl)-7-methylimidazo[1,2-a]pyrimidine, 5-(piperidin-1-yl)-6-(2,6-difluorophenyl)-7-chloroimidazo[1,2-a]pyrimidine, 5-(4-methylpiperidin-1-yl)-6-(2,6-difluorophenyl)-7-chloroimidazo[1,2-a]pyrimidine, 5-(2-methylpiperidin-1-yl)-6-(2,6-difluorophenyl)-7-chloroimidazo[1,2-a]pyrimidine, 5-(morpholin-4-yl)-6-(2,6-difluorophenyl)-7-chloroimidazo[1,2-a]pyrimidine, 5-(thiomorpholin-4-yl)-6-(2,6-difluorophenyl)-7-chloroimidazo[1,2-a]pyrimidine, 5-(hexamethyleneimin-1-yl)-6-(2,6-difluorophenyl)-7-chloroimidazo[1,2-a]pyrimidine, 5-(2,5-dimethylpyrrolidin-1-yl)-6-(2,6-difluorophenyl)-7-chloroimidazo[1,2-a]pyrimidine, 5-dipropylamino-6-(2,6-difluorophenyl)-7-chloroimidazo[1,2-a]pyrimidine, 5-diallylamino-6-(2,6-difluorophenyl)-7-chloroimidazo[1, 2-a]pyrimidine, 5-(piperidin-1-yl)-6-(2,6-difluorophenyl)-7-methylimidazo[1,2-a]pyrimidine, 5-(4-methylpiperidin-1-yl)-6-(2,6-difluorophenyl)-7-methylimidazo[1,2-a]pyrimidine, 5-(2-methylpiperidin-1-yl)-6-(2,6-difluorophenyl)-7-methylimidazo[1,2-a]pyrimidine, 5-(morpholin-4-yl)-6-(2,6-difluorophenyl)-7-methylimidazo[1,2-a]pyrimidine, 5-(thiomorpholin-4-yl)-6-(2,6-difluorophenyl)-7-methylimidazo[1,2-a]pyrimidine, 5-(hexamethyleneimin-1-yl)-6-(2,6-difluorophenyl)-7-methylimidazo[1,2-a]pyrimidine, 5-(2,5-dimethylpyrrolidin-1-yl)-6-(2,6-difluorophenyl)-7-methylimidazo[1,2-a]pyrimidine, 5-dipropylamino-6-(2,6-difluorophenyl)-7-methylimidazo[1,2-a]pyrimidine and 5-diallylamino-6-(2,6-difluorophenyl)-7-methylimidazo[1, 2-a]pyrimidine.

The present compound can be produced by making the imidazo[1,2-a]pyrimidine [II] react with an amine [V] of the following formula:

[wherein $R^1$ and $R^2$ have the same meanings as defined above].

The theoretical amount of the amine [V] is one mole based on one mole of the imidazo[1,2-a]pyrimidine [II], but the used amount can be varied according to the reaction condition.

The reaction can be performed without solvent or in an inert solvent. Examples of the solvent used for the reaction include ethers such as dioxane, diethyl ether, tetrahydrofuran, methyl t-butyl ether and so on; halogenated hydrocarbons such as dichloromethane, chloroform, carbon tetrachloride, 1,2-dichloroethane, chlorobenzene and so on; hydrocarbons such as toluene, benzene, xylene and so on; aprotic polar solvents such as N,N-dimethylformamide, dimethyl sulfoxide and so on; alcohols such as methanol, ethanol, isopropyl alcohol and so on.

The reaction can be performed in the presence of a base. One mole or more of the base is usually used based on one mole of the imidazo[1,2-a]pyrimidine [II]. Examples of the base used for the reaction include organic bases such as pyridine, 2,6-lutidine, triethylamine, N,N-diisopropylethylamine, diazabicycloundecene (DBU), diazabicyclononene (DBN) and so on; and inorganic bases such as potassium carbonate, sodium hydride and so on. It may be possible to give the same effect as one by using said base when an excessive amount of the amine [V] is used.

The reaction temperature is usually in the range of 0° C. to 200° C. It is selected dependently on the reaction rate from the above range. The reaction can be performed at a higher temperature than the boiling point of the amine [V] or the solvent by using an autoclave as a reaction container.

The termination of the reaction can be identified by analyzing the residual amount of the imidazo[1,2-a]pyrimidine [II] with a method of thin-layer chromatography, high pressure liquid chromatography or the like.

After the reaction, usual work-up procedures, for example pouring the reaction liquid into water, extracting with organic solvent and concentration, give the present compound. Further, the present compound can be purified by recrystallization, chromatography and so on.

The amine [V] is a known compound, or can be prepared according to known methods from known compounds.

The imidazo[1,2-a]pyrimidine [II] can be prepared by the following scheme.

(Production Route a)

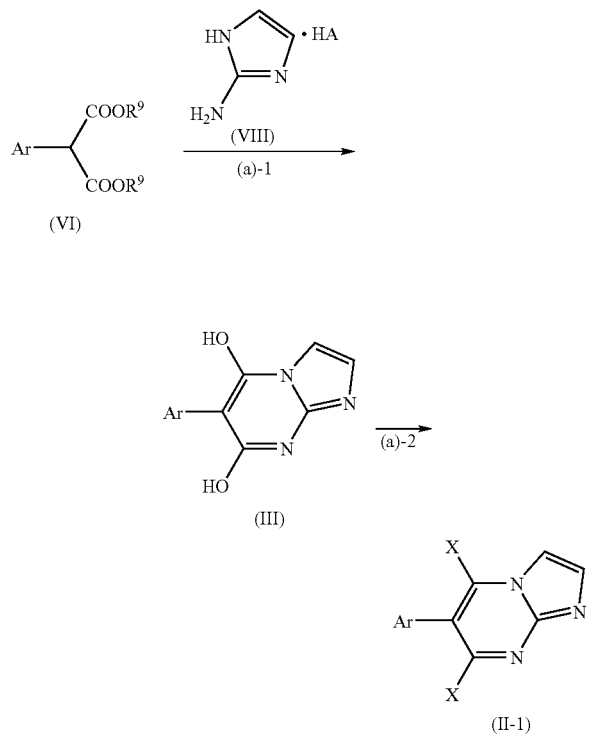

[wherein $R^9$ represents a methyl group or ethyl group; HA represents a mineral acid (e.g. hydrochloric acid, sulfuric acid); Ar and X have the same meanings described above]

(Production Route b)

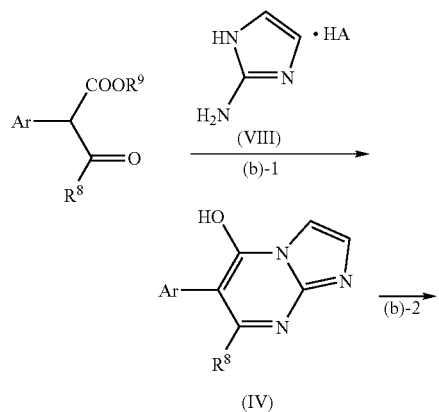

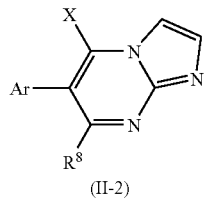

[wherein $R^8$ represents a C1–C4 alkyl group; $R^9$, HA, Ar and X have the same meanings described above]

The diester compound [VI] that is a starting material of Production route (a) is a known compound (described in JP hei2-202876A, Chemistry Letters, 1981, p. 367 and so on) or can be prepared according to a known method. The β-ketoester [VII] that is a starting material of Production route (b) is known in Organic Synthesis Collective Volume 2, pp. 487–489 and pp. 284–286, JP sho60-255788A and so on, or can be prepared according to a known method.

The 2-aminoimidazole mineral acid salt [VIII] that is a common starting material to Production routes (a) and (b) is known in J. Chem. Soc., 1956, 307, J. Org. Chem., 1964, 3118 and so on.

Step (a)-1

The imidazo[1,2-a]pyrimidine [III] can be prepared by making the diester [VI] react with the 2-aminoimidazole mineral acid salt [VIII].

The theoretical amount is one mole of the 2-aminoimidazole mineral acid salt [VIII] based on one mole of the diester [VI], but the amount can be varied according to the reaction condition. The reaction is carried out in the presence of a base without solvent or in a inert solvent at 50° C. to 200° C. Examples of the base include organic bases such as tri-n-butylamine, diazabicycloundecene (DBU), diazabicyclononene (DBN) and so on. The amount of the base used for the reaction is one mole or more based on one mole of the total of the diester [VI] and the 2-aminoimidazole mineral acid salt [VIII]. Examples of the solvent used for the reaction include hydrocarbons such as mesitylene and so on, and aprotic polar solvents such as N,N-dimethylformamide (DMF) and so on.

The termination of the reaction can be identified by analysing the residual amount of the diester [VI] by a method of thin layer chromatography, high pressure liquid chromatography or the like.

After the reaction, for example, a hydrophobic organic solvent and water are added to the reaction mixture, the separated water layer is optionally concentrated, treated with an acid such as hydrochloric acid and the precipitate is filtered to give the imidazo[1,2-a]pyrimidine [III]. Alternatively, the reaction mixture is optionally concentrated and then filtered to give a salt of the imidazo[1,2-a]pyrimidine [III]. The obtained imidazo[1,2-a]pyrimidine [III] can be further purified by recrystallization or the like.

Step (a)-2

The imidazo[1,2-a]pyrimidine [II-1], which is an imidazo[1,2-a]pyrimidine [II] wherein $R^3$ is a halogen atom, can be prepared by making the imidazo[1,2-a]pyrimidine [III] or its salt react with a halogenating agent.

Examples of the halogenating agent used for the reaction include phosphorus oxychloride and phosphorus oxybromide.

The reaction is carried out without solvent or in an inert solvent (e.g. hydrocarbons such as toluene, nitrites such as acetonitrile, halogenated hydrocarbons such as ethylene dichloride) at 80° C. to 150° C. The reaction may be accelerated by the presence of a base, and examples of the base include organic bases such as N,N-diethylaniline, N,N-dimethylaniline, triethylamine, N,N-diisopropylethylamine, pyridine, 5-ethyl-2-picoline, DBU and DBN.

The termination of the reaction can be identified by analysing the residual amount of the imidazo[1,2-a]pyrimidine [III] by a method of thin layer chromatography, high pressure liquid chromatography or the like.

After the reaction, usual work-up procedures such as removing an excess of the halogenating agent, pouring the residue into water, extracting it with an organic solvent and concentrating it to give the imidazo[1,2-a]pyrimidine [II-1]. The obtained imidazo[1,2-a]pyrimidine [II-1] can be further purified by recrystallization, chromatography or the like.

Step (b)-1

The imidazo[1,2-a]pyrimidine [IV] can be prepared by making the β-ketoester [VII] react with the 2-aminoimidazole mineral acid salt [VIII].

The theoretical amount is one mole of the 2-aminoimidazole mineral acid salt [VIII] based on one mole of the 6-ketoester [VII], but the amount can be varied according to the reaction condition. The reaction is carried out in the presence of a base, without solvent or in an inert solvent at the temperature of 50° C. to 200° C. Examples of the base include organic bases such as tri-n-butylamine, diazabicycloundecene (DBU), diazabicyclononene (DBN) and so on. The amount of the base used for the reaction is one mole or more base on one mole of the total of the 8-ketoester [VII] and the 2-aminoimidazole mineral acid salt [VIII]. Examples of the solvent used for the reaction include hydrocarbons such as mesitylene and so on, and aprotic polar solvents such as N,N-dimethylformamide and so on.

The termination of the reaction can be identified by analysing the residual amount of the β-ketoester [VII] by a method of thin layer chromatography, high pressure liquid chromatography or the like.

After the reaction, for example, a hydrophobic organic solvent and water are added to the reaction mixture, the separated water layer is optionally concentrated and treated with an acid such as hydrochloric acid to give a precipitate of the imidazo[1,2-a]pyrimidine [IV]. Alternatively, the reaction mixture is optionally concentrated and then filtered to give a salt of the imidazo[1,2-a]pyrimidine [IV] The obtained imidazo[1,2-a]pyrimidine [IV] can be further purified by recrystallization or the like.

Step (b)-2

The imidazo[1,2-a]pyrimidine [II-2], which is an imidazo [1,2-a]pyrimidine [II] wherein $R^3$ is a C1–C4 alkyl group, can be prepared by making the imidazo[1,2-a]pyrimidine [IV] or its salt react with a halogenating agent.

Examples of the halogenating agent used for the reaction include phosphorus oxychloride and phosphorus oxybromide.

The reaction is carried out without solvent or in a inert solvent (e.g. hydrocarbons such as toluene, nitrites such as acetonitrile, halogenated hydrocarbons such as ethylene dichloride) at 80° C. to 150° C. The reaction may be accelerated by the presence of a base, and examples of the base include organic bases such as N,N-diethylaniline, N,N-dimethylaniline, triethylamine, N,N-diisopropylethylamine, pyridine, 5-ethyl-2-picoline, DBU and DBN.

The termination of the reaction can be identified by analysing the residual amount of the imidazo[1,2-a]pyrimidine [IV] by a method of thin layer chromatography, high pressure liquid chromatography or the like.

After the reaction, usual work-up procedures such as removing an excess of halogenating agent, pouring the residue into water, extracting it with an organic solvent and concentrating it to give the imidazo[1,2-a]pyrimidine [II-2]. The obtained imidazo[1,2-a]pyrimidine [II-2] can be further purified by recrystallization, chromatography or the like.

When the present compound is used as an active ingredient of a fungicide, it may be used without other ingredients; however, it is usually formulated by mixing a solid carrier, liquid carrier, surfactant, or the other formulation auxiliary to emulsifiable concentrates, wettable powders, water dispersible granules, emulsion formulations, flowables, dusts, granules and so on. These formulations usually contain 0.1 to 90% by weight of the present compound as an active ingredient.

Examples of the solid carrier include minerals such as kaolin clay, attapulgite clay, bentonite, montmorillonite, terra alba, pyrophillite, talc, diatomaceous earth, calcite and so on; natural organisms such as corncob powder, walnut shell powder and so on; synthetic organisms such as urea and so on; and salts such as calcium carbonate, ammonium sulfate and so on. Examples of the liquid carrier include aromatic hydrocarbons such as xylene, alkylbenzene, methylnaphthalene and so on; alcohols such as isopropanol, ethylene glycol, propylene glycol, cellosolve and so on; ketones such as acetone, cyclohexanone, isophorone and so on; vegetable oils such as soybean oil, cotton seed oil and so on; petroleum aliphatic hydrocarbons; esters; dimethyl sulfoxide; acetonitrile; and water.

Examples of the surfactant include anionic surfactants such as alkylsulfate ester salts, alkylarylsulfonic acid salts, dialkylsulfosuccinic acid salts, polyoxyethylene alkyl aryl ether phosphate ester salts, ligninsulfonic acid salts, naphthalenesulfonate formaldehyde condensate and so on; and nonionic surfactants such as polyoxyethylene alkyl aryl ether, polyoxyethylene alkyl polyoxypropylene block copolymer, sorbitan fatty acid ester and so on.

Examples of the formulation auxiliary include water soluble polymers such as polyvinyl alcohol, polyvinylpyrrolidone and so on; gum arabic; alginic acid and its salts; polysaccharides such as CMC (carboxymethylcellulose) and xanthan gum; inorganic materials such as aluminum magnesium silicate and alumina sol; preservatives; coloring agents; and stabilizers such as PAP (isopropyl acid phosphate) and BHT.

When the present compound is used for controlling plant diseases, it typically applied by the methods of foliar treatment, soil treatment and so on. The application dosage can be varied according to the type of the protected plant, the type of the disease to be controlled, degree of affection by the disease, formulation type, application method, time of application, weather conditions and so on, and it is usually 1 to 5000 g, preferably 5 to 1000 g per one hectare. In case that emulsifiable concentrate, wettable powder, suspensible concentrate or the like is diluted with water and applied, the application concentration of the active ingredientis 0.0001 to 3% by weight, preferably 0.0005 to 1% by weight. Dusts, granules and the like are applied without dilution as they are.

Further, the present compound can be applied by the other usual methods such as seed disinfection and so on. In the case of seed treatment, seeds are usually soaked in a dilution of the present compound made 1 to 1000 ppm of the concentration, or the dilution is sprayed to or painted the seeds, alternatively, the seeds are treated with the dusts containing the present compound at 0.1 to 10% by weight.

The present compound can be used as an effective ingredient of fungicide for controlling plant diseases in upland field, paddy field, orchard, tea field, pasture, lawn and the like. It may occasionally be expected to increase the fungicidal effect by mixing with the other fungicide. Examples of the fungicide include azole fungicidal compounds such as propiconazole, triadimenol, prochloraz, penconazole, tebuconazole, flusilazole, diniconazole, bromuconazole, epoxyconazole, difenoconazole, cyproconazole, metconazole, triflumizole, tetraconazole, myclobutanil, fenbuconazole, hexaconazole, fluquinconazole, triticonazole, bitertanol, imazalil, flutriafol and so on; cyclic amine fungicidal compounds such as fenpropimorph, tridemorph, fenpropidin and so on; benzimidazole fungicidal compounds such as carbendazim, benomyl, thiabendazole, thiophanate-methyl and so on; procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlorfluanid; folpet; kresoxim-methyl; azoxystrobin; trifloxystrobin; picoxystrobin; pyraclostrobin; N-methyl-α-methoxyimino-2-[(2,5-dimethylphenoxy)methyl]phenylacetamide; spiroxamine; quinixyfen; fenhexamide; famoxadone; fenamidone; iprovalicard; benthiavalicarb; pencycuron; flutolanil; furametpyr; phthalide; carpropamid; diclocymet; probenazole; blasin; cyazofamid; nicobifen and metrafenone.

The present compound may be used together with the other agricultural or horticultural insecticide, acaricide, nematicide, herbicide, plant growth regulator and fertilizer. It may be blended in advance of the application.

Examples of the insecticide, acaricide and nematicide include organophosphorus compounds such as fenitrothion [O,O-dimethyl O-(3-methyl-4-nitrophenyl)phosphorothioate], fenthion [O,O-dimethyl O-(3-methyl-4-(methylthio) phenyl)phosphorothioate], diazinon [O,O-diethyl O-2-isopropyl-6-methylpyrimidin-4-yl phosphorothioate], chlorpyrifos [O,O-diethyl O-3,5,6-trichloro-2-pyridyl phosphorothioate], acephate [O,S-dimethyl acetylphosphoramidethioate], methidathion [S-2,3-dihydro-5-methoxy-2-oxo-1,3,4-thiadiazol-3-ylmethyl O,O-dimethyl phosphorodithioate], disulfoton [O,O-diethyl S-2-ethylthioethyl phosphorothioate], DDVP [2,2-dichlorovinyl dimethyl phosphate], sulprofos, [O-ethyl O-4-(methylthio)phenyl S-propyl phosphorodithioate], cyanophos [O-4-cyanophenyl O,O-dimethyl phosphorothioate], dioxabenzofos [2-methoxy-4H-1,3,2-benzodioxaphosphorin-2-sulfide], dimethoate [O,O-dimethyl S-(N-methylcarbamoylmethy) dithiophosphate], phenthoate [ethyl 2-dimethoxyphosphinothioylthio(phenyl)acetate], malathion [diethyl (dimethoxyphosphinothioylthio)succinate], trichlorfon [dimethyl2,2,2-trichloro-1-hydroxyethylphosphonate], azinphos-methyl [S-3,4-dihydro-4-oxo-1,2,3-benzotriazin-3-ylmethyl O,O-dimethyl phosphorodithioate], monocrotophos [dimethyl (E)-1-methyl-2-(methylcarbamoyl)vinyl phosphate], ethion [O,O,O',O'-tetraethyl S,S'-methylenebis (phosphorodithioate)], fosthiazate [N-(O-methyl-S-sec-butyl) phosphorylthiazolidin-2-one] and so on; carbamate compound such as BPMC [2-sec-butylphenyl methylcarbamate], benfuracarb [ethyl N-(2,3-dihydro-2,2-dimethylbenzofuran-7-yloxycarbonyl(methyl)aminothio)-N-isopropyl-β-alaninate, propoxur [2-isopropylphenyl N-methylcarbamate], carbosulfan [2,3-dihydro-2,2-dimethyl-7-benzo[b]furanyl N-dibutylaminothio-N-methylcarbamate], carbaryl [1-naphthyl N-methylcarbamate], methomyl [S-methyl-N-[(methylcarbamoyl)oxy] thioacetoimidate], ethiofencarb [2-(ethylthiomethyl)phenyl methylcarbamate], aldicarb [2-methyl-2-(methylthio)propionaldehyde O-methylcarbamoyloxime], oxamyl [N,N-dimethyl-2-methylcarbamoyloxyimino-2-(methylthio)acetamide], fenothiocarb [S-4-phenoxybutyl-N,N-dimethylthiocarbamate] and so on; pyrethroid compounds such as etofenprox [2-(4-ethoxyphenyl)-2-methylpropyl 3-phenoxybenzyl ether], fenvalerate [(RS)-α-cyano-3-phenoxybenzyl (RS)-2-(4-chlorophenyl)-3-methylbutyrate], esfenvalerate [(S)-α-cyano-3-phenoxybenzyl (S)-2-(4-chlorophenyl)-3-methylbutyrate], fenpropathrin [(RS)-α-cyano-3-phenoxybenzyl 2,2,3,3-tetramethylcyclopropanecarboxylate], cypermethrin [(RS)-α-cyano-3-phenoxybenzyl (1RS,3RS)-3-(2,2-dichlorovinyl)-2,2-dimethylcyclopropanecarboxylate], permethrin [3-phenoxybenzyl (1RS, 3RS)-3-(2,2-dichlorovinyl)-2,2-dimethylcyclopropanecarboxylate], cyhalothrin [(RS)-α-cyano-3-phenoxybenzyl (Z)-(1RS, 3RS)-3-(2-chloro-3,3,3-trifluoropropenyl)-2,2-dimethylcyclopropanecarboxylate], deltamethrin [(S)-α-cyano-m-phenoxybenzyl (1R,3R)-3-(2,2-dibromovinyl)-2,2-dimethylcyclopropanecarboxylate], cycloprothrin [(RS)-α-cyano-3-phenoxybenzyl (RS)-2,2-dichloro-1-(4-ethoxyphenyl)cyclopropanecarboxylate], fluvalinate [α-cyano-3-phenoxybenzyl N-(2-chloro-α,α,α-trifluoro-p-tolyl)-D-valinate], bifenthrin [2-methylbiphenyl-3-ylmethyl (Z)-(1RS)-cis-3-(2-chloro-3,3,3-trifluoroprop-1-enyl)-2,2-dimethylcyclopropanecarboxylate], acrinathrin [cyano(3-phenoxyphenyl)methyl (1R-{1α(S*),3α(Z)})-2,2-dimethyl-3-[3-oxo-3-(2,2,2-trifluoro-1-(trifluoromethyl)ethoxy-1-propenyl)cyclopropanecarboxylate], 2-methyl-2-(4-bromodifluoromethoxyphenyl)propyl 3-phenoxybenzyl ether, tralomethrin [(S)-α-cyano-3-phenoxybenzyl (1R)-cis-3-(1,2,2,2-tetrabromoethyl)-2,2-dimethylcyclopropanecarboxylate], silafluofen [4-ethoxyphenyl(3-(4-fluoro-3-phenoxyphenyl)propyl) dimethylsilane] and so on; thiadiazine derivatives such as buprofezin (2-t-butylimino-3-isopropyl-5-phenyl-1,3,5-thiadiazinan-4-one) and so on; nitroimidazolidine derivatives; nereistoxin derivatives such as cartap (S,S'-(2-dimethylaminotrimethylene) bis(thiocarbamate)), thiocyclam [N,N-dimethyl-1,2,3-trithian-5-ylamine], bensultap [S,S'-2-dimethylaminotrimethylene di(benzenethiosulfonate)] and so on; N-cyanoamidine derivatives such as N-cyano-N'-methyl-N'-(6-chloro-3-pyridylmethyl)acetamidine and so on; chlorinated hydrocarbon compounds such as endosulfan [6,7,8,9,10,10-hexachloro-1,5,5a,6,9,9a-hexahydro-6,9-methano-2,4,3-benzodioxathiepine oxide], γ-BHC (1,2,3,4,5,6-hexachlorocyclohexane), 1,1-bis(chlorophenyl)-2,2,2-trichloroethanol and so on; benzoylphenylurea compounds such as chlorfluazuron [1-(3,5-dichloro-4-(3-chloro -5-trifluoromethylpyridin-2-yloxy)phenyl)-3-(2,6-difluorobenzoyl)urea], teflubenzuron [1-(3,5-dichloro-2,4-difluorophenyl)-3-(2,6-difluorobenzoyl) urea], flufenoxuron [1-(4-(2-chloro-4-trifluoromethylphenoxy)-2-fluorophenyl)-3-(2,6-difluorobenzoyl)urea] and so on; formamidine derivatives such as amitraz [N,N'[(methylimino) dimethylidine]di-2,4-xylidine], chlordimeform [N'-(4-chloro-2-methylphenyl)-N,N-dimethylmethanimidamide] and so on; thiourea derivatives such as diafenthiuron [N-(2,6-diisopropyl-4-phenoxyphenyl)-N'-t-butylcarbodiimide] and so on; phenylpyrazole compounds; tebufenozide [N-t-butyl-N'-(4-ethylbenzoyl)-3,5-dimethylbenzohydrazide]; 4-bromo-2-(4-chlorophenyl)-1-ethoxymethyl-5-trifluoromethylpyrrole-3-carbonitrile; bromopropylate [isopropyl 4,4'-dibromobenzilate]; tetradifon [4-chlorophenyl2,4,5-trichlorophenylsulfone]; chinomethionat [S,S-6-methylquinoxalin-2,3-diyl dithiocarbonate]; propargite [2-(4-t-butylphenoxy)cyclohexyl prop-2-yl sulfite]; fenbutatin oxide [bis[tris(2-methyl-2-phenylpropyl)tin]oxide]; hexythiazox [(4RS,5RS)-5-(4-chlorophenyl)-N-chlorohexyl-4-methyl-2-oxo-1,3-thiazolidine-3-carboxamide];clofentezine [3,6-bis(2-chlorophenyl)-1,2,4,5-tetrazine]; pyridathioben [2-t-butyl-5-(4-t-butylbenzylthio)-4-chloropyridazin-3(2H)-one]; fenpyroximate [t-butyl (E)-4-[(1,3-dimethyl-5-phenoxypyrazol-4-yl) methyleneaminooxymethyl]benzoate]; tebufenpyrad [N-4-(t-butylbenzyl)-4-chloro-3-ethyl-1-methyl-5-pyrazolecarboxamide]; polynactin complex [tetranactin, dinactin, trinactin]; milbemectin; avermectin; ivermectin; azadirachtin [AZAD]; pyrimidifen [5-chloro-N-[2-{4-(2-ethoxyethyl)-2,3-dimethylphenoxy}ethyl]-6-ethylpyrimidin-4-amine]; and pymetrozine [2,3,4,5-tetrahydro-3-oxo-4-[(pyridine-3-yl)methyleneamino]-6-methyl-1,2,4-triazine].

Examples of the plant diseases to be controlled by the present compound include *Pyricularia oryzae* and *Cochliobolus miyabeanus* and *Rhizoctonia solani* of rice; *Erysiphe graminis, Gibberella zeae, Puccinia striiformis, P. graminis, P. recondita, P. hordei, Typhula* sp., *Micronectriella nivalis, Ustilago tritici, U. nuda, Tilletia caries, Pseudocercosporella herpotrichoides, Rhynchosporium secalis, Septoria tritici* and *Leptosphaeria nodorum*, of wheat and barley; *Diaporthe citri, Elsinoe fawcetti, Penicillium digitatum* and *P. italicum* of citrus; *Sclerotinia mali, Valsa mali, Podosphaera leucotricha, Alternaria mali* and *Venturia inaequalis* of apple; *Venturia nashicola, V. pirina, Alternaria kikuchiana* and *Gymnosporangium haraeanum* of pear; *Sclerotinia cinerea, Cladosporium carpophilum* and *Phomopsis* sp. of peach; *Elsinoe ampelina, Glomerella cingulata, Uncinula necator, Phakopsora ampelopsidis, Guignardia bidwellii* and *Plasmopara viticola*, of grape; *Gloeosporium kaki, Cercospora kaki* and *Mycosphaerella nawae* of Japanese persimmon; *Colletotrichum lagenarium, Sphaerothecafuliginea, Mycosphaerella melonis, Fusarium oxysporum, Pseudoperonospora cubensis Phytophthora* sp. and *Pythium* sp. of gourd; *Alternaria solani; Cladosporium fulvum* and *Phytophthora infestans* of tomato; *Phomopsis vexans* and *Erysiphe cichoracearum*, of eggplant; *Alternaria japonica* and *Cercosporella brassicae* of Cruciferae vegetables; *Puccinia allii* of leek; *Cercospora kikuchii, Elsinoe glycines* and *Diaporthe phaseolorum* var. *sojae* of soybean; *Colletotrichum lindemthianum* of kidney bean; *Cercospora personata* and *Cercospora arachidicola* of peanut; *Erysiphe pisi* of pea; *Alternaria solani* and *Phytophthora infestans* of potato; *Sphaerotheca humuli* of strawberry; *Exobasidium reticulatum* and *Elsinoe leucospila* of tea; *Alternaria longipes, Erysiphe cichoracearum, Colletotrichum tabacum, Peronospora tabacina* and *Phytophthora nicotianae* of tobacco; *Cercospora beticola* of sugar beet; *Diplocarpon rosae* and *Sphaerotheca pannosa* of rose; *Septoria chrysanthemi*-indici and *Puccinia horiana* of chrysanthemum; and *Botrytis cinerea* and *Sclerotinia sclerotiorum* of various crops.

Hereinafter, the present invention is explained by production examples, formulation examples and test examples in more detail. The present invention is not restricted by the examples.

At first, the production examples of the present compounds are given below.

PRODUCTION EXAMPLE 1

5-(4-methylpiperidin-1-yl)-6-(2,4,6-trifluorophenyl)-7-chloroimidazo[1,2-a]pyrimidine (Compound 55)

(a) Preparation of diethyl (2,4,6-trifluorophenyl)malonate

Into a mixture of 4.8 g of sodium hydride (60% in oil) and 100 ml of 1,4-dioxane, 19.2 g of diethyl malonate were added dropwise at room temperature, and then 17.2 g of cuprous bromide and 21.1 g of 1-bromo-2,4,6-trifluorobenzene were subsequently added thereto at 40° C. and refluxed for 26 hours under heating. To the reaction mixture, conc. hydrochloric acid was added under ice-cooling, and then tert-butyl methyl ether and water were added. The organic layer was separated, washed with aqueous sodium hydroxide solution, dil. hydrochloric acid and water subsequently, dried over sodium sulfate and concentrated. The residue was subjected to silica gel column chromatography to give 12.6 g of diethyl (2,4,6-trifluorophenyl)malonate.

$^1$H-NMR(CDCl$_3$,TMS)δ(ppm): 1.28 (3H, t, J=7.1 Hz), 4.26 (2H, q, J=7.1 Hz), 4.89 (1H, s), 6.71 (2H, t, J=8.2 Hz)

(b) Preparation of 5,7-dihydroxy-6-(2,4,6-trifluorophenyl)imidazo[1,2-a]pyrimidine A mixture of 2.90 g of diethyl (2,4,6-trifluorophenyl)malonate, 2.39 g of 2-aminoimidazole hydrochloride, 4.57 g of DBU and 10 ml of N,N-dimethylformamide was heated at 100° C. for 6 hours. After allowing the reaction mixture to cool to room temperature, chloroform and water were added thereto. The separated water layer was concentrated, the residue was diluted with water and conc. hydrochloric acid was added thereto under ice-cooling. The precipitation was filtered and dried to give 2.2 g of 5,7-dihydroxy-6-(2,4,6-trifluorophenyl)imidazo[1,2-a]pyrimidine.

(c) Preparation of 5,7-dichloro-6-(2,4,6-trifluorophenyl)imidazo[1,2-a]pyrimidine A mixture of 2.11 g of 5,7-dihydroxy-6-(2,4,6-trifluorophenyl)imidazo[1,2-a]pyrimidine and 5 ml of phosphorus oxychloride was refluxed under heating for 24 hours. After the reaction mixture was concentrated, dichloromethane and aqueous saturated sodium bicarbonate solution were added to the residue. The separated organic layer was washed with aqueous sodium bicarbonate solution and saturated brine, subsequently, dried over anhydrous sodium sulfate and concentrated. The residue was subjected to silica gel column chromatography to give 1.39 g of 5,7-dichloro-6-(2,4,6-trifluorophenyl)imidazo[1,2-a]pyrimidine.

(d) Preparation of 5-(4-methylpiperidin-1-yl)-6-(2,4,6-trifluorophenyl)-7-chloroimidazo[1,2-a]pyrimidine Under ice-cooling, 0.64 g of 5,7-dichloro-6-(2,4,6-trifluorophenyl)imidazo[1,2-a]pyrimidine and 0.79 g of 4-methylpiperidine were mixed. The mixture was allowed to stand at room temperature for one hour, and chloroform and aqueous saturated ammonium chloride solution were added to the reaction mixture. The separated organic layer was washed with water, dried over sodium sulfate and concentrated. The residue was washed with t-butyl methyl ether to give 0.62 g of 5-(4-methylpiperidin-1-yl)-6-(2,4,6-trifluorophenyl)-7-chloroimidazo[1,2-a]pyrimidine

PRODUCTION EXAMPLE 2

5-(4-methylpiperidin-1-yl)-6-(2-chloro-6-fluorophenyl)-7-chloroimidazo[1,2-a]pyrimidine (Compound 182)

(a) Preparation of diethyl (2-chloro-6-fluorophenyl)malonate

Into a mixture of 7.2 g of sodium hydride (60% in oil), 17.0 g of diethyl carbonate and 150 ml of tetrahydrofuran, 26.0 g of ethyl 2-chloro-6-fluorophenylacetate were added dropwise under heating, and then refluxed under heating for 8 hours. The reaction mixture was cooled, poured into iced dil. hydrochloric acid and extracted with t-butyl methyl ether. The organic layer was washed with water, dried over sodium sulfate and concentrated. The residue was subjected to silica gel column chromatography to give 30.4 g of diethyl (2-chloro-6-fluorophenyl)malonate.

$^1$H-NMR(CDCl$_3$,TMS)δ(ppm): 1.28 (3H, t, J=7.1 Hz), 4.26 (2H, q, J=7.1 Hz), 5.16 (1H, s), 7.0–7.1 (1H, m), 7.2–7.4 (2H, m)

(b) Preparation of 5,7-dihydroxy-6-(2-chloro-6-fluorophenyl)imidazo[1,2-a]pyrimidine DBN salt A mixture of 2.89 g of diethyl (2-chloro-6-fluorophenyl)malonate, 1.20 g of aminoimidazole hydrochloride, 2.48 g of 1,5-diazabicyclo[4.3.0]-5-nonene (DBN) and 10 ml of N,N-dimethylformamide (DMF) was heated at 100° C. for 4 hours. The reaction mixture was allowed to cool, filtered the precipitate and dried to give 1.80 g of 5,7-dihydroxy-6-(2-chloro-6-fluorophenyl)imidazo[1,2-a]pyrimidine DBN salt.

(c) Preparation of 5,7-dichloro-6-(2-chloro-6-fluorophenyl)imidazo[1,2-a]pyrimidine A mixture of 1.62 g of 5,7-dihydroxy-6-(2-chloro-6-fluorophenyl)imidazo[1,2-a]pyrimidine DBN salt and 5 ml of phosphorus oxychloride was refluxed under heating for 10 hours. The reaction mixture was concentrated, and dichloromethane and aqueous saturated sodium bicarbonate solution were added to the residue. The separated organic layer was washed with aqueous saturated sodium bicarbonate and water subsequently, dried over sodium sulfate and concentrated. The residue was subjected to silica gel chromatography to give 1.00 g of 5,7-dichloro-6-(2-chloro-6-fluorophenyl)imidazo[1,2-a]pyrimidine.

(d) Preparation of 5-(4-methylpiperidin-1-yl)-6-(2-chloro-6-fluorophenyl)-7-chloroimidazo[1,2-a]pyrimidine Under ice-cooling, 0.63 g of 5,7-dichloro-6-(2-chloro-6-fluorophenyl)imidazo[1,2-a]pyrimidine and 0.79 g of 4-methylpiperidine were mixed. The reaction mixture was allowed to stand at room temperature for 10 minutes, and chloroform and water were added thereto. The separated organic layer was with water, dried over sodium sulfate and concentrated. The residue was subjected to silica gel chromatography to give 0.73 g of 5-(4-methylpiperidin-1-yl)-6-(2-chloro-6-fluorophenyl)-7-chloroimidazo[1,2-a]pyrimidine.

PRODUCTION EXAMPLE 3

5-(4-methylpiperidin-1-yl)-6-(2-chloro-6-fluorophenyl)-7-methylimidazo[1,2-a]pyrimidine (Compound 428)

(a) Preparation of ethyl 2-(2-chloro-6-fluorophenyl)acetoacetate

Into a mixture of 9.6 g of sodium hydride (60% in oil) and 200 ml of tetrahydrofuran, 21.7 g of ethyl 2-chloro-6-fluorophenylacetate were added dropwise under reflux. Then, a solution of 12.3 g of acetic anhydride in 40 ml tetrahydrofuran was added thereto and refluxed under heating for 10 hours. The reaction mixture was cooled, poured into iced dil. hydrochloric acid and extracted with t-butyl methyl ether. The organic layer was washed with dil. hydrochloric acid, aqueous saturated sodium bicarbonate solution, dil. hydrochloric acid and water, subsequently, dried over sodium sulfate and concentrated. The residue was subjected to silica gel column chromatography to give 9.27 g of ethyl (2-chloro-6-fluorophenyl)acetoacetate.

$^1$H-NMR(CDCl$_3$,TMS)δ(ppm): 1.17 (3H, t, J=7.1 Hz), 1.82 (3H, s), 4.1–4.3 (2H, m), 6.9–7.1 (1H, m), 7.2–7.3 (2H, m), 13.2 (1H, s)

(b) Preparation of 5-hydroxy-6-(2-chloro-6-fluorophenyl)-7-methylimidazo[1,2-a]pyrimidine A mixture of 1.29 g of ethyl (2-chloro-6-fluorophenyl)acetoacetate, 0.60 g of aminoimidazole hydrochloride, 1.24 g of 1,5-diazabicyclo[4.3.0]-5-nonene (DBN) and 5 ml of N,N-dimethylformamide was heated at 100° C. for 14 hours. The reaction mixture was allowed to cool, and chloroform and water were added thereto. To the separated water layer, conc. hydrochloric acid was added and the precipitate was filtered, which was followed to subject to silica gel chromatography to give 0.16 g of 5-hydroxy-6-(2-chloro-6-fluorophenyl)-7-methylimidazo[1,2-a]pyrimidine.

(c) Preparation of 5-chloro-6-(2-chloro-6-fluorophenyl)-7-methylimidazo[1,2-a]pyrimidine A mixture of 0.16 g of 5-hydroxy-6-(2-chloro-6-fluorophenyl)-7-methylimidazo[1,2-a]pyrimidine, 0.20 g of N,N-diethylaniline and 2 ml of phosphorus oxychloride was refluxed under heating for 26 hours. The reaction mixture was concentrated, and dichloromethane and aqueous saturated sodium bicarbonate solution were added to the residue. The separated organic layer was washed with water, dried over sodium sulfate and concentrated. The residue was subjected to silica gel chromatography to give 45mg of 5-chloro-6-(2-chloro-6-fluorophenyl)-7-methylimidazo[1,2-a]pyrimidine.

(d) Preparation of 5-(4-methylpiperidin-1-yl)-6-(2-chloro-6-fluorophenyl)-7-methylimidazo[1,2-a]pyrimidine At room temperature, 45 mg (0.16 mmol) of 5-chloro-6-(2-chloro-6-fluorophenyl)-7-methylimidazo[1,2-a]pyrimidine and 63 mg (0.64 mmol) of 4-methylpiperidine were mixed. After one hour, chloroform and aqueous saturated ammonium chloride solution were added to the reaction mixture. The separated organic layer was washed with saturated brine, dried over sodium sulfate and concentrated. The residue was subjected to silica gel chromatography to give 35 mg (0.10 mmol, 61%) of 5-(4-methylpiperidin-1-yl)-6-(2-chloro-6-fluorophenyl)-7-methylimidazo[1,2-a]pyrimidine.

PRODUCTION EXAMPLE 4

5-amino-6-(2,4,6-trifluorophenyl)-7-chloroimidazo [1,2-a]pyrimidine (Compound 1)

A mixture of 0.48 g (1.5 mmol) of 5,7-dichloro-6-(2,4,6-trifluorophenyl)-imidazo[1,2-a]pyrimidine, 5 ml of aqueous ammonia and 10 ml of ethanol was refluxed under heating for 8 hours. The reaction mixture was concentrated.

Water was added to the residue, and the precipitate was obtained by filtration and dried to give 0.30 g (1.0 mmol, 68%) of 5-amino-6-(2,4,6-trifluorophenyl)-7-chloroimidazo [1,2-a]pyrimidine.

PRODUCTION EXAMPLE 5

5-(di-n-propylamino)-6-(2,4,6-trifluorophenyl)-7-chloroimidazo[1,2-a]pyrimidine (Compound 8)

A mixture of 0.095 g of 5,7-dichloro-6-(2,4,6-trifluorophenyl)imidazo[1,2-a]pyrimidine and 0.12 g of di-n-propylamine was heated at 80° C. for one hour. The reaction mixture was allowed to cool, and chloroform and water were added thereto. The separated organic layer was dried over sodium sulfate and concentrated. The residue was subjected to silica gel column chromatography to give 0.095 g of 5-(di-n-propylamino)-6-(2,4,6-trifluorophenyl)-7-chloroimidazo[1,2-a]pyrimidine.

PRODUCTION EXAMPLE 6

5-(2-methylpiperidin-1-yl)-6-(2,4,6-trifluorophenyl)-7-chloroimidazo[1,2-a]pyrimidine (Compound 53)

A mixture of 0.63 g of 5,7-dichloro-6-(2,4,6-trifluorophenyl)-imidazo[1,2-a]pyrimidine, 0.79 g of 2-methylpiperidine and 2 ml of chloroform was heated at 80° C. for one hour. The reaction mixture was allowed to cool and subjected to silica gel column chromatography to give 0.30 g of 5-(2-methylpiperidin-1-yl)-6-(2,4,6-trifluorophenyl)-7-chloroimidazo[1,2-a]pyrimidine.

PRODUCTION EXAMPLE 7

5-(hexamethyleneimin-1-yl)-6-(2,4,6-trifluorophenyl)-7-chloroimidazo[1,2-a]pyrimidine (Compound 72)

At room temperature, 0.32 g of 5,7-dichloro-6-(2,4,6-trifluorophenyl)imidazo[1,2-a]pyrimidine and 0.40 g of hexamethyleneimine were mixed. After 18 hours, water was added to the reaction mixture and the precipitate was obtained by filtration. The filtrate was subjected to silica gel column chromatography to give 0.35 g of 5-(hexamethyleneimin-1-yl)-6-(2,4,6-trifluorophenyl)-7-chloroimidazo[1,2-a]pyrimidine.

PRODUCTION EXAMPLE 8

5-(3,5-dimethylpyrazol-1-yl)-6-(2,4,6-trifluorophenyl)-7-chloroimidazo[1,2-a]pyrimidine (Compound 89)

Into a mixture of 0.040 g of sodium hydride (60% in oil) and 2 ml of tetrahydrofuran, a solution of 0.096 g of 3,5-dimethylpyrazole in 3 ml of tetrahydrofuran was added dropwise. The mixture was added to a solution of 0.32 g of 5,7-dichloro-6-(2,4,6-trifluorophenyl)imidazo[1,2-a]pyrimidine in 5 ml of tetrahydrofuran under ice-cooling. To the reaction mixture, chloroform and aqueous citric acid solution were added. The separated organic layer was washed with water, dried over sodium sulfate and concentrated. The residue was subjected to silica gel column chromatography to give 0.18 g of 5-(3,5-dimethylpyrazol-1-yl)-6-(2,4,6-trifluorophenyl)-7-chloroimidazo[1,2-a]pyrimidine.

PRODUCTION EXAMPLE 9

5-(hexamethyleneimine-1-yl)-6-(2,6-difluorophenyl)-7-chloroimidazo[1,2-a]pyrimidine (Compound 233)

(a) Preparation of diethyl (2,6-difluorophenyl)malonate

Into a mixture of 8.00 g of sodium hydride (60% in oil) and 100 ml of 1,4-dioxane, 32.0 g of ethyl malonate were added dropwise at 60° C., further 14.6 g of cuprous bromide and 19.3 g of 1-bromo-2,6-difluorobenzene were added subsequently, and then refluxed for 16 hours under heating. To the reaction mixture, conc. hydrochloric acid was added under ice-cooling, and then tert-butyl methyl ether and water were added. The separated organic layer was washed with dil. hydrochloric acid and water subsequently, dried over sodium sulfate and concentrated. The residue was distilled under reduced pressure to give 16.5 g of diethyl (2,6-difluorophenyl)malonate. b.p. 107–109° C. (0.14 mmHg)

(b) Preparation of 5,7-dihydroxy-6-(2,6-difluorophenyl)imidazo[1,2-a]pyrimidine

A mixture of 13.6 g of diethyl (2,6-difluorophenyl)malonate, 7.93 g of 2-aminoimidazole sulfate, 9.13 g of DBU and 30 ml of N,N-dimethylformamide was heated at 100° C. for 7 hours. To the reaction mixture, water was added and allowed to cool to room temperature, and t-butyl methyl ether was added thereto. To the separated water layer, conc. hydrochloric acid was added and the precipitate was obtained by filtration and dried to give 7.84 g of 5,7-dihydroxy-6-(2,4,6-trifluorophenyl)imidazo[1,2-a]pyrimidine.

(c) Preparation of 5,7-dichloro-6-(2,6-difluorophenyl)imidazo[1,2-a]pyrimidine

A mixture of 7.63 g of 5,7-dihydroxy-6-(2,6-difluorophenyl)imidazo [1,2-a]pyrimidine, 4.85 g of DBU and 29 ml of phosphorus oxychloride was refluxed under heating for 10 hours. The reaction mixture was concentrated, and chloroform and aqueous saturated sodium bicarbonate solution were added to the residue. The separated organic layer was washed with aqueous saturated sodium bicarbonate solution and saturated brine subsequently, dried over sodium sulfate and concentrated. The residue was subjected to silica gel column chromatography to give 2.48 g of 5,7-dichloro-6-(2,6-difluorophenyl)imidazo[1,2-a]pyrimidine.

(d) Preparation of 5-(hexamethyleneimin-1-yl)-6-(2,6-difluorophenyl)-7-chloroimidazo[1,2-a]pyrimidine 5

At room temperature, 0.30 g of 5,7-dichloro-6-(2,6-difluorophenyl) imidazo[1,2-a]pyrimidine, 0.79 g of hexamethyleneimine and 0.5 ml of chloroform were mixed. The reaction mixture was subjected to silica gel chromatography to give 0.26 g of 5-(hexamethyleneimin-1-yl)-6-(2,6-difluorophenyl)-7-chloroimidazo[1,2-a]pyrimidine.

The present compounds produced by the above-mentioned methods or the like are given below together with their compound numbers, but the present compounds should not be restricted by the following examples.

Compounds given by formula:

TABLE 1

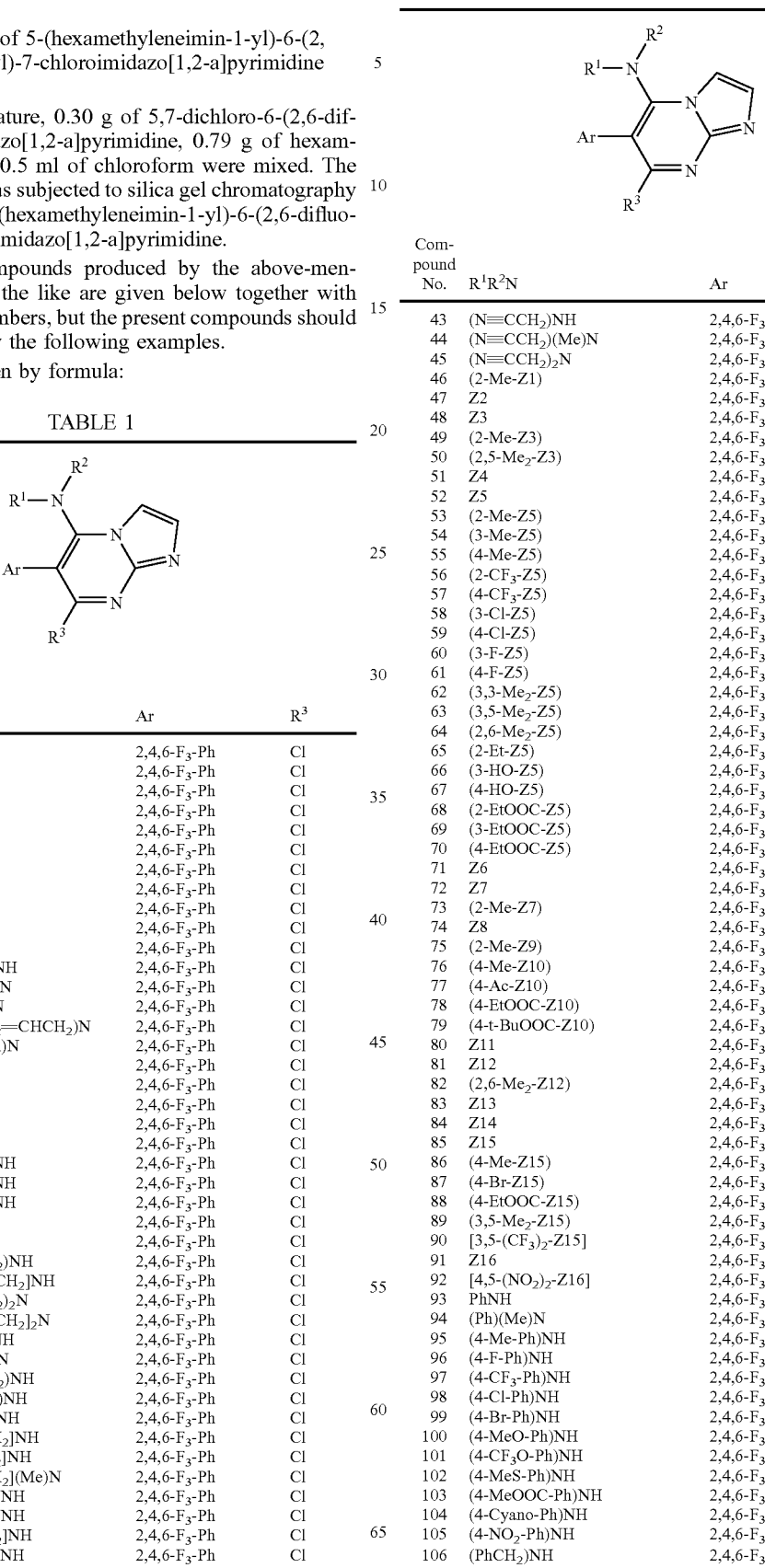

| Compound No. | $R^1R^2N$ | Ar | $R^3$ |
|---|---|---|---|
| 1 | $NH_2$ | 2,4,6-$F_3$-Ph | Cl |
| 2 | MeNH | 2,4,6-$F_3$-Ph | Cl |
| 3 | EtNH | 2,4,6-$F_3$-Ph | Cl |
| 4 | i-PrNH | 2,4,6-$F_3$-Ph | Cl |
| 5 | BuNH | 2,4,6-$F_3$-Ph | Cl |
| 6 | $Me_2N$ | 2,4,6-$F_3$-Ph | Cl |
| 7 | $Et_2N$ | 2,4,6-$F_3$-Ph | Cl |
| 8 | $Pr_2N$ | 2,4,6-$F_3$-Ph | Cl |
| 9 | $Bu_2N$ | 2,4,6-$F_3$-Ph | Cl |
| 10 | $(i-Bu)_2N$ | 2,4,6-$F_3$-Ph | Cl |
| 11 | $(CF_3CH_2)NH$ | 2,4,6-$F_3$-Ph | Cl |
| 12 | $[CF_3CH(Me)]NH$ | 2,4,6-$F_3$-Ph | Cl |
| 13 | $(CF_3CH_2)(Me)N$ | 2,4,6-$F_3$-Ph | Cl |
| 14 | $(CF_3CH_2)(Et)N$ | 2,4,6-$F_3$-Ph | Cl |
| 15 | $(CF_3CH_2)(CH_2=CHCH_2)N$ | 2,4,6-$F_3$-Ph | Cl |
| 16 | $(CF_3CH_2)(i-Bu)N$ | 2,4,6-$F_3$-Ph | Cl |
| 17 | c-PrNH | 2,4,6-$F_3$-Ph | Cl |
| 18 | c-BuNH | 2,4,6-$F_3$-Ph | Cl |
| 19 | c-PentNH | 2,4,6-$F_3$-Ph | Cl |
| 20 | c-HexNH | 2,4,6-$F_3$-Ph | Cl |
| 21 | (c-Hex)(Me)N | 2,4,6-$F_3$-Ph | Cl |
| 22 | (2-Me-c-Hex)NH | 2,4,6-$F_3$-Ph | Cl |
| 23 | (3-Me-c-Hex)NH | 2,4,6-$F_3$-Ph | Cl |
| 24 | (4-Me-c-Hex)NH | 2,4,6-$F_3$-Ph | Cl |
| 25 | c-HepNH | 2,4,6-$F_3$-Ph | Cl |
| 26 | c-OctNH | 2,4,6-$F_3$-Ph | Cl |
| 27 | $(CH_2=CHCH_2)NH$ | 2,4,6-$F_3$-Ph | Cl |
| 28 | $[CH_2=C(Me)CH_2]NH$ | 2,4,6-$F_3$-Ph | Cl |
| 29 | $(CH_2=CHCH_2)_2N$ | 2,4,6-$F_3$-Ph | Cl |
| 30 | $[CH_2=C(Me)CH_2]_2N$ | 2,4,6-$F_3$-Ph | Cl |
| 31 | $(CH\equiv CCH_2)NH$ | 2,4,6-$F_3$-Ph | Cl |
| 32 | $(CH\equiv CCH_2)_2N$ | 2,4,6-$F_3$-Ph | Cl |
| 33 | $(Me_2NCH_2CH_2)NH$ | 2,4,6-$F_3$-Ph | Cl |
| 34 | $(MeOCH_2CH_2)NH$ | 2,4,6-$F_3$-Ph | Cl |
| 35 | $(EtOCH_2CH_2)NH$ | 2,4,6-$F_3$-Ph | Cl |
| 36 | $[(MeO)_2CHCH_2]NH$ | 2,4,6-$F_3$-Ph | Cl |
| 37 | $[(EtO)_2CHCH_2]NH$ | 2,4,6-$F_3$-Ph | Cl |
| 38 | $[(MeO)_2CHCH_2](Me)N$ | 2,4,6-$F_3$-Ph | Cl |
| 39 | $(MeSCH_2CH_2)NH$ | 2,4,6-$F_3$-Ph | Cl |
| 40 | $(MeSCH_2CH_2)NH$ | 2,4,6-$F_3$-Ph | Cl |
| 41 | $[(MeOOC)CH_2]NH$ | 2,4,6-$F_3$-Ph | Cl |
| 42 | $[(EtOOC)CH_2]NH$ | 2,4,6-$F_3$-Ph | Cl |

TABLE 1-continued

| Compound No. | $R^1R^2N$ | Ar | $R^3$ |
|---|---|---|---|
| 43 | $(N\equiv CCH_2)NH$ | 2,4,6-$F_3$-Ph | Cl |
| 44 | $(N\equiv CCH_2)(Me)N$ | 2,4,6-$F_3$-Ph | Cl |
| 45 | $(N\equiv CCH_2)_2N$ | 2,4,6-$F_3$-Ph | Cl |
| 46 | (2-Me-Z1) | 2,4,6-$F_3$-Ph | Cl |
| 47 | Z2 | 2,4,6-$F_3$-Ph | Cl |
| 48 | Z3 | 2,4,6-$F_3$-Ph | Cl |
| 49 | (2-Me-Z3) | 2,4,6-$F_3$-Ph | Cl |
| 50 | (2,5-$Me_2$-Z3) | 2,4,6-$F_3$-Ph | Cl |
| 51 | Z4 | 2,4,6-$F_3$-Ph | Cl |
| 52 | Z5 | 2,4,6-$F_3$-Ph | Cl |
| 53 | (2-Me-Z5) | 2,4,6-$F_3$-Ph | Cl |
| 54 | (3-Me-Z5) | 2,4,6-$F_3$-Ph | Cl |
| 55 | (4-Me-Z5) | 2,4,6-$F_3$-Ph | Cl |
| 56 | (2-$CF_3$-Z5) | 2,4,6-$F_3$-Ph | Cl |
| 57 | (4-$CF_3$-Z5) | 2,4,6-$F_3$-Ph | Cl |
| 58 | (3-Cl-Z5) | 2,4,6-$F_3$-Ph | Cl |
| 59 | (4-Cl-Z5) | 2,4,6-$F_3$-Ph | Cl |
| 60 | (3-F-Z5) | 2,4,6-$F_3$-Ph | Cl |
| 61 | (4-F-Z5) | 2,4,6-$F_3$-Ph | Cl |
| 62 | (3,3-$Me_2$-Z5) | 2,4,6-$F_3$-Ph | Cl |
| 63 | (3,5-$Me_2$-Z5) | 2,4,6-$F_3$-Ph | Cl |
| 64 | (2,6-$Me_2$-Z5) | 2,4,6-$F_3$-Ph | Cl |
| 65 | (2-Et-Z5) | 2,4,6-$F_3$-Ph | Cl |
| 66 | (3-HO-Z5) | 2,4,6-$F_3$-Ph | Cl |
| 67 | (4-HO-Z5) | 2,4,6-$F_3$-Ph | Cl |
| 68 | (2-EtOOC-Z5) | 2,4,6-$F_3$-Ph | Cl |
| 69 | (3-EtOOC-Z5) | 2,4,6-$F_3$-Ph | Cl |
| 70 | (4-EtOOC-Z5) | 2,4,6-$F_3$-Ph | Cl |
| 71 | Z6 | 2,4,6-$F_3$-Ph | Cl |
| 72 | Z7 | 2,4,6-$F_3$-Ph | Cl |
| 73 | (2-Me-Z7) | 2,4,6-$F_3$-Ph | Cl |
| 74 | Z8 | 2,4,6-$F_3$-Ph | Cl |
| 75 | (2-Me-Z9) | 2,4,6-$F_3$-Ph | Cl |
| 76 | (4-Me-Z10) | 2,4,6-$F_3$-Ph | Cl |
| 77 | (4-Ac-Z10) | 2,4,6-$F_3$-Ph | Cl |
| 78 | (4-EtOOC-Z10) | 2,4,6-$F_3$-Ph | Cl |
| 79 | (4-t-BuOOC-Z10) | 2,4,6-$F_3$-Ph | Cl |
| 80 | Z11 | 2,4,6-$F_3$-Ph | Cl |
| 81 | Z12 | 2,4,6-$F_3$-Ph | Cl |
| 82 | (2,6-$Me_2$-Z12) | 2,4,6-$F_3$-Ph | Cl |
| 83 | Z13 | 2,4,6-$F_3$-Ph | Cl |
| 84 | Z14 | 2,4,6-$F_3$-Ph | Cl |
| 85 | Z15 | 2,4,6-$F_3$-Ph | Cl |
| 86 | (4-Me-Z15) | 2,4,6-$F_3$-Ph | Cl |
| 87 | (4-Br-Z15) | 2,4,6-$F_3$-Ph | Cl |
| 88 | (4-EtOOC-Z15) | 2,4,6-$F_3$-Ph | Cl |
| 89 | (3,5-$Me_2$-Z15) | 2,4,6-$F_3$-Ph | Cl |
| 90 | [3,5-$(CF_3)_2$-Z15] | 2,4,6-$F_3$-Ph | Cl |
| 91 | Z16 | 2,4,6-$F_3$-Ph | Cl |
| 92 | [4,5-$(NO_2)_2$-Z16] | 2,4,6-$F_3$-Ph | Cl |
| 93 | PhNH | 2,4,6-$F_3$-Ph | Cl |
| 94 | (Ph)(Me)N | 2,4,6-$F_3$-Ph | Cl |
| 95 | (4-Me-Ph)NH | 2,4,6-$F_3$-Ph | Cl |
| 96 | (4-F-Ph)NH | 2,4,6-$F_3$-Ph | Cl |
| 97 | (4-$CF_3$-Ph)NH | 2,4,6-$F_3$-Ph | Cl |
| 98 | (4-Cl-Ph)NH | 2,4,6-$F_3$-Ph | Cl |
| 99 | (4-Br-Ph)NH | 2,4,6-$F_3$-Ph | Cl |
| 100 | (4-MeO-Ph)NH | 2,4,6-$F_3$-Ph | Cl |
| 101 | (4-$CF_3$O-Ph)NH | 2,4,6-$F_3$-Ph | Cl |
| 102 | (4-MeS-Ph)NH | 2,4,6-$F_3$-Ph | Cl |
| 103 | (4-MeOOC-Ph)NH | 2,4,6-$F_3$-Ph | Cl |
| 104 | (4-Cyano-Ph)NH | 2,4,6-$F_3$-Ph | Cl |
| 105 | (4-$NO_2$-Ph)NH | 2,4,6-$F_3$-Ph | Cl |
| 106 | $(PhCH_2)NH$ | 2,4,6-$F_3$-Ph | Cl |

TABLE 1-continued

| Compound No. | R¹R²N | Ar | R³ |
|---|---|---|---|
| 107 | [PhCH(Me)]NH | 2,4,6-F$_3$-Ph | Cl |
| 108 | (PhCH$_2$CH$_2$)NH | 2,4,6-F$_3$-Ph | Cl |
| 109 | (PhCH$_2$)(Me)N | 2,4,6-F$_3$-Ph | Cl |
| 110 | [(4-Me-Ph)CH$_2$]NH | 2,4,6-F$_3$-Ph | Cl |
| 111 | [(4-CF$_3$-Ph)CH$_2$]NH | 2,4,6-F$_3$-Ph | Cl |
| 112 | [(4-F-Ph)CH$_2$]NH | 2,4,6-F$_3$-Ph | Cl |
| 113 | [(4-Cl-Ph)CH$_2$]NH | 2,4,6-F$_3$-Ph | Cl |
| 114 | [(4-Br-Ph)CH$_2$]NH | 2,4,6-F$_3$-Ph | Cl |
| 115 | [(4-MeO-Ph)CH$_2$]NH | 2,4,6-F$_3$-Ph | Cl |
| 116 | [(4-CF$_3$O-Ph)CH$_2$]NH | 2,4,6-F$_3$-Ph | Cl |
| 117 | [(4-MeO-Ph)CH$_2$CH$_2$]NH | 2,4,6-F$_3$-Ph | Cl |
| 118 | {[3,4-(MeO)$_2$-Ph]CH$_2$CH$_2$}NH | 2,4,6-F$_3$-Ph | Cl |
| 119 | [(4-NO$_2$-Ph)CH$_2$]NH | 2,4,6-F$_3$-Ph | Cl |
| 120 | (Z3)NH | 2,4,6-F$_3$-Ph | Cl |
| 121 | (Z5)NH | 2,4,6-F$_3$-Ph | Cl |
| 122 | (4-Me-Z10)NH | 2,4,6-F$_3$-Ph | Cl |
| 123 | (Z12)NH | 2,4,6-F$_3$-Ph | Cl |
| 124 | (1-EtOOC-Piperidin-4-yl)NH | 2,4,6-F$_3$-Ph | Cl |
| 125 | (2-Thiazolin-2-yl)NH | 2,4,6-F$_3$-Ph | Cl |
| 126 | (1-Et-Pyrazol-5-yl)NH | 2,4,6-F$_3$-Ph | Cl |
| 127 | (1,2,4-Triazol-3-yl)NH | 2,4,6-F$_3$-Ph | Cl |
| 128 | (3-Me-Isoxazol-5-yl)NH | 2,4,6-F$_3$-Ph | Cl |
| 129 | (5-Me-Isoxazol-3-yl)NH | 2,4,6-F$_3$-Ph | Cl |
| 130 | (3-Me-Isothiazol-5-yl)NH | 2,4,6-F$_3$-Ph | Cl |
| 131 | (Thiazol-2-yl)NH | 2,4,6-F$_3$-Ph | Cl |
| 132 | (1,3,4-Thiadiazol-2-yl)NH | 2,4,6-F$_3$-Ph | Cl |
| 133 | (Pyridin-2-yl)NH | 2,4,6-F$_3$-Ph | Cl |
| 134 | (Pyridin-3-yl)NH | 2,4,6-F$_3$-Ph | Cl |
| 135 | (Pyridin-4-yl)NH | 2,4,6-F$_3$-Ph | Cl |
| 136 | (5-Me-Pyridin-2-yl)NH | 2,4,6-F$_3$-Ph | Cl |
| 137 | (5-Cl-Pyridin-2-yl)NH | 2,4,6-F$_3$-Ph | Cl |
| 138 | (5-Br-Pyridin-2-yl)NH | 2,4,6-F$_3$-Ph | Cl |
| 139 | (6-MeO-Pyridin-3-yl)NH | 2,4,6-F$_3$-Ph | Cl |
| 140 | (3-Cl-5-CF$_3$-Pyridin-2-yl)NH | 2,4,6-F$_3$-Ph | Cl |
| 141 | (5-NO$_2$-Pyridin-2-yl)NH | 2,4,6-F$_3$-Ph | Cl |
| 142 | (Pyrimidin-2-yl)NH | 2,4,6-F$_3$-Ph | Cl |
| 143 | (Pyrimidin-4-yl)NH | 2,4,6-F$_3$-Ph | Cl |
| 144 | (6-Cl-2-MeS-Pyrimidin-4-yl)NH | 2,4,6-F$_3$-Ph | Cl |
| 145 | (Pyrazin-2-yl)NH | 2,4,6-F$_3$-Ph | Cl |
| 146 | (1,2,4-Triazin-3-yl)NH | 2,4,6-F$_3$-Ph | Cl |
| 147 | (NH$_2$)NH | 2,4,6-F$_3$-Ph | Cl |
| 148 | (Me$_2$N)NH | 2,4,6-F$_3$-Ph | Cl |
| 149 | (PhNH)NH | 2,4,6-F$_3$-Ph | Cl |
| 150 | (MeNH)(Me)N | 2,4,6-F$_3$-Ph | Cl |
| 151 | (MeO)NH | 2,4,6-F$_3$-Ph | Cl |
| 152 | (EtO)NH | 2,4,6-F$_3$-Ph | Cl |
| 153 | (t-BuO)NH | 2,4,6-F$_3$-Ph | Cl |
| 154 | (PhCH$_2$O)NH | 2,4,6-F$_3$-Ph | Cl |
| 155 | (MeO)(Me)N | 2,4,6-F$_3$-Ph | Cl |
| 156 | NH$_2$ | 2-Cl-6-F-Ph | Cl |
| 157 | MeNH | 2-Cl-6-F-Ph | Cl |
| 158 | EtNH | 2-Cl-6-F-Ph | Cl |
| 159 | i-PrNH | 2-Cl-6-F-Ph | Cl |
| 160 | Me$_2$N | 2-Cl-6-F-Ph | Cl |
| 161 | Et$_2$N | 2-Cl-6-F-Ph | Cl |
| 162 | Pr$_2$N | 2-Cl-6-F-Ph | Cl |
| 163 | Bu$_2$N | 2-Cl-6-F-Ph | Cl |
| 164 | (i-Bu)$_2$N | 2-Cl-6-F-Ph | Cl |
| 165 | (CF$_3$CH$_2$)NH | 2-Cl-6-F-Ph | Cl |
| 166 | [CF$_3$CH(Me)]NH | 2-Cl-6-F-Ph | Cl |
| 167 | c-PentNH | 2-Cl-6-F-Ph | Cl |
| 168 | c-HexNH | 2-Cl-6-F-Ph | Cl |
| 169 | (c-Hex)(Me)N | 2-Cl-6-F-Ph | Cl |
| 170 | (CH$_2$=CHCH$_2$)NH | 2-Cl-6-F-Ph | Cl |
| 171 | (CH$_2$=CHCH$_2$)$_2$N | 2-Cl-6-F-Ph | Cl |
| 172 | [CH$_2$=C(Me)CH$_2$]$_2$N | 2-Cl-6-F-Ph | Cl |
| 173 | (CH≡CCH$_2$)NH | 2-Cl-6-F-Ph | Cl |
| 174 | (CH≡CCH$_2$)$_2$N | 2-Cl-6-F-Ph | Cl |
| 175 | Z3 | 2-Cl-6-F-Ph | Cl |
| 176 | (2-Me-Z3) | 2-Cl-6-F-Ph | Cl |
| 177 | (2,5-Me$_2$-Z3) | 2-Cl-6-F-Ph | Cl |
| 178 | Z4 | 2-Cl-6-F-Ph | Cl |
| 179 | Z5 | 2-Cl-6-F-Ph | Cl |
| 180 | (2-Me-Z5) | 2-Cl-6-F-Ph | Cl |
| 181 | (3-Me-Z5) | 2-Cl-6-F-Ph | Cl |
| 182 | (4-Me-Z5) | 2-Cl-6-F-Ph | Cl |
| 183 | (3,3-Me$_2$-Z5) | 2-Cl-6-F-Ph | Cl |
| 184 | (3,5-Me$_2$-Z5) | 2-Cl-6-F-Ph | Cl |
| 185 | (2,6-Me$_2$-Z5) | 2-Cl-6-F-Ph | Cl |
| 186 | Z6 | 2-Cl-6-F-Ph | Cl |
| 187 | Z7 | 2-Cl-6-F-Ph | Cl |
| 188 | (2-Me-Z7) | 2-Cl-6-F-Ph | Cl |
| 189 | Z8 | 2-Cl-6-F-Ph | Cl |
| 190 | (4-Me-Z10) | 2-Cl-6-F-Ph | Cl |
| 191 | Z11 | 2-Cl-6-F-Ph | Cl |
| 192 | Z12 | 2-Cl-6-F-Ph | Cl |
| 193 | (2,6-Me$_2$-Z12) | 2-Cl-6-F-Ph | Cl |
| 194 | Z13 | 2-Cl-6-F-Ph | Cl |
| 195 | Z14 | 2-Cl-6-F-Ph | Cl |
| 196 | Z15 | 2-Cl-6-F-Ph | Cl |
| 197 | Z16 | 2-Cl-6-F-Ph | Cl |
| 198 | PhNH | 2-Cl-6-F-Ph | Cl |
| 199 | (Ph)(Me)N | 2-Cl-6-F-Ph | Cl |
| 200 | (PhCH$_2$)NH | 2-Cl-6-F-Ph | Cl |
| 201 | (PhCH$_2$)(Me)N | 2-Cl-6-F-Ph | Cl |
| 202 | NH$_2$ | 2,6-F$_2$-Ph | Cl |
| 203 | MeNH | 2,6-F$_2$-Ph | Cl |
| 204 | EtNH | 2,6-F$_2$-Ph | Cl |
| 205 | i-PrNH | 2,6-F$_2$-Ph | Cl |
| 206 | Me$_2$N | 2,6-F$_2$-Ph | Cl |
| 207 | Et$_2$N | 2,6-F$_2$-Ph | Cl |
| 208 | Pr$_2$N | 2,6-F$_2$-Ph | Cl |
| 209 | Bu$_2$N | 2,6-F$_2$-Ph | Cl |
| 210 | (i-Bu)$_2$N | 2,6-F$_2$-Ph | Cl |
| 211 | (CF$_3$CH$_2$)NH | 2,6-F$_2$-Ph | Cl |
| 212 | [CF$_3$CH(Me)]NH | 2,6-F$_2$-Ph | Cl |
| 213 | c-PentNH | 2,6-F$_2$-Ph | Cl |
| 214 | c-HexNH | 2,6-F$_2$-Ph | Cl |
| 215 | (c-Hex)(Me)N | 2,6-F$_2$-Ph | Cl |
| 216 | (CH$_2$=CHCH$_2$)NH | 2,6-F$_2$-Ph | Cl |
| 217 | (CH$_2$=CHCH$_2$)$_2$N | 2,6-F$_2$-Ph | Cl |
| 218 | [CH$_2$=C(Me)CH$_2$]$_2$N | 2,6-F$_2$-Ph | Cl |
| 219 | (CH≡CCH$_2$)NH | 2,6-F$_2$-Ph | Cl |
| 220 | (CH≡CCH$_2$)$_2$N | 2,6-F$_2$-Ph | Cl |
| 221 | Z3 | 2,6-F$_2$-Ph | Cl |
| 222 | (2-Me-Z3) | 2,6-F$_2$-Ph | Cl |
| 223 | (2,5-Me$_2$-Z3) | 2,6-F$_2$-Ph | Cl |
| 224 | Z4 | 2,6-F$_2$-Ph | Cl |
| 225 | Z5 | 2,6-F$_2$-Ph | Cl |
| 226 | (2-Me-Z5) | 2,6-F$_2$-Ph | Cl |
| 227 | (3-Me-Z5) | 2,6-F$_2$-Ph | Cl |
| 228 | (4-Me-Z5) | 2,6-F$_2$-Ph | Cl |
| 229 | (3,3-Me$_2$-Z5) | 2,6-F$_2$-Ph | Cl |
| 230 | (3,5-Me$_2$-Z5) | 2,6-F$_2$-Ph | Cl |
| 231 | (2,6-Me$_2$-Z5) | 2,6-F$_2$-Ph | Cl |
| 232 | Z6 | 2,6-F$_2$-Ph | Cl |
| 233 | Z7 | 2,6-F$_2$-Ph | Cl |
| 234 | (2-Me-Z7) | 2,6-F$_2$-Ph | Cl |

TABLE 1-continued

| Compound No. | R¹R²N | Ar | R³ |
|---|---|---|---|
| 235 | Z8 | 2,6-F$_2$-Ph | Cl |
| 236 | (4-Me-Z10) | 2,6-F$_2$-Ph | Cl |
| 237 | Z11 | 2,6-F$_2$-Ph | Cl |
| 238 | Z12 | 2,6-F$_2$-Ph | Cl |
| 239 | (2,6-Me$_2$-Z12) | 2,6-F$_2$-Ph | Cl |
| 240 | Z13 | 2,6-F$_2$-Ph | Cl |
| 241 | Z14 | 2,6-F$_2$-Ph | Cl |
| 242 | Z15 | 2,6-F$_2$-Ph | Cl |
| 243 | Z16 | 2,6-F$_2$-Ph | Cl |
| 244 | PhNH | 2,6-F$_2$-Ph | Cl |
| 245 | (Ph)(Me)N | 2,6-F$_2$-Ph | Cl |
| 246 | (PhCH$_2$)NH | 2,6-F$_2$-Ph | Cl |
| 247 | (PhCH$_2$)(Me)N | 2,6-F$_2$-Ph | Cl |
| 248 | Z5 | Ph | Cl |
| 249 | (4-Me-Z5) | Ph | Cl |
| 250 | (2-Me-Z5) | Ph | Cl |
| 251 | Z7 | Ph | Cl |
| 252 | Z5 | 2-Cl-Ph | Cl |
| 253 | (4-Me-Z5) | 2-Cl-Ph | Cl |
| 254 | (2-Me-Z5) | 2-Cl-Ph | Cl |
| 255 | Z7 | 2-Cl-Ph | Cl |
| 256 | Z5 | 2-F-Ph | Cl |
| 257 | (4-Me-Z5) | 2-F-Ph | Cl |
| 258 | (2-Me-Z5) | 2-F-Ph | Cl |
| 259 | Z7 | 2-F-Ph | Cl |
| 260 | Z5 | 2-Me-Ph | Cl |
| 261 | (4-Me-Z5) | 2-Me-Ph | Cl |
| 262 | (2-Me-Z5) | 2-Me-Ph | Cl |
| 263 | Z7 | 2-Me-Ph | Cl |
| 264 | Z5 | 2-CF$_3$-Ph | Cl |
| 265 | (4-Me-Z5) | 2-CF$_3$-Ph | Cl |
| 266 | (2-Me-Z5) | 2-CF$_3$-Ph | Cl |
| 267 | Z7 | 2-CF$_3$-Ph | Cl |
| 268 | Z5 | 3-Cl-Ph | Cl |
| 269 | (4-Me-Z5) | 3-Cl-Ph | Cl |
| 270 | (2-Me-Z5) | 3-Cl-Ph | Cl |
| 271 | Z7 | 3-Cl-Ph | Cl |
| 272 | Z5 | 3-F-Ph | Cl |
| 273 | (4-Me-Z5) | 3-F-Ph | Cl |
| 274 | (2-Me-Z5) | 3-F-Ph | Cl |
| 275 | Z7 | 3-F-Ph | Cl |
| 276 | Z5 | 4-Cl-Ph | Cl |
| 277 | (4-Me-Z5) | 4-Cl-Ph | Cl |
| 278 | (2-Me-Z5) | 4-Cl-Ph | Cl |
| 279 | Z7 | 4-Cl-Ph | Cl |
| 280 | Z5 | 4-F-Ph | Cl |
| 281 | (4-Me-Z5) | 4-F-Ph | Cl |
| 282 | (2-Me-Z5) | 4-F-Ph | Cl |
| 283 | Z7 | 4-F-Ph | Cl |
| 284 | Z5 | 2,6-Cl$_2$-Ph | Cl |
| 285 | (4-Me-Z5) | 2,6-Cl$_2$-Ph | Cl |
| 286 | (2-Me-Z5) | 2,6-Cl$_2$-Ph | Cl |
| 287 | Z7 | 2,6-Cl$_2$-Ph | Cl |
| 288 | Z5 | 2,4-Cl$_2$-Ph | Cl |
| 289 | (4-Me-Z5) | 2,4-Cl$_2$-Ph | Cl |
| 290 | (2-Me-Z5) | 2,4-Cl$_2$-Ph | Cl |
| 291 | Z7 | 2,4-Cl$_2$-Ph | Cl |
| 292 | Z5 | 2,4-F$_2$-Ph | Cl |
| 293 | (4-Me-Z5) | 2,4-F$_2$-Ph | Cl |
| 294 | (2-Me-Z5) | 2,4-F$_2$-Ph | Cl |
| 295 | Z7 | 2,4-F$_2$-Ph | Cl |
| 296 | Z5 | 3,5-Cl$_2$-Ph | Cl |
| 297 | (4-Me-Z5) | 3,5-Cl$_2$-Ph | Cl |
| 298 | (2-Me-Z5) | 3,5-Cl$_2$-Ph | Cl |
| 299 | Z7 | 3,5-Cl$_2$-Ph | Cl |
| 300 | Z5 | 3,5-F$_2$-Ph | Cl |
| 301 | (4-Me-Z5) | 3,5-F$_2$-Ph | Cl |
| 302 | (2-Me-Z5) | 3,5-F$_2$-Ph | Cl |
| 303 | Z7 | 3,5-F$_2$-Ph | Cl |
| 304 | Z5 | 2,4,6-Cl$_3$-Ph | Cl |
| 305 | (4-Me-Z5) | 2,4,6-Cl$_3$-Ph | Cl |
| 306 | (2-Me-Z5) | 2,4,6-Cl$_3$-Ph | Cl |
| 307 | Z7 | 2,4,6-Cl$_3$-Ph | Cl |
| 308 | Z5 | 2,6-Cl$_2$-4-F-Ph | Cl |
| 309 | (4-Me-Z5) | 2,6-Cl$_2$-4-F-Ph | Cl |
| 310 | (2-Me-Z5) | 2,6-Cl$_2$-4-F-Ph | Cl |
| 311 | Z7 | 2,6-Cl$_2$-4-F-Ph | Cl |
| 312 | Z5 | 2,4-Cl$_2$-6-F-Ph | Cl |
| 313 | (4-Me-Z5) | 2,4-Cl$_2$-6-F-Ph | Cl |
| 314 | (2-Me-Z5) | 2,4-Cl$_2$-6-F-Ph | Cl |
| 315 | Z7 | 2,4-Cl$_2$-6-F-Ph | Cl |
| 316 | Z5 | 2-Cl-4,6-F$_2$-Ph | Cl |
| 317 | (4-Me-Z5) | 2-Cl-4,6-F$_2$-Ph | Cl |
| 318 | (2-Me-Z5) | 2-Cl-4,6-F$_2$-Ph | Cl |
| 319 | Z7 | 2-Cl-4,6-F$_2$-Ph | Cl |
| 320 | Z5 | 4-Cl-2,6-F$_2$-Ph | Cl |
| 321 | (4-Me-Z5) | 4-Cl-2,6-F$_2$-Ph | Cl |
| 322 | (2-Me-Z5) | 4-Cl-2,6-F$_2$-Ph | Cl |
| 323 | Z7 | 4-Cl-2,6-F$_2$-Ph | Cl |
| 324 | Z5 | 2,6-F$_2$-4-(MeO)-Ph | Cl |
| 325 | (4-Me-Z5) | 2,6-F$_2$-4-(MeO)-Ph | Cl |
| 326 | (2-Me-Z5) | 2,6-F$_2$-4-(MeO)-Ph | Cl |
| 327 | Z7 | 2,6-F$_2$-4-(MeO)-Ph | Cl |
| 328 | Z5 | 2,3,6-F$_3$-Ph | Cl |
| 329 | (4-Me-Z5) | 2,3,6-F$_3$-Ph | Cl |
| 330 | (2-Me-Z5) | 2,3,6-F$_3$-Ph | Cl |
| 331 | Z7 | 2,3,6-F$_3$-Ph | Cl |
| 332 | Z5 | 2,3,4,5,6-F$_5$-Ph | Cl |
| 333 | (4-Me-Z5) | 2,3,4,5,6-F$_5$-Ph | Cl |
| 334 | (2-Me-Z5) | 2,3,4,5,6-F$_5$-Ph | Cl |
| 335 | Z7 | 2,3,4,5,6-F$_5$-Ph | Cl |
| 336 | Z5 | 3-F-6-CF$_3$-Ph | Cl |
| 337 | (4-Me-Z5) | 3-F-6-CF$_3$-Ph | Cl |
| 338 | (2-Me-Z5) | 3-F-6-CF$_3$-Ph | Cl |
| 339 | Z7 | 3-F-6-CF$_3$-Ph | Cl |
| 340 | Z5 | 2,4,6-Me$_3$-Ph | Cl |
| 341 | (4-Me-Z5) | 2,4,6-Me$_3$-Ph | Cl |
| 342 | (2-Me-Z5) | 2,4,6-Me$_3$-Ph | Cl |
| 343 | Z7 | 2,4,6-Me$_3$-Ph | Cl |
| 344 | NH$_2$ | 2,4,6-F$_3$-Ph | Me |
| 345 | MeNH | 2,4,6-F$_3$-Ph | Me |
| 346 | EtNH | 2,4,6-F$_3$-Ph | Me |
| 347 | i-PrNH | 2,4,6-F$_3$-Ph | Me |
| 348 | Me$_2$N | 2,4,6-F$_3$-Ph | Me |
| 349 | Et$_2$N | 2,4,6-F$_3$-Ph | Me |
| 350 | Pr$_2$N | 2,4,6-F$_3$-Ph | Me |
| 351 | Bu$_2$N | 2,4,6-F$_3$-Ph | Me |
| 352 | (i-Bu)$_2$N | 2,4,6-F$_3$-Ph | Me |
| 353 | (CF$_3$CH$_2$)NH | 2,4,6-F$_3$-Ph | Me |
| 354 | [CF$_3$CH(Me)]NH | 2,4,6-F$_3$-Ph | Me |
| 355 | c-PentNH | 2,4,6-F$_3$-Ph | Me |
| 356 | c-HexNH | 2,4,6-F$_3$-Ph | Me |
| 357 | (c-Hex)(Me)N | 2,4,6-F$_3$-Ph | Me |
| 358 | (CH$_2$=CHCH$_2$)NH | 2,4,6-F$_3$-Ph | Me |
| 359 | (CH$_2$=CHCH$_2$)$_2$N | 2,4,6-F$_3$-Ph | Me |
| 360 | [CH$_2$=C(Me)CH$_2$]$_2$N | 2,4,6-F$_3$-Ph | Me |
| 361 | (CH≡CCH$_2$)NH | 2,4,6-F$_3$-Ph | Me |
| 362 | (CH≡CCH$_2$)$_2$N | 2,4,6-F$_3$-Ph | Me |

TABLE 1-continued

[Structure: R¹R²N-substituted imidazo-pyrimidine with Ar and R³ substituents]

| Compound No. | R¹R²N | Ar | R³ |
|---|---|---|---|
| 363 | Z3 | 2,4,6-F₃-Ph | Me |
| 364 | (2-Me-Z3) | 2,4,6-F₃-Ph | Me |
| 365 | (2,5-Me₂-Z3) | 2,4,6-F₃-Ph | Me |
| 366 | Z4 | 2,4,6-F₃-Ph | Me |
| 367 | Z5 | 2,4,6-F₃-Ph | Me |
| 368 | (2-Me-Z5) | 2,4,6-F₃-Ph | Me |
| 369 | (3-Me-Z5) | 2,4,6-F₃-Ph | Me |
| 370 | (4-Me-Z5) | 2,4,6-F₃-Ph | Me |
| 371 | (3,3-Me₂-Z5) | 2,4,6-F₃-Ph | Me |
| 372 | (3,5-Me₂-Z5) | 2,4,6-F₃-Ph | Me |
| 373 | (2,6-Me₂-Z5) | 2,4,6-F₃-Ph | Me |
| 374 | Z6 | 2,4,6-F₃-Ph | Me |
| 375 | Z7 | 2,4,6-F₃-Ph | Me |
| 376 | (2-Me-Z7) | 2,4,6-F₃-Ph | Me |
| 377 | Z8 | 2,4,6-F₃-Ph | Me |
| 378 | (4-Me-Z10) | 2,4,6-F₃-Ph | Me |
| 379 | Z11 | 2,4,6-F₃-Ph | Me |
| 380 | Z12 | 2,4,6-F₃-Ph | Me |
| 381 | (2,6-Me₂-Z12) | 2,4,6-F₃-Ph | Me |
| 382 | Z13 | 2,4,6-F₃-Ph | Me |
| 383 | Z14 | 2,4,6-F₃-Ph | Me |
| 384 | Z15 | 2,4,6-F₃-Ph | Me |
| 385 | Z16 | 2,4,6-F₃-Ph | Me |
| 386 | PhNH | 2,4,6-F₃-Ph | Me |
| 387 | (Ph)(Me)N | 2,4,6-F₃-Ph | Me |
| 388 | (PhCH₂)NH | 2,4,6-F₃-Ph | Me |
| 389 | (PhCH₂)(Me)N | 2,4,6-F₃-Ph | Me |
| 390 | Z5 | 2,4,6-F₃-Ph | Et |
| 391 | (4-Me-Z5) | 2,4,6-F₃-Ph | Et |
| 392 | (2-Me-Z5) | 2,4,6-F₃-Ph | Et |
| 393 | Z7 | 2,4,6-F₃-Ph | Et |
| 394 | Z5 | 2,4,6-F₃-Ph | Pr |
| 395 | (4-Me-Z5) | 2,4,6-F₃-Ph | Pr |
| 396 | (2-Me-Z5) | 2,4,6-F₃-Ph | Pr |
| 397 | Z7 | 2,4,6-F₃-Ph | Pr |
| 398 | Z5 | 2,4,6-F₃-Ph | i-Pr |
| 399 | (4-Me-Z5) | 2,4,6-F₃-Ph | i-Pr |
| 400 | (2-Me-Z5) | 2,4,6-F₃-Ph | i-Pr |
| 401 | Z7 | 2,4,6-F₃-Ph | i-Pr |
| 402 | NH₂ | 2-Cl-6-F-Ph | Me |
| 403 | MeNH | 2-Cl-6-F-Ph | Me |
| 404 | EtNH | 2-Cl-6-F-Ph | Me |
| 405 | i-PrNH | 2-Cl-6-F-Ph | Me |
| 406 | Me₂N | 2-Cl-6-F-Ph | Me |
| 407 | Et₂N | 2-Cl-6-F-Ph | Me |
| 408 | Pr₂N | 2-Cl-6-F-Ph | Me |
| 409 | Bu₂N | 2-Cl-6-F-Ph | Me |
| 410 | (i-Bu)₂N | 2-Cl-6-F-Ph | Me |
| 411 | (CF₃CH₂)NH | 2-Cl-6-F-Ph | Me |
| 412 | [CF₃CH(Me)]NH | 2-Cl-6-F-Ph | Me |
| 413 | c-PentNH | 2-Cl-6-F-Ph | Me |
| 414 | c-HexNH | 2-Cl-6-F-Ph | Me |
| 415 | (c-Hex)(Me)N | 2-Cl-6-F-Ph | Me |
| 416 | (CH₂=CHCH₂)NH | 2-Cl-6-F-Ph | Me |
| 417 | (CH₂=CHCH₂)₂N | 2-Cl-6-F-Ph | Me |
| 418 | [CH₂=C(Me)CH₂]N | 2-Cl-6-F-Ph | Me |
| 419 | (CH≡CCH₂)NH | 2-Cl-6-F-Ph | Me |
| 420 | (CH≡CCH₂)₂N | 2-Cl-6-F-Ph | Me |
| 421 | Z3 | 2-Cl-6-F-Ph | Me |
| 422 | (2-Me-Z3) | 2-Cl-6-F-Ph | Me |
| 423 | (2,5-Me₂-Z3) | 2-Cl-6-F-Ph | Me |
| 424 | Z4 | 2-Cl-6-F-Ph | Me |
| 425 | Z5 | 2-Cl-6-F-Ph | Me |
| 426 | (2-Me-Z5) | 2-Cl-6-F-Ph | Me |
| 427 | (3-Me-Z5) | 2-Cl-6-F-Ph | Me |
| 428 | (4-Me-Z5) | 2-Cl-6-F-Ph | Me |
| 429 | (3,3-Me₂-Z5) | 2-Cl-6-F-Ph | Me |
| 430 | (3,5-Me₂-Z5) | 2-Cl-6-F-Ph | Me |
| 431 | (2,6-Me₂-Z5) | 2-Cl-6-F-Ph | Me |
| 432 | Z6 | 2-Cl-6-F-Ph | Me |
| 433 | Z7 | 2-Cl-6-F-Ph | Me |
| 434 | (2-Me-Z7) | 2-Cl-6-F-Ph | Me |
| 435 | Z8 | 2-Cl-6-F-Ph | Me |
| 436 | (4-Me-Z10) | 2-Cl-6-F-Ph | Me |
| 437 | Z11 | 2-Cl-6-F-Ph | Me |
| 438 | Z12 | 2-Cl-6-F-Ph | Me |
| 439 | (2,6-Me₂-Z12) | 2-Cl-6-F-Ph | Me |
| 440 | Z13 | 2-Cl-6-F-Ph | Me |
| 441 | Z14 | 2-Cl-6-F-Ph | Me |
| 442 | Z15 | 2-Cl-6-F-Ph | Me |
| 443 | Z16 | 2-Cl-6-F-Ph | Me |
| 444 | PhNH | 2-Cl-6-F-Ph | Me |
| 445 | (Ph)(Me)N | 2-Cl-6-F-Ph | Me |
| 446 | (PhCH₂)NH | 2-Cl-6-F-Ph | Me |
| 447 | (PhCH₂)(Me)N | 2-Cl-6-F-Ph | Me |
| 448 | Z5 | 2-Cl-6-F-Ph | Et |
| 449 | (4-Me-Z5) | 2-Cl-6-F-Ph | Et |
| 450 | (2-Me-Z5) | 2-Cl-6-F-Ph | Et |
| 451 | Z7 | 2-Cl-6-F-Ph | Et |
| 452 | Z5 | 2-Cl-6-F-Ph | Pr |
| 453 | (4-Me-Z5) | 2-Cl-6-F-Ph | Pr |
| 454 | (2-Me-Z5) | 2-Cl-6-F-Ph | Pr |
| 455 | Z7 | 2-Cl-6-F-Ph | Pr |
| 456 | Z5 | 2-Cl-6-F-Ph | i-Pr |
| 457 | (4-Me-Z5) | 2-Cl-6-F-Ph | i-Pr |
| 458 | (2-Me-Z5) | 2-Cl-6-F-Ph | i-Pr |
| 459 | Z7 | 2-Cl-6-F-Ph | i-Pr |
| 460 | NH₂ | 2,6-F₂-Ph | Me |
| 461 | MeNH | 2,6-F₂-Ph | Me |
| 462 | EtNH | 2,6-F₂-Ph | Me |
| 463 | i-PrNH | 2,6-F₂-Ph | Me |
| 464 | Me₂N | 2,6-F₂-Ph | Me |
| 465 | Et₂N | 2,6-F₂-Ph | Me |
| 466 | Pr₂N | 2,6-F₂-Ph | Me |
| 467 | Bu₂N | 2,6-F₂-Ph | Me |
| 468 | (i-Bu)₂N | 2,6-F₂-Ph | Me |
| 469 | (CF₃CH₂)NH | 2,6-F₂-Ph | Me |
| 470 | [CF₃CH(Me)]NH | 2,6-F₂-Ph | Me |
| 471 | c-PentNH | 2,6-F₂-Ph | Me |
| 472 | c-HexNH | 2,6-F₂-Ph | Me |
| 473 | (c-Hex)(Me)N | 2,6-F₂-Ph | Me |
| 474 | (CH₂=CHCH₂)NH | 2,6-F₂-Ph | Me |
| 475 | (CH₂=CHCH₂)₂N | 2,6-F₂-Ph | Me |
| 476 | [CH₂=C(Me)CH₂]₂N | 2,6-F₂-Ph | Me |
| 477 | (CH≡CCH₂)NH | 2,6-F₂-Ph | Me |
| 478 | (CH≡CCH₂)₂N | 2,6-F₂-Ph | Me |
| 479 | Z3 | 2,6-F₂-Ph | Me |
| 480 | (2-Me-Z3) | 2,6-F₂-Ph | Me |
| 481 | (2,5-Me₂-Z3) | 2,6-F₂-Ph | Me |
| 482 | Z4 | 2,6-F₂-Ph | Me |
| 483 | Z5 | 2,6-F₂-Ph | Me |
| 484 | (2-Me-Z5) | 2,6-F₂-Ph | Me |
| 485 | (3-Me-Z5) | 2,6-F₂-Ph | Me |
| 486 | (4-Me-Z5) | 2,6-F₂-Ph | Me |
| 487 | (3,3-Me₂-Z5) | 2,6-F₂-Ph | Me |
| 488 | (3,5-Me₂-Z5) | 2,6-F₂-Ph | Me |
| 489 | (2,6-Me₂-Z5) | 2,6-F₂-Ph | Me |
| 490 | Z6 | 2,6-F₂-Ph | Me |

TABLE 1-continued

| Compound No. | R¹R²N | Ar | R³ |
|---|---|---|---|
| 491 | Z7 | 2,6-F$_2$-Ph | Me |
| 492 | (2-Me-Z7) | 2,6-F$_2$-Ph | Me |
| 493 | Z8 | 2,6-F$_2$-Ph | Me |
| 494 | (4-Me-Z10) | 2,6-F$_2$-Ph | Me |
| 495 | Z11 | 2,6-F$_2$-Ph | Me |
| 496 | Z12 | 2,6-F$_2$-Ph | Me |
| 497 | (2,6-Me$_2$-Z12) | 2,6-F$_2$-Ph | Me |
| 498 | Z13 | 2,6-F$_2$-Ph | Me |
| 499 | Z14 | 2,6-F$_2$-Ph | Me |
| 500 | Z15 | 2,6-F$_2$-Ph | Me |
| 501 | Z16 | 2,6-F$_2$-Ph | Me |
| 502 | PhNH | 2,6-F$_2$-Ph | Me |
| 503 | (Ph)(Me)N | 2,6-F$_2$-Ph | Me |
| 504 | (PhCH$_2$)NH | 2,6-F$_2$-Ph | Me |
| 505 | (PhCH$_2$)(Me)N | 2,6-F$_2$-Ph | Me |
| 506 | Z5 | 2,6-F$_2$-Ph | Et |
| 507 | (4-Me-Z5) | 2,6-F$_2$-Ph | Et |
| 508 | (2-Me-Z5) | 2,6-F$_2$-Ph | Et |
| 509 | Z7 | 2,6-F$_2$-Ph | Et |
| 510 | Z5 | 2,6-F$_2$-Ph | Pr |
| 511 | (4-Me-Z5) | 2,6-F$_2$-Ph | Pr |
| 512 | (2-Me-Z5) | 2,6-F$_2$-Ph | Pr |
| 513 | Z7 | 2,6-F$_2$-Ph | Pr |
| 514 | Z5 | 2,6-F$_2$-Ph | i-Pr |
| 515 | (4-Me-Z5) | 2,6-F$_2$-Ph | i-Pr |
| 516 | (2-Me-Z5) | 2,6-F$_2$-Ph | i-Pr |
| 517 | Z7 | 2,6-F$_2$-Ph | i-Pr |
| 518 | Z17 | 2,4,6-F$_3$-Ph | Cl |
| 519 | Z18 | 2,4,6-F$_3$-Ph | Cl |
| 520 | Z19 | 2,4,6-F$_3$-Ph | Cl |
| 521 | Z20 | 2,4,6-F$_3$-Ph | Cl |
| 522 | Z21 | 2,4,6-F$_3$-Ph | Cl |
| 523 | Z22 | 2,4,6-F$_3$-Ph | Cl |
| 524 | Z23 | 2,4,6-F$_3$-Ph | Cl |
| 525 | Z24 | 2,4,6-F$_3$-Ph | Cl |
| 526 | Z25 | 2,4,6-F$_3$-Ph | Cl |
| 527 | Z26 | 2,4,6-F$_3$-Ph | Cl |
| 528 | Z27 | 2,4,6-F$_3$-Ph | Cl |
| 529 | Z28 | 2,4,6-F$_3$-Ph | Cl |
| 530 | Z29 | 2,4,6-F$_3$-Ph | Cl |
| 531 | Z30 | 2,4,6-F$_3$-Ph | Cl |
| 532 | Z31 | 2,4,6-F$_3$-Ph | Cl |
| 533 | (Et)(Me)N | 2,4,6-F$_3$-Ph | Cl |
| 534 | (Pr)(Me)N | 2,4,6-F$_3$-Ph | Cl |
| 535 | (Bu)(Me)N | 2,4,6-F$_3$-Ph | Cl |
| 536 | (CH$_2$=CHCH$_2$)(Me)N | 2,4,6-F$_3$-Ph | Cl |
| 537 | (CH≡CHCH$_2$)(Me)N | 2,4,6-F$_3$-Ph | Cl |
| 538 | Z17 | 2-Cl-6-F-Ph | Cl |
| 539 | Z18 | 2-Cl-6-F-Ph | Cl |
| 540 | Z19 | 2-Cl-6-F-Ph | Cl |
| 541 | Z20 | 2-Cl-6-F-Ph | Cl |
| 542 | Z21 | 2-Cl-6-F-Ph | Cl |
| 543 | Z22 | 2-Cl-6-F-Ph | Cl |
| 544 | Z23 | 2-Cl-6-F-Ph | Cl |
| 545 | Z24 | 2-Cl-6-F-Ph | Cl |
| 546 | Z25 | 2-Cl-6-F-Ph | Cl |
| 547 | Z26 | 2-Cl-6-F-Ph | Cl |
| 548 | Z27 | 2-Cl-6-F-Ph | Cl |
| 549 | Z28 | 2-Cl-6-F-Ph | Cl |
| 550 | Z29 | 2-Cl-6-F-Ph | Cl |
| 551 | Z30 | 2-Cl-6-F-Ph | Cl |
| 552 | Z31 | 2-Cl-6-F-Ph | Cl |
| 553 | (Et)(Me)N | 2-Cl-6-F-Ph | Cl |
| 554 | (Pr)(Me)N | 2-Cl-6-F-Ph | Cl |
| 555 | (Bu)(Me)N | 2-Cl-6-F-Ph | Cl |
| 556 | (CH$_2$=CHCH$_2$)(Me)N | 2-Cl-6-F-Ph | Cl |
| 557 | (CH≡CHCH$_2$)(Me)N | 2-Cl-6-F-Ph | Cl |
| 558 | Z17 | 2,6-F$_2$-Ph | Cl |
| 559 | Z18 | 2,6-F$_2$-Ph | Cl |
| 560 | Z19 | 2,6-F$_2$-Ph | Cl |
| 561 | Z20 | 2,6-F$_2$-Ph | Cl |
| 562 | Z21 | 2,6-F$_2$-Ph | Cl |
| 563 | Z22 | 2,6-F$_2$-Ph | Cl |
| 564 | Z23 | 2,6-F$_2$-Ph | Cl |
| 565 | Z24 | 2,6-F$_2$-Ph | Cl |
| 566 | Z25 | 2,6-F$_2$-Ph | Cl |
| 567 | Z26 | 2,6-F$_2$-Ph | Cl |
| 568 | Z27 | 2,6-F$_2$-Ph | Cl |
| 569 | Z28 | 2,6-F$_2$-Ph | Cl |
| 570 | Z29 | 2,6-F$_2$-Ph | Cl |
| 571 | Z30 | 2,6-F$_2$-Ph | Cl |
| 572 | Z31 | 2,6-F$_2$-Ph | Cl |
| 573 | (Et)(Me)N | 2,6-F$_2$-Ph | Cl |
| 574 | (Pr)(Me)N | 2,6-F$_2$-Ph | Cl |
| 575 | (Bu)(Me)N | 2,6-F$_2$-Ph | Cl |
| 576 | (CH$_2$=CHCH$_2$)(Me)N | 2,6-F$_2$-Ph | Cl |
| 577 | (CH≡CHCH$_2$)(Me)N | 2,6-F$_2$-Ph | Cl |
| 578 | Z17 | 2,4,6-F$_3$-Ph | Me |
| 579 | Z18 | 2,4,6-F$_3$-Ph | Me |
| 580 | Z19 | 2,4,6-F$_3$-Ph | Me |
| 581 | Z20 | 2,4,6-F$_3$-Ph | Me |
| 582 | Z21 | 2,4,6-F$_3$-Ph | Me |
| 583 | Z22 | 2,4,6-F$_3$-Ph | Me |
| 584 | Z23 | 2,4,6-F$_3$-Ph | Me |
| 585 | Z24 | 2,4,6-F$_3$-Ph | Me |
| 586 | Z25 | 2,4,6-F$_3$-Ph | Me |
| 587 | Z26 | 2,4,6-F$_3$-Ph | Me |
| 588 | Z27 | 2,4,6-F$_3$-Ph | Me |
| 589 | Z28 | 2,4,6-F$_3$-Ph | Me |
| 590 | Z29 | 2,4,6-F$_3$-Ph | Me |
| 591 | Z30 | 2,4,6-F$_3$-Ph | Me |
| 592 | Z31 | 2,4,6-F$_3$-Ph | Me |
| 593 | (Et)(Me)N | 2,4,6-F$_3$-Ph | Me |
| 594 | (Pr)(Me)N | 2,4,6-F$_3$-Ph | Me |
| 595 | (Bu)(Me)N | 2,4,6-F$_3$-Ph | Me |
| 596 | (CH$_2$=CHCH$_2$)(Me)N | 2,4,6-F$_3$-Ph | Me |
| 597 | (CH≡CHCH$_2$)(Me)N | 2,4,6-F$_3$-Ph | Me |
| 598 | Z17 | 2-Cl-6-F-Ph | Me |
| 599 | Z18 | 2-Cl-6-F-Ph | Me |
| 600 | Z19 | 2-Cl-6-F-Ph | Me |
| 601 | Z20 | 2-Cl-6-F-Ph | Me |
| 602 | Z21 | 2-Cl-6-F-Ph | Me |
| 603 | Z22 | 2-Cl-6-F-Ph | Me |
| 604 | Z23 | 2-Cl-6-F-Ph | Me |
| 605 | Z24 | 2-Cl-6-F-Ph | Me |
| 606 | Z25 | 2-Cl-6-F-Ph | Me |
| 607 | Z26 | 2-Cl-6-F-Ph | Me |
| 608 | Z27 | 2-Cl-6-F-Ph | Me |
| 609 | Z28 | 2-Cl-6-F-Ph | Me |
| 610 | Z29 | 2-Cl-6-F-Ph | Me |
| 611 | Z30 | 2-Cl-6-F-Ph | Me |
| 612 | Z31 | 2-Cl-6-F-Ph | Me |
| 613 | (Et)(Me)N | 2-Cl-6-F-Ph | Me |
| 614 | (Pr)(Me)N | 2-Cl-6-F-Ph | Me |
| 615 | (Bu)(Me)N | 2-Cl-6-F-Ph | Me |
| 616 | (CH$_2$=CHCH$_2$)(Me)N | 2-Cl-6-F-Ph | Me |
| 617 | (CH≡CHCH$_2$)(Me)N | 2-Cl-6-F-Ph | Me |
| 618 | Z17 | 2,6-F$_2$-Ph | Me |

TABLE 1-continued

| Compound No. | R¹R²N | Ar | R³ |
|---|---|---|---|
| 619 | Z18 | 2,6-F$_2$-Ph | Me |
| 620 | Z19 | 2,6-F$_2$-Ph | Me |
| 621 | Z20 | 2,6-F$_2$-Ph | Me |
| 622 | Z21 | 2,6-F$_2$-Ph | Me |
| 623 | Z22 | 2,6-F$_2$-Ph | Me |
| 624 | Z23 | 2,6-F$_2$-Ph | Me |
| 625 | Z24 | 2,6-F$_2$-Ph | Me |
| 626 | Z25 | 2,6-F$_2$-Ph | Me |
| 627 | Z26 | 2,6-F$_2$-Ph | Me |
| 628 | Z27 | 2,6-F$_2$-Ph | Me |
| 629 | Z28 | 2,6-F$_2$-Ph | Me |
| 630 | Z29 | 2,6-F$_2$-Ph | Me |
| 631 | Z30 | 2,6-F$_2$-Ph | Me |
| 632 | Z31 | 2,6-F$_2$-Ph | Me |
| 633 | (Et)(Me)N | 2,6-F$_2$-Ph | Me |
| 634 | (Pr)(Me)N | 2,6-F$_2$-Ph | Me |
| 635 | (Bu)(Me)N | 2,6-F$_2$-Ph | Me |
| 636 | (CH$_2$=CHCH$_2$)(Me)N | 2,6-F$_2$-Ph | Me |
| 637 | (CH≡CHCH$_2$)(Me)N | 2,6-F$_2$-Ph | Me |

In the above table, Me, Et, i-Pr, Bu, t-Bu, i-Bu, c-Pr, c-Bu, c-Pent, c-Hex, c-Hep, c-Oct, Ac, Ph and Cyano represents methyl, ethyl, isopropyl, butyl, tert-butyl, isobutyl, cyclopropyl, cyclobutyl, cyclopentyl, cyclohexyl, cycloheptyl, cyclooctyl, acetyl, phenyl and cyano groups, respectively.

Further, Z1, Z2, Z3, Z4, Z5, Z6, Z7, Z8, Z9, Z10, Z11, Z12, Z13, Z14, Z15, Z16, Z17, Z18, Z19, Z20, Z21, Z22, Z23, Z24, Z25, Z26, Z27, Z28, Z29, Z30 and Z31 mean the following groups:

(Z1)

(Z2)

(Z3)

(Z4)

(Z5)

(Z6)

(Z7) 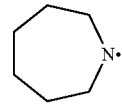

(Z8) 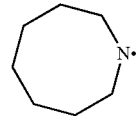

(Z9) 

(Z10) 

(Z11) 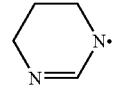

(Z12) 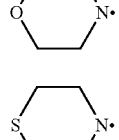

(Z13) 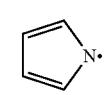

(Z14) 

(Z15) 

(Z16) 

(Z17) 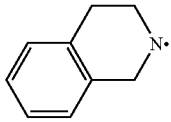

(Z18) 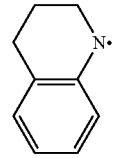

(Z19) 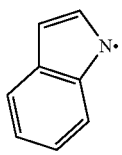

-continued (Z20) 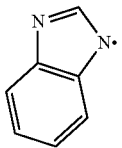

(Z21) 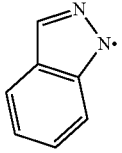

(Z22) 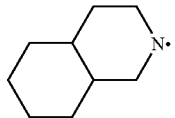

(Z23) 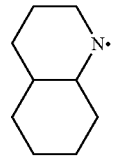

(Z24) 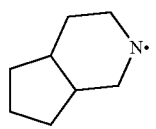

(Z25) 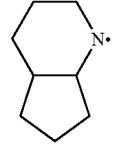

(Z26) 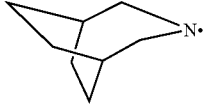

(Z27) 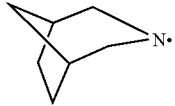

(Z28) 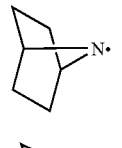

(Z29) 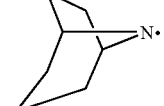

(Z30) 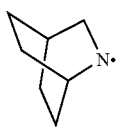

-continued (Z31) 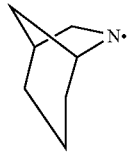

The physical properties of some of the present compounds are given below:

Compound 1
$^1$H-NMR δ(ppm; TMS): (DMSO-d$_6$) 7.38 (2H, dd, J=7.6, 9.2), 7.58 (1H, d, J=1.6), 7.93 (2H, brs), 7.98 (1H, d, J=1.6)

Compound 4
$^1$H-NMR δ(ppm; TMS): (CDCl$_3$) 1.21 (6H, d, J=6.4 Hz), 3.6–3.8 (1H, m), 5.19 (1H, brs), 6.86 (2H, t, J=8.5 Hz), 7.71 (1H, d, J=1 Hz), 7.89 (1H, d, J=1 Hz)

Compound 7
mp: 137.8° C. $^1$H-NMR δ (ppm; TMS): (CDCl$_3$) 1.10 (6H, t, J=7.1 Hz), 3.11 (4H, q, J=7.1 Hz), 6.8–6.9 (2H, m), 7.47 (1H, d, J=1.4 Hz), 7.76 (1H, d, J=1.4 Hz)

Compound 8
mp: 95.4° C. $^1$H-NMR δ (ppm; TMS): (CDCl$_3$) 0.83 (6H, t, J=7 Hz), 1.4–1.6 (4H, m), 2.9–3.0 (4H, m), 6.84 (2H, dd, J=7.1 Hz,8.5 Hz), 7.48 (1H, d, J=1.3 Hz), 7.76 (1, H, d, J=1.3 Hz)

Compound 9
$^1$H-NMR δ (ppm; TMS): (CDCl$_3$) 0.86 (6H, t, J=7.4 Hz), 1.1–1.3 (4H, m), 1.4–1.5 (4H, m), 2.9–3.0 (4H, m), 6.84. (2H, dd, J=7.1 Hz,8.6 Hz), 7.46 (1H, d, J=1.4 Hz), 7.74 (1H, d, J=1.4 Hz)

Compound 20
$^1$H-NMR δ (ppm; TMS): (CDCl$_3$) 1.0–2.0 (10H, m), 3.28 (1H, brs), 5.23 (1H, brs), 6.87 (2H, dd, J=6.9 Hz,8.5 Hz), 7.70 (1H, d, J=1 Hz), 7.83 (1H, d, J=1 Hz)

Compound 21
$^1$H-NMR δ (ppm; TMS): (CDCl$_3$) 0.9–1.3 (3H, m), 1.4–1.7 (6H, m), 2.72 (3H, s), 3.0–3.2 (1H, m), 6.8–6.9 (2H, m), 7.41 (1H, d, J=1 Hz), 7.76 (1H, d, J=1 Hz)

Compound 29
$^1$H-NMR δ (ppm; TMS): (CDCl$_3$) 3.62 (4H, d, J=6.0 Hz), 5.1–5.3 (4H, m), 5.5–5.7 (2H, m), 6.85 (2H, dd, J=7.0 Hz,8.5 Hz), 7.51 (1H, d, J=1.4 Hz), 7.76 (1H, d, J=1.4 Hz)

Compound 48
$^1$H-NMR δ (ppm; TMS): (CDCl$_3$) 1.8–2.0 (4H, m), 3.2–3.3 (4H, m), 6.81 (2H, dd, J=7.0 Hz,8.4 Hz), 7.53 (1H, d, J=1.4 Hz), 7.69 (1H, d, J=1.7 Hz)

Compound 49
$^1$H-NMR δ (ppm; TMS): (CDCl$_3$) 0.98 (3H, d, J=6.0 Hz), 14–1.6 (1H, m), 1.7–1.9 (1H, m), 1.9–2.2 (2H, m), 3.1–3.3 (1H.m), 3.4–3.6 (2H, m), 6.7–6.9 (2H, m), 7.51 (1H, d, J=1.4 Hz), 7.71 (1H, d, J=1.7 Hz)

Compound 50
$^1$H-NMR δ (ppm; TMS): (CDCl$_3$) 1.05 (6H, d, J=6.3 Hz), 1.5–1.7 (2H, m), 1.7–1.9 (2H, m), 3.2–3.4 (2H.m), 6.8–6.9 (2H, m), 7.72 (1H, d, J=1.4 Hz), 7.92 (1H, d, J=1.4 Hz)

Compound 52 mp: 174.4° C. $^1$H-NMR δ (ppm; TMS): (CDCl$_3$) 1.61 (6H, brs), 2.92 (4H, brs), 6.8–6.9 (2H, m), 7.39 (1H, s), 7.74 (1H, s)

Compound 53

$^1$H-NMR δ (ppm; TMS): (CDCl$_3$) 1.03 (3H, d, J=6.5 Hz),1.2–1.8 (6H, m),2.97–3.4 (3H, m), 6.8–6.9 (2H, m),7.53 (1H, br),7.74 (1H, d, J=1.4 Hz)

Compound 54

$^1$H-NMR δ (ppm; TMS): (CDCl$_3$) 0.86 (3H, d, J=6.63 Hz), 1.1–1.3 (2H, m), 1.4–1.6 (1H, m), 1.6–1.7 (2H, m), 2.5–2.7 (2H, m), 3.2–3.4 (2H, m), 7.04 (2H, dd, J=7.3 Hz, 8.5 Hz), 7.40 (1H, d, J=1.2 Hz), 7.74 (1H, d, J=1.4 Hz)

Compound 55 mp: 200.8° C. $^1$H-NMR δ (ppm; TMS): (CDCl$_3$) 0.99 (3H, d, J=6.4 Hz), 1.1–1.4 (2H, m), 1.4–1.6 (1H, m), 1.6–1.8 (2H, m), 2.5–2.7 (2H, m), 3.2–3.4 (2H, m), 6.85 (2H, dd, J=7.1 Hz,8.4 Hz), 7.40 (1H, d, J=1.7 Hz), 7.77 (1H, d, J=1.7 Hz)

Compound 63

$^1$H-NMR δ (ppm; TMS): (CDCl$_3$) 0.6–0.8 (2H, m), 0.82 (6H, d, J=6.6 Hz), 1.7–1.9 (2H, m), 2.0–2.3 (2H, m), 3.2–3.3 (2H, m), 6.85 (2H, dd, J=7.2 Hz,8.3 Hz), 7.37 (1H, d, J=1 Hz), 7.74 (1H, d, J=1 Hz)

Compound 65

$^1$H-NMR δ (ppm; TMS): (CDCl$_3$) 0.72 (3H, t, J=7.2 Hz), 1.0–1.8 (8H, m), 3.0–3.4 (3H, m), 6.8–6.9 (2H, m), 7.48 (1H, brs), 7.73 (1H, d, J=1.4 Hz)

Compound 67

$^1$H-NMR δ (ppm; TMS): (CDCl$_3$) 1.4–1.9 (2H, m), 1.9–2.0 (2H, m), 2.6–3.0 (2H, m), 3.1–3.4 (2H, m), 3.7–4.1 (1H, m), 6.85, (1H, dd, J=7.0 Hz, 8.2 Hz), 7.39 (1H, d,=1.4 Hz), 7.76 (1H, d, J=1.4 Hz)

Compound 71

$^1$H-NMR δ (ppm; TMS): (CDCl$_3$) 2.1–2.4 (2H, m), 3.0–3.3 (2H, m), 3.4–3.7 (2H, m), 5.6–5.7 (1H, m), 5.8–5.9 (1H, m), 6.8–6.9 (2H, m), 7.41 (1H, d, J=1.4 Hz), 7.75 (1H, d, J=1.4 Hz)

Compound 72 mp: 143.8° C. $^1$H-NMR δ (ppm; TMS): (CDCl$_3$) 1.6–1.8 (8H, m), 3.1–3.2 (4H, m), 6.85 (2H, dd, J=6.8 Hz, 8.6 Hz), 7.52 (1H, d, J=1 Hz), 7.75 (1H, d, J=1 Hz)

Compound 73

$^1$H-NMR δ (ppm; TMS): (CDCl$_3$) 1.5–1.7 (10H, m), 3.1–3.2 (4H, m), 6.8–6.9 (2H, m), 7.58 (1H, d, J=1 Hz), 7.77 (1H, d, J=1 Hz)

Compound 76

$^1$H-NMR δ (ppm; TMS): (CDCl$_3$) 2.38 (3H, s), 2.57 (4H, brs), 3.07 (4H, brs), 6.85 (2H, dd, J=7.1 Hz,8.4 Hz), 7.44 (1H, d, J=1 Hz), 7.77 (1H, d, J=1 Hz)

Compound 81 mp: 185.4° C. $^1$H-NMR δ (ppm; TMS): (CDCl$_3$) 3.01 (4H, brs), 3.77 (4H, t, J=4.6), 6.88 (2H, dd, J=7.1 Hz,8.5 Hz), 7.45 (1H, d, J=1.4 Hz), 7.79 (1H, d, J=1.4 Hz)

Compound 83 mp: 201.7° C. $^1$H-NMR δ (ppm; TMS): (CDCl$_3$) 2.68 (4H, brs), 3.23 (4H, brs), 6.8–6.9 (2H, m), 7.45 (1H, d, J=1.4 Hz), 7.80 (1H, d, J=1.4 Hz)

Compound 85

$^1$H-NMR δ (ppm; TMS): (CDCl$_3$) 6.44 (1H, t, J=2.4 Hz), 6.76 (2H, dd, J=7.1 Hz,8.5 Hz), 7.43 (1H, d, J=2.6 Hz), 7.72 (1H, d, J=1.6 Hz), 7.85 (1H, d, J=2.6 Hz), 7.86 (1H, d, J=1.6 Hz)

Compound 89 mp: 150.4° C. $^1$H-NMR δ (ppm; TMS): (CDCl$_3$) 1.94 (3H, s), 2.20 (3H, s), 5.98 (1H, s), 6.7–6.8 (2H, m), 7.19 (1H, d, J=1.6 Hz), 7.84 (1H, d, J=1.6 Hz)

Compound 90

$^1$H-NMR δ (ppm; TMS): (CDCl$_3$) 6.73 (2H, t, J=7.8 Hz),7.02 (1H, d, J=1.4 Hz), 7.12 (1H, s), 7.92 (1H, d, J=1.4 Hz)

Compound 106

$^1$H-NMR δ (ppm; TMS): (DMSO-d$_6$) 4.28 (2H, d, J=6.6Hz), 6.8–7.0 (2H, m), 7.07 (2H, dd, J=7.5 Hz,9.1 Hz), 7.68 (1H, d,J=1.5 Hz), 8.19 (1H, d, J=1.5 Hz), 8.4–8.5 (1H, d,m)

Compound 109

$^1$H-NMR δ (ppm; TMS): (CDCl$_3$) 2.69 (3H, s), 3.97 (2H, s), 6.87 (2H, dd, J=7.3 Hz,8.4 Hz), 7.2–7.3 (2H, m), 7.3–7.4 (3H, m), 7.48 (1H, d, J=1 Hz), 7.75 (1H, s)

Compound 159

$^1$H-NMR δ (ppm; TMS): (CDCl$_3$) 1.17 (6H, t, J=5.5 Hz), 3.6–3.8 (1H, m), 4.74 (1H, brd, J=8.7), 7.1–7.2 (m,1H), 7.3–7.5 (2H, m), 7.72 (2H, s)

Compound 161

$^1$H-NMR δ (ppm; TMS): (CDCl$_3$) 1.10 (6H, t, J=7.1 Hz), 3.0–3.2 (4H, m), 7.1–7.2 (1H, m), 7.3–7.5 (2H, m), 7.47 (1H, d, J=1.4 Hz), 7.76 (1H, d, J=1.4 Hz)

Compound 175

$^1$H-NMR δ (ppm; TMS): (CDCl$_3$) 1.8–1.9 (4H, m), 3.2–3.3 (4H, m), 7.1–7.2 (m,1H), 7.3–7.5 (m,2H), 7.58 (1H, d, J=1.5 Hz), 7.71 (1H, d, J=1.5 Hz)

Compound 180

$^1$H-NMR δ (ppm; TMS): (CDCl$_3$) 1.0–1.8 (9H, m), 2.8–3.4 (3H, m), 7.1–7.2 (1H, m), 7.3–7.7 (3H, m), 7.73 (1H, s)

Compound 182 mp: 183.8° C. $^1$H-NMR δ (ppm; TMS): (CDCl$_3$) 0.96 (3H, d, J=6.5 Hz), 1.1–1.3 (2H, m), 1.4–1.6 (1H, m), 1.6–1.7 (2H, m), 2.5–2.7 (2H, m), 3.2–3.4 (2H, m), 7.1–7.2 (1H, m), 7.3–7.5 (2H, m), 7.40 (1H, d, J=1 Hz), 7.78 (1H, d, J=1 Hz)

Compound 187

$^1$H-NMR δ (ppm; TMS): (CDCl$_3$) 1.5–1.7 (8H, m), 3.1–3.2 (4H, m), 7.16 (1H, dt, J=1.4 Hz, 8.2 Hz), 7.3–7.5 (2H, m), 7.51 (1H, d, J=1.4 Hz), 7.74 (1H, d, J=1.7 Hz)

Compound 226

$^1$H-NMR δ (ppm; TMS): (CDCl$_3$) 1.04 (3H, d, J=6.4 Hz), 1.2–1.7 (6H, m), 2.7–3.4 (3H, m), 7.0–7.1 (2H, m), 7.4–7.6 (2H, m), 7.74 (1H, d, J=1.4 Hz)

Compound 228

$^1$H-NMR δ (ppm; TMS): (CDCl$_3$) 0.96 (3H, d, J=6.3 Hz), 1.1–1.3 (2H, m), 1.4–1.6 (1H, m), 1.6–1.7 (2H, m), 2.5–2.7 (2H, m), 3.2–3.3 (2H, m), 7.04 (2H, dd, J=7.0 Hz, 8.5 Hz), 7.38 (1H, d, J=1.4 Hz), 7.4–7.5 (1H, m), 7.74 (1H, d, J=1.4 Hz)

Compound 233
¹H-NMR δ (ppm; TMS): (CDCl₃) 1.5–1.8 (8H, m), 3.0–3.2 (4H, m), 6.99 (2H, dd, J=7.0 Hz,8.5 Hz), 7.4–7.6 (1H, m), 7.51 (1H, d, J=1.7 Hz), 7.74 (1H, d, J=1.4 Hz)

Compound 249
¹H-NMR δ (ppm; TMS): (CDCl₃) 0.94 (3H, d, J=6.4 Hz), 1.1–1.3 (2H, m), 1.3–1.5 (1H, m), 1.6–1.7 (2H, m), 2.2–2.5 (2H, m), 3.1–3.3 (2H, m), 7.2–7.3 (2H, m), 7.43 (1H, d, J=1 Hz), 7.4–7.6 (3H, m), 7.74 (1H, d, J=1 Hz)

Compound 250
¹H-NMR δ (ppm; TMS): (CDCl₃) 0.8–1.8 (9H, m), 2.1–2.5 (1H, m), 2.7–2.9 (1H, m), 3.1–3.4 (1H, m), 7.2–7.3 (1H, m), 7.3–7.7 (5H, m), 7.73 (1H, s)

Compound 251
¹H-NMR δ (ppm; TMS): (CDCl₃) 1.5–1.7 (8H, m), 2.9–3.1 (4H, m), 7.2–7.3 (2H, m), 7.4–7.6 (4H, m), 7.73 (1H, d, J=1.2 Hz)

Compound 253
¹H-NMR δ (ppm; TMS): (CDCl₃) 0.94 (3H, d, J=6.3 Hz), 1.1–1.5 (3H, m), 1.5–1.7 (2H, m), 2.3–2.6 (2H, m), 3.1–3.4 (2H, m), 7.2–7.3 (1H, m), 7.3–7.5 (3H, m), 7.5–7.6 (1H, m), 7.73 (1H, d, J=1.4 Hz)

Compound 255
¹H-NMR δ (ppm; TMS): (CDCl₃) 1.5–1.8 (8H, m), 3.0–3.2 (4H, m), 7.23 (1H, dd, J=1.9 Hz, 7.2 Hz), 7.3–7.5 (2H, m), 7.51 (1H, d, J=1.4 Hz), 7.55 (1H, dd, J=1.7 Hz, 7.5 Hz), 7.73 (1H, d, J=1.4 Hz)

Compound 257
¹H-NMR δ (ppm; TMS): (CDCl₃) 0.95 (3H, d, J=6.5 Hz), 1.1–1.4 (2H, m), 1.4–1.7 (3H, m), 2.3–2.6 (2H, m), 3.1–3.4 (2H, m), 7.2–7.3 (3H, m), 7.38 (1H, d, J=1.4 Hz), 7.4–7.5 (1H, m), 7.73 (1H, d, J=1.4 Hz)

Compound 258
¹H-NMR δ (ppm; TMS): (CDCl₃) 1.0–1.2 (3H, m), 1.3–1.8 (4H, m), 2.3–2.8 (2H, m), 2.8–3.5 (3H, m), 7.2–7.6 (5H, m), 7.73 (1H, d, J=1.4 Hz)

Compound 259
¹H-NMR δ (ppm; TMS): (CDCl₃) 1.5–1.8 (8H, m), 3.0–3.1 (4H, m), 7.2–7.4 (3H, m), 7.4–7.6 (2H, m), 7.73 (1H, d, J=1.2 Hz)

Compound 261
¹H-NMR δ (ppm; TMS): (CDCl₃) 0.92 (3H, d, J=6.3 Hz), 1.1–1.5 (3H, m), 1.5–1.7 (2H, m), 2.1–2.3 (1H, m), 2.21 (3H, s), 2.5–2.6 (1H, m), 2.8–3.0 (1H, m), 3.3–3.5 (1H, m), 7.03 (1H, d, J=7.5 Hz), 7.2–7.4 (4H, m), 7.73 (1H, d, J=1.4 Hz)

Compound 263
¹H-NMR δ (ppm; TMS): (CDCl₃) 1.4–1.7 (8H, m), 2.9–3.1 (4H, m), 7.04 (1H, dd, J=1.1 Hz,7.5 Hz), 7.2–7.4 (3H, m), 7.51 (1H, d, J=1.4 Hz), 7.74 (1H, d, J=1.4 Hz)

Compound 265
¹H-NMR δ (ppm; TMS): (CDCl₃) 0.93 (3H, d, J=6.5 Hz), 1.1–1.3 (2H, m), 1.3–1.5 (2H, m), 1.5–1.7 (2H, m), 2.2–2.6 (2H, m), 3.2–3.4 (2H, m), 7.3–7.4 (2H, m), 7.6–7.7 (2H, m), 7.7–7.9 (2H, m)

Compound 267
¹H-NMR δ (ppm; TMS): (CDCl₃) 1.4–1.7 (8H, m), 3.0–3.2 (4H, m), 7.31 (1H, d, J=7.5 Hz), 7.49 (1H, d, J=1.4 Hz), 7.6–7.7 (2H, m), 7.73 (1H, d, J=1.7 Hz), 7.82 (1H, d, J=7.5 Hz)

Compound 281
¹H-NMR δ (ppm; TMS): (CDCl₃) 0.95 (3H, d, J=6.5 Hz), 1.1–1.3 (2H, m), 1.3–1.5 (1H, m), 1.6–1.7 (2H, m), 2.3–2.5 (2H, m), 3.1–3.3 (2H, m), 7.1–7.3 (4H, m), 7.37 (1H, d, J=1 Hz), 7.72 (1H, d, J=1H)

Compound 282
¹H-NMR δ (ppm; TMS): (CDCl₃) 0.8–1.1 (3H, m), 1.2–1.8 (6H, m), 2.2–2.8 (2H, m), 3.1–3.5 (1H, m), 7.1–7.7 (5H, m), 7.74 (1H, d, J=1.4 Hz)

Compound 283
¹H-NMR δ (ppm; TMS): (CDCl₃) 1.5–1.7 (8H, m), 2.9–3.1 (4H, m), 7.1–7.3 (4H, m), 7.51 (1H, d, J=1.4 Hz), 7.73 (1H, d, J=1.4 Hz)

Compound 285
¹H-NMR δ (ppm; TMS): (CDCl₃) 0.96 (3H, d, J=6.2 Hz), 1.1–1.4 (2H, m), 1.4–1.6 (1H, m), 1.6–1.7 (2H, m), 2.5–2.7 (2H, m), 3.3–3.4 (2H, m), 7.3–7.4 (2H, m), 7.4–7.6 (2H, m), 7.74 (1H, d, J=1 Hz)

Compound 286
¹H-NMR δ (ppm; TMS): (CDCl₃) 1.17 (3H, d, J=6.7 Hz), 1.2–1.7 (6H, m), 3.0–3.7 (3H, m), 7.3–7.4 (1H, m), 7.4–7.6 (3H, m), 7.71 (1H, s)

Compound 287
¹H-NMR δ (ppm; TMS): (CDCl₃) 1.5–1.7 (8H, m), 3.1–3.3 (4H, m), 7.3–7.4 (1H, m), 7.4–7.5 (2H, m), 7.51 (1H, d, J=1.4 Hz), 7.74 (1H, d, J=1.4 Hz)

Compound 293
¹H-NMR δ (ppm; TMS): (CDCl₃) 0.97 (3H, d, J=6.3 Hz), 1.2–1.4 (2H, m), 1.4–1.6 (1H, m), 1.6–1.7 (2H, m), 2.4–2.6 (2H, m), 3.1–3.4 (2H, m), 6.9–7.1 (2H, m), 7.1–7.3 (1H, m), 7.38 (1H, d, J=1.4 Hz), 7.74 (1H, d, J=1.4 Hz)

Compound 295
¹H-NMR δ (ppm; TMS): (CDCl₃) 1.5–1.8 (8H, m), 3.0–3.1 (4H, m), 6.9–7.1 (2H, m), 7.1–7.3 (1H, m), 7.51 (1H, d, J=1.4 Hz), 7.74 (1H, d, J=1.7 Hz)

Compound 297
¹H-NMR δ (ppm; TMS): (CDCl₃) 0.98 (3H, d, J=6.3 Hz),1.2–1.4 (2H, m), 1.4–1.8 (3H, m), 2.4–2.6 (2H, m), 3.2–3.3 (2H, m), 7.18 (2H, s), 7.4–7.5 (2H, m), 7.74 (1H, d, J=0.7 Hz)

Compound 299
¹H-NMR δ (ppm; TMS): (CDCl₃) 1.5–1.8 (8H, m), 3.0–3.1 (4H, m), 7.20 (2H, d, J=1.4 Hz), 7.4–7.5 (1H, m), 7.51 (1H, d, J=1.2 Hz), 7.75 (1H, d, J=1.2 Hz)

Compound 428
mp: 144.5° C. ¹H-NMR δ (ppm; TMS): (CDCl₃) 0.95 (3H, d, J=6.3 Hz), 1.1–1.3 (2H, m), 1.3–1.5 (1H, m), 1.6–1.7 (2H, m), 2.29 (3H, s), 2.4–2.6 (2H, m), 3.2–3.3 (2H, m), 7.1–7.2 (1H, m), 7.3–7.5 (3H, m), 7.76 (1H, d, J=2 Hz)

Compound 449
¹H-NMR δ (ppm; TMS): (CDCl₃) 0.94 (3H, m), 1.20 (3H, t, J=7 Hz), 1.2–1.4 (2H, m), 1.4–1.5 (1H, m), 1.6–1.7 (2H, m), 2.3–2.6 (4H, m), 3.2–3.3 (2H, m), 7.1–7.2 (1H, m), 7.3–7.5 (3H, m), 7.71 (1H, d, J=1.6 Hz)

Compound 518
¹H-NMR δ (ppm; TMS): (CDCl₃) 2.8–3.0 (2H, m), 3.2–3.3 (2H, m), 4.2–4.4 (2H, m), 6.73 (2H, dd, J=7.7 Hz,8.2 Hz), 6.87 (1H, d, J=7.2 Hz), 7.1–7.3 (3H, m), 7.40 (1H, d, J=1 Hz), 7.74 (1H, d, J=1 Hz)

Compound 521

¹H-NMR δ (ppm; TMS): (CDCl₃) 6.5–6.6 (1H, m), 6.7–6.8 (1H, m), 7.06 (1H, d, J=8.3 Hz), 7.12 (1H, d, J=1.5 Hz), 7.3–7.5 (2H, m), 7.8–7.9 (3H, m)

Compound 535

¹H-NMR δ (ppm; TMS): (CDCl₃) 0.86 (3H, d, J=7.3 Hz), 1.2–1.3 (2H, m), 1.4–1.6 (2H, m), 2.7–2.9 (5H, m), 6.84 (2H, dd, J=7.2 Hz,8.5 Hz), 7.44 (1H, d, J=1.4 Hz), 7.74 (1H, d, J=1.4 Hz)

Compound 537

¹H-NMR δ (ppm; TMS): (CDCl₃) 2.41 (1H, t, J=2.4 Hz), 2.75 (3H, s), 3.81 (2H, d, J=2.4 Hz), 6.84 (2H, dd,=7.4 Hz,8.3 Hz), 7.64 (1H, d, J=1.4 Hz), 7.78 (1H, d, J=1.2 Hz)

Further, production intermediates, imidazo[1,2-a]pyrimidine [II], imidazo[1,2-a]pyrimidine [III] and imidazo[1,2-a]pyrimidine [IV] are shown with their compound numbers below.

Compound given by the following formula:

TABLE 2

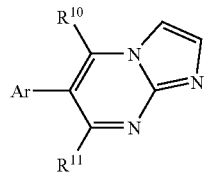

| Compound No. | Ar | $R^{10}$ | $R^{11}$ |
| --- | --- | --- | --- |
| 2-1 | 2,4,6-F₃—Ph | Cl | Cl |
| 2-2 | 2-Cl-6-F—Ph | Cl | Cl |
| 2-3 | 2,6-F₂—Ph | Cl | Cl |
| 2-4 | Ph | Cl | Cl |
| 2-5 | 2-Cl—Ph | Cl | Cl |
| 2-6 | 2-F—Ph | Cl | Cl |
| 2-7 | 2-Me—Ph | Cl | Cl |
| 2-8 | 2-CF₃—Ph | Cl | Cl |
| 2-9 | 3-Cl—Ph | Cl | Cl |
| 2-10 | 3-F—Ph | Cl | Cl |
| 2-11 | 4-Cl—Ph | Cl | Cl |
| 2-12 | 4-F—Ph | Cl | Cl |
| 2-13 | 2,6-Cl₂—Ph | Cl | Cl |
| 2-14 | 2,4-Cl₂—Ph | Cl | Cl |
| 2-15 | 2,4-F₂—Ph | Cl | Cl |
| 2-16 | 3,5-Cl₂—Ph | Cl | Cl |
| 2-17 | 3,5-F₂—Ph | Cl | Cl |
| 2-18 | 2,4,6-Cl₃—Ph | Cl | Cl |
| 2-19 | 2,6-Cl₂-4-F—Ph | Cl | Cl |
| 2-20 | 2,4-Cl₂-6-F—Ph | Cl | Cl |
| 2-21 | 2-Cl-4,6-F₂—Ph | Cl | Cl |
| 2-22 | 4-Cl-2,6-F₂—Ph | Cl | Cl |
| 2-23 | 2,6-F₂-4-(MeO)—Ph | Cl | Cl |
| 2-24 | 2,3,6-F₃—Ph | Cl | Cl |
| 2-25 | 2,3,4,5,6-F₅—Ph | Cl | Cl |
| 2-26 | 3-F-6-CF₃—Ph | Cl | Cl |
| 2-27 | 2,4,6-Me₃—Ph | Cl | Cl |
| 2-28 | 2,4,6-F₃—Ph | Cl | Me |
| 2-29 | 2,4,6-F₃—Ph | Cl | Et |
| 2-30 | 2,4,6-F₃—Ph | Cl | Pr |
| 2-31 | 2,4,6-F₃—Ph | Cl | i-Pr |
| 2-32 | 2-Cl-6-F—Ph | Cl | Me |
| 2-33 | 2-Cl-6-F—Ph | Cl | Et |
| 2-34 | 2-Cl-6-F—Ph | Cl | Pr |
| 2-35 | 2-Cl-6-F—Ph | Cl | i-Pr |
| 2-36 | 2,6-F₂—Ph | Cl | Me |
| 2-37 | 2,6-F₂—Ph | Cl | Et |
| 2-38 | 2,6-F₂—Ph | Cl | Pr |
| 2-39 | 2,6-F₂—Ph | Cl | i-Pr |
| 3-1 | 2,4,6-F₃—Ph | OH | OH |
| 3-2 | 2-Cl-6-F—Ph | OH | OH |
| 3-3 | 2,6-F₂—Ph | OH | OH |
| 3-4 | Ph | OH | OH |
| 3-5 | 2-Cl—Ph | OH | OH |
| 3-6 | 2-F—Ph | OH | OH |
| 3-7 | 2-Me—Ph | OH | OH |
| 3-8 | 2-CF₃—Ph | OH | OH |
| 3-9 | 3-Cl—Ph | OH | OH |
| 3-10 | 3-F—Ph | OH | OH |
| 3-11 | 4-Cl—Ph | OH | OH |
| 3-12 | 4-F—Ph | OH | OH |
| 3-13 | 2,6-Cl₂—Ph | OH | OH |
| 3-14 | 2,4-Cl₂—Ph | OH | OH |
| 3-15 | 2,4-F₂—Ph | OH | OH |
| 3-16 | 3,5-Cl₂—Ph | OH | OH |
| 3-17 | 3,5-F₂—Ph | OH | OH |
| 3-18 | 2,4,6-Cl₃—Ph | OH | OH |
| 3-19 | 2,6-Cl₂-4-F—Ph | OH | OH |
| 3-20 | 2,4-Cl₂-6-F—Ph | OH | OH |
| 3-21 | 2-Cl-4,6-F₂—Ph | OH | OH |
| 3-22 | 4-Cl-2,6-F₂—Ph | OH | OH |
| 3-23 | 2,6-F₂-4-(MeO)—Ph | OH | OH |
| 3-24 | 2,3,6-F₃—Ph | OH | OH |
| 3-25 | 2,3,4,5,6-F₅—Ph | OH | OH |
| 3-26 | 3-F-6-CF₃—Ph | OH | OH |
| 3-27 | 2,4,6-Me₃—Ph | OH | OH |
| 4-1 | 2,4,6-F₃—Ph | OH | Me |
| 4-2 | 2,4,6-F₃—Ph | OH | Et |
| 4-3 | 2,4,6-F₃—Ph | OH | Pr |
| 4-4 | 2,4,6-F₃—Ph | OH | i-Pr |
| 4-5 | 2-Cl-6-F—Ph | OH | Me |
| 4-6 | 2-Cl-6-F—Ph | OH | Et |
| 4-7 | 2-Cl-6-F—Ph | OH | Pr |
| 4-8 | 2-Cl-6-F—Ph | OH | i-Pr |
| 4-9 | 2,6-F₂—Ph | OH | Me |
| 4-10 | 2,6-F₂—Ph | OH | Et |
| 4-11 | 2,6-F₂—Ph | OH | Pr |
| 4-12 | 2,6-F₂—Ph | OH | i-Pr |

The physical properties of some of the production intermediates, imidazo[1,2-a]pyrimidine [II], imidazo[1,2-a]pyrimidine [III] and imidazo[1,2-a]pyrimidine [IV] are given below:

Compound 2-1 mp: 192.56° C. ¹H-NMR δ (ppm; TMS): (CDCl₃) 6.88 (2H, dd, J=8.6 Hz,7.1 Hz), 7.75 (1H, d, J=1 Hz), 7.92 (1H, d, J=1 Hz)

Compound 2-2 mp: 223.6° C. ¹H-NMR δ (ppm; TMS): (CDCl₃) 7.1–7.2 (1H, m), 7.4–7.6 (2H, m), 7.76 (1H, d, J=1 Hz), 7.92 (1H, d, J=1 Hz)

Compound 2-3

¹H-NMR δ (ppm; TMS): (CDCl₃) 7.09 (2H, dd, J=7.5 Hz,8.2 Hz), 7.5–7.6 (1H, m), 7.74 (1H, d, J=1.7 Hz), 7.90 (1H, d, J=1.2 Hz)

Compound 2-4

¹H-NMR δ (ppm; TMS): (CDCl₃) 7.3–7.4 (2H, m), 7.5–7.6 (3H, m), 7.72 (1H, d, J=1.7 Hz), 7.89 (1H, d, J=1.7 Hz)

Compound 2-5

¹H-NMR δ (ppm; TMS): (CDCl₃) 7.32 (1H, dd, J=1.7 Hz,7.6 Hz), 7.4–7.5 (2H, m), 7.58 (1H, dd, J=1.3Hz,7.9 Hz), 7.73 (1H, d, J=1.5 Hz), 7.90 (1H, d, J=1.7 Hz)

Compound 2-6

$^1$H-NMR δ (ppm; TMS): (CDCl$_3$) 7.2–7.3 (1H, m), 7.3–7.4 (2H, m), 7.5–7.6 (1H, m), 7.73 (1H, d, J=1.4 Hz), 7.89 (1H, d, J=1.5 Hz)

Compound 2-7

$^1$H-NMR δ (ppm; TMS): (CDCl$_3$) 2.15 (3H, s), 7.12 (1H, dd, J=1.0 Hz, 7.6 Hz), 7.3–7.5 (2H, m), 7.72 (1H, d, J=1.7 Hz), 7.90 (1H, d, J=1.7 Hz)

Compound 2-8

$^1$H-NMR δ (ppm; TMS): (CDCl$_3$) 7.35 (1H, d, J=7.5 Hz), 7.6–7.8 (2H, m), 7.72 (1H, d, J=1.5 Hz), 7.87 (1H, d, J=7.7 Hz), 7.90 (1H, d, J=1.5 Hz)

Compound 2-12

$^1$H-NMR δ (ppm; TMS): (CDCl$_3$) 7.2–7.3 (2H, m), 7.3–7.4 (2H, m), 7.72 (1H, d, J=1.5 Hz), 7.89 (1H, d, J=1.7 Hz)

Compound 2-13

$^1$H-NMR δ (ppm; TMS): (CDCl3) 7.41–7.46 (1H, m), 7.50–7.53 (2H, m), 7.76 (1H, d, J=1.5 Hz), 7.92 (1H, d, J=1.4 Hz)

Compound 2-15

$^1$H-NMR δ (ppm; TMS): (CDCl$_3$) 6.9–7.1 (2H, m), 7.2–7.3 (1H, m), 7.73 (1H, d, J=1.5 Hz), 7.90 (1H, d, J=1.5 Hz)

Compound 2-16

$^1$H-NMR δ (ppm; TMS): (CDCl$_3$) 7.2–7.3 (2H, m), 7.52 (1H, dt, J=0.5 Hz, 1.9 Hz), 7.73 (1H, d, J=1 Hz), 7.91 (1H, d, J=1.2 Hz)

Compound 2-32 mp: 244.6° C. $^1$H-NMR δ (ppm; TMS): (CDCl$_3$) 2.43 (3H, s), 7.24 (1H, t, J=8 Hz), 7.4–7.6 (2H, m), 7.71 (1H, s), 7.88 (1H, s)

Compound 2-33

$^1$H-NMR δ (ppm; TMS): (CDCl$_3$) 1.27 (3H, t, J=7 Hz), 2.6–2.7 (2H, m), 7.19 (1H, dt, J=8 Hz, 1 Hz), 7.3–7.5 (2H, m), 7.69 (1H, d, J=1.6 Hz), 7.85 (1H, d, J=1.6 Hz)

Compound 3-1

$^1$H-NMR δ (ppm; TMS): (DMSO-d$_6$) 7.11 (2H, dd, J=7.7 Hz, 9.2 Hz), 7.39 (1H, d, J=2.5 Hz), 7.48 (1H, d, J=2.5 Hz), 11.9 (2H, brs)

Compound 3-2 (DBN salt)

$^1$H-NMR δ (ppm; TMS): (DMSO-d$_6$) 1.8–1.9 (2H, m), 1.9–2.0 (2H, m), 2.76 (2H, t, J=7.9 Hz), 3.27 (2H, t, J=5.7), 3.35 (2H, t, J=5.7 Hz), 3.58 (2H, t, J=7.2 Hz), 6.69 (1H, d, J=1.6 Hz), 7.0–7.1 (1H, m), 7.07 (1H, d, J=1.6 Hz), 7.1–7.2 (2H, m), 10.35 (2H, brs)

Compound 3-3

$^1$H-NMR δ (ppm; TMS): (DMSO-d$_6$) 7.05 (2H, t, J=8 Hz), 7.3–7.4 (1H, m), 7.40 (1H, d, J=2 Hz), 7.49 (1H, d, J=2 Hz), 11.94 (2H, brs)

Compound 3-4

$^1$H-NMR δ (ppm; TMS): (DMSO-d$_6$) 7.15 (1H, t, J=7 Hz), 7.29 (2H, t, J=7 Hz), 7.38 (1H, d, J=2.4 Hz), 7.46 (2H, d, J=7 Hz), 7.49 (1H, d, J=2.4 Hz), 11.74 (brs)

Compound 3-5

$^1$H-NMR δ (ppm; TMS): (DMSO-d$_6$) 7.2–7.3 (3H, m), 7.38 (1H, d, J=2.6 Hz), 7.4–7.5 (1H, m), 7.49 (1H, d, J=2.4 Hz), 12.5 (brs)

Compound 3-6

$^1$H-NMR δ (ppm; TMS): (DMSO-d$_6$) 7.1–7.2 (2H, m), 7.2–7.4 (2H, m), 7.39 (1H, d, J=2.7 Hz), 7.50 (1H, d, J=2.4 Hz), 12.6 (brs)

Compound 3-7

$^1$H-NMR δ (ppm; TMS): (DMSO-d$_6$) 2.11 (3H, s), 7.1–7.2 (4H, m), 7.3–7.4 (1H, m), 7.4–7.5 (1H, m), 12.5 (brs)

Compound 3-8

$^1$H-NMR δ (ppm; TMS): (DMSO-d$_6$) 7.30 (1H, d, J=7.7 Hz), 7.37 (1H, d, J=2.4 Hz), 7.4–7.6 (2H, m), 7.64 (1H, t, J=7.5 Hz), 7.73 (1H, d, J=8.0 Hz)

Compound 3-12

$^1$H-NMR δ (ppm; TMS): (DMSO-d$_6$) 7.11 (2H, t, J=8.8 Hz), 7.38 (1H, d, J=2.4 Hz), 7.4–7.5 (3H, m), 11.4 (brs), 12.3 (brs)

Compound 3-13 (DBU salt)

$^1$H-NMR δ (ppm; TMS): (DMSO-d6) 1.59–1.67 (6H, m), 1.87–1.94 (2H, m), 2.49–2.51 (2H, m), 3.23 (2H, t, J=5.6 Hz), 3.46 (2H, t, J=5.7 Hz), 3.52–3.56 (2H, m), 6.69 (1H, d, J=1.5 Hz), 7.09 (1H, d, J=1.5 Hz), 7.15–7.20 (1H, m), 7.35 (2H, d, J=8.0 Hz), 9.5 (brs), 10.3 (brs)

Compound 3-15

$^1$H-NMR δ (ppm; TMS): (DMSO-d$_6$) 7.04 (1H, dt, J=2.4 Hz,8.5 Hz), 7.16 (1H, dt, J=2.6 Hz,9.7 Hz), 7.34 (1H, dt, J=7.0 Hz,8.5 Hz), 7.40 (1H, d, J=2.4Hz,) 7.49 (1H, d, J=2.4 Hz)

Compound 3-16

$^1$H-NMR δ (ppm; TMS) (DMSO-d$_6$) 7.3–7.4 (2H, m), 7.52 (1H, d, J=2.6 Hz), 7.59 (2H, dt, J=1.7 Hz)

Compound 4-5

$^1$H-NMR δ (ppm; TMS): (DMSO-d$_6$) 2.03 (3H, s), 7.2–7.3 (1H, m), 7.4–7.5 (2H, m), 7.51 (1H, d, J=2.4 Hz), 7.59 (1H, d, J=2.4 Hz), 12.90 (1H, brs)

Compound 4-6

$^1$H-NMR δ (ppm; TMS): (CDCl$_3$) 1.29 (3H, t, J=7 Hz), 2.5–2.6 (2H, m), 7.0–7.2 (2H, m), 7.3–7.4 (2H, m), 7.67 (1H, d, J=2.3 Hz)

Next, the formulation examples are given below. Part represents part by weight and the present compounds are referred to the numbers described in the above table.

FORMULATION EXAMPLE 1

Fifty parts of each of Compounds 1–637, 3 parts of calcium ligninsulfonate, 2 parts of magnesium laurylsulfate and 45 parts of synthetic hydrated silicon dioxide are well pulverized and mixed to give each of wettable powders.

FORMULATION EXAMPLE 2

Twenty parts of each of Compounds 1–637 and 1.5 parts of sorbitan trioleate are mixed with 28.5 parts of aqueous solution containing 2% by weight of polyvinyl alcohol, and finely pulverized with wet pulverizing method. Forty parts of aqueous solution containing 0.05% by weight of xanthan gum and 0.1% by weight of aluminum magnesium silicate are added thereto, and further 10 parts of propylene glycol were added and stirred to give each of flowable formulations.

FORMULATION EXAMPLE 3

Two parts of each of Compounds 1–637, 88 parts of kaolin clay and 10 parts of talc are well pulverized and mixed to give each of dusts.

FORMULATION EXAMPLE 4

Five parts of each of Compounds 1–637, 14 parts of polyoxyethylene styryl phenyl ether, 6 parts of calcium dodecylbenzenesulfonate and 75 parts of xylene are well mixed to give each of emulsifiable concentrate.

FORMULATION EXAMPLE 5

Two parts of each of Compounds 1–637, one part of synthetic hydrated silicon dioxide, 2 parts of calcium lign-insulfonate, 30 parts of bentonite and 65 parts of kaolin clay are well pulverized and mixed. Water is added thereto and well kneaded to give each of granules.

FORMULATION EXAMPLE 6

Ten parts of each of Compounds 1–637, 35 parts of white carbon containing 50% by weight of polyoxyethylene alkyl ether sulfate and 55 parts of water are mixed, and finely pulverized with wet pulverizing method to give each of flowable formulations.

The following test examples show that the present compounds are useful for controlling plant diseases. The present compounds are referred to the numbers described in the above table.

The control effect of the present compound was evaluated by visually observing the area of a lesion on a plant under test in investigation and comparing the area of a lesion in a non-treatment group and the area of a lesion in a group treated with the present compound.

TEST EXAMPLE 1

Preventive Efficacy Against *Botrytis cinerea* on Cucumber

Sand loam was compacted in plastic pots, cucumbers (Ochiai Aonagafushinari) were seeded and grown in a greenhouse for 10 days. Then, Compounds 7, 8, 9, 21, 29, 49, 50, 52, 53, 54, 55, 63, 65, 71, 72, 73, 81, 83, 85, 89, 161, 180, 187, 226, 228, 233, 251, 255, 259, 267, 283, 285, 287, 295, 428, 449, 521 and 535 were formulated into flowable formulations according to Formulation Example 6, then, diluted with water to provide prescribed concentration (500 ppm), and these were sprayed over the foliage so as to give sufficient adhesion on the surface of cucumber cotyledons. After spraying, the plants were air-dried, and PDA medium containing spores of *Botrytis cinerea* were attached on cucumber cotyledons. After the inoculation, the cucumbers were placed in a humid condition at 12° C. for 4 days, and the control effect was examined. The results showed that areas of lesions on the plants of the groups treated with the present compounds were not greater than 30% of areas of lesions on those of the untreated groups.

TEST EXAMPLE 2

Preventive Efficacy Against *Sphaerotheca fuliginea* on Cucumber

Sand loam was compacted in plastic pots, cucumbers (*Ochiai Aonagafushinari*) were seeded and grown in a greenhouse for 12 days. Then, Compounds 1, 4, 7, 8, 20, 52, 55, 76, 81, 83, 161 and 449 were formulated into flowable formulations according to Formulation Example 6, then, diluted with water to provide prescribed concentration (500 ppm), and these were sprayed over the foliage so as to give sufficient adhesion on the surface of cucumber leaves. After spraying, the plants were air-dried, and inoculated with spores of *Sphaerotheca fuliginea*. After the inoculation, the cucumbers were placed at 23° C. for 12 days, and the control effect was examined. The results showed that areas of lesions on the plants of the groups treated with the present compounds were not greater than 30% of areas of lesions on those of the untreated groups.

For the reference, the compound of Example 12 on page 12 of JP2001-19693A (hereinafter referred to as Reference Compound A) and Compound 182 of the present invention were tested.

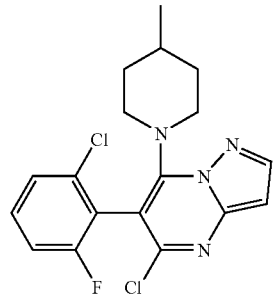

Reference Compound A

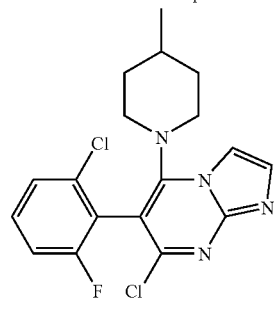

Compound 182

TEST EXAMPLE 3

Preventive Efficacy Against *Botrytis cinerea* on Cucumber

Sand loam was compacted in plastic pots, cucumbers (*Ochiai Aonagafushinari*) were seeded and grown in a greenhouse for 10 days. Then, each of Reference Compound A and Compound 182 was formulated into a flowable formulation according to Formulation Example 6, then, diluted with water to provide prescribed concentration (500 ppm), and sprayed over the foliage so as to give sufficient adhesion on the surface of cucumber cotyledons. After spraying, the plants were air-dried, and PDA medium containing spores of *Botrytis cinerea* were attached on cucumber cotyledons. After the inoculation, the cucumbers were placed in a humid condition at 12° C. for 4 days, and the control effect was examined. As a result, areas of lesions on the plant treated with Reference Compound A were in the range of 75% to 100% on those of the untreated groups, on the other hand, areas of lesions on the plant treated with Compound 182 was not greater than 1% of areas of lesions on those of the untreated groups.

TEST EXAMPLE 4

Preventive Efficacy Against *Sphaerotheca fuliginea* on Cucumber

Sand loam was compacted in plastic pots, cucumbers (*Ochiai Aonagafushinari*) were seeded and grown in a greenhouse for 12 days. Then, each of Reference Compound A and Compound 182 was formulated into flowable formulations according to Formulation Example 6, then, diluted with water to provide prescribed concentration (500 ppm), and sprayed over the foliage so as to give sufficient adhesion on the surface of cucumber leaves. After spraying, the plants were air-dried, and inoculated with spores of *Sphaerotheca fuliginea*. After the inoculation, the cucumbers were placed at 23° C. for 12 days, and the control effect was examined. As a result, areas of lesions on the plant treated with Reference Compound A were in the range of 75% to 100% on those of the untreated groups, on the other hand, areas of lesions on the plant treated with Compound 182 was not greater than 1% of infested areas on those of the untreated groups.

INDUSTRIAL APPLICABILITY

It can be controlled plant diseases by using the present compound.

The invention claimed is:

1. An imidazo[1,2-a]pyrimidine given by the following formula [I]:

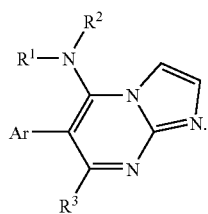

[wherein $R^1$ represents a hydrogen atom; C1–C6 alkyl group optionally substituted by one or more selected from the group consisting of C1–C4 alkoxy group, C2–C8 dialkylamino group, C1–C4 alkylthio group, C2–C5 alkoxycarbonyl group, cyano group and halogen atoms; C3–C6 alkenyl group optionally substituted by a halogen atom or atoms; C3–C6 alkynyl group optionally substituted by a halogen atom or atoms; C3–C8 cycloalkyl group optionally substituted by one or more selected from the group consisting of C1–C4 alkyl group and halogen atoms; phenyl group or phenyl C1–C2 alkyl group optionally substituted by one or more selected from the group consisting of C1–C4 alkyl group, C1–C4 alkoxy group, C1–C4 alkylthio group, C1–C3 haloalkyl group, C1–C3 haloalkoxy group, halogen atoms, nitro group, cyano group and C2–C5 alkoxycarbonyl group on the benzene ring; 5 or 6 membered heterocyclic group optionally substituted by one or more selected from the group consisting of C1–C4 alkyl group, C1–C4 alkoxy group, C1–C4 alkylthio group, C1–C3 haloalkyl group, halogen atoms, nitro group, cyano group and C2–C5 alkoxycarbonyl group; $R^2$ represents a hydrogen atom; C1–C6 alkyl group optionally substituted by one or more selected from the group consisting of C1–C4 alkoxy group, C2–C8 dialkylamino group, C1–C4 alkylthio group, C2–C5 alkoxycarbonyl group, cyano group and halogen atoms; C3–C6 alkenyl group optionally substituted by a halogen atom or atoms; C3–C6 alkynyl group optionally substituted by a halogen atom or atoms; C3–C8 cycloalkyl group optionally substituted by one or more selected from the group consisting of C1–C4 alkyl group and halogen atoms; phenyl group or phenyl C1–C2 alkyl group optionally substituted by one or more selected from the group consisting of C1–C4 alkyl group, C1–C4 alkoxy group, C1–C4 alkylthio group, C1–C3 haloalkyl group, C1–C3 haloalkoxy group, halogen atoms, nitro group, cyano group and C2–C5 alkoxycarbonyl group on the benzene ring; 5 or 6 membered heterocyclic group optionally substituted by one or more selected from the group consisting of C1–C4 alkyl group, C1–C4 alkoxy group, C1–C4 alkylthio group, C1–C3 haloalkyl group, halogen atoms, nitro group, cyano group and C2–C5 alkoxycarbonyl group; amino group optionally substituted by one or more selected from the group consisting of C1–C6 alkyl group, phenly group and benzyl group (said phenly group and benzyl group may be substituted by one or more selected from the group consisting of C1–C4 alkyl group, C1–C3 haloalkyl group and halogen atoms on the benzene ring); C1–C4 alkoxy group; phenoxy group; benzyloxy group; or $R^1$ and $R^2$ together with the nitrogen atom bonded with $R^1$ and $R^2$ represent 3–8 membered heterocyclic group (said heterocyclic group may be substituted by C1–C4 alkylene group or C2–C4 alkenylene group to represent polycyclic heterocyclic group, and substituted by one or more selected from the group consisting of C1–C4 alkyl group, C1–C4 alkoxy group, C1–C4 alkylthio group, C1–C3 haloalkyl group, C1–C4 acyl group, halogen atoms, hydroxy group, nitro group, cyano group and C2–C5 alkoxycarbonyl group); $R^3$ represents a halogen atom or C1–C4 alkyl group; Ar represents a phenyl group optionally substituted by one or more selected from the group consisting of halogen atoms, C1–C4 alkyl group, C1–C4 alkoxy group and C1–C3 haloalkyl group].

2. The imidazo[1,2-a]pyrimidine according to claim 1, wherein $R^1$ is a hydrogen atom; C1–C6 alkyl group optionally substituted by one or more selected from the group consisting of C1–C4 alkoxy group, C2–C8 dialkylamino group, C1–C4 alkylthio group, C2–C5 alkoxycarbonyl group, cyano group and halogen atoms; C3–C6 alkenyl group optionally substituted by a halogen atom or atoms; C3–C6 alkynyl group optionally substituted by a halogen atom or atoms; C3–C8 cycloalkyl group optionally substituted by one or more selected from the group consisting of C1–C4 alkyl group and halogen atoms; phenyl group or phenyl C1–C2 alkyl group optionally substituted by one or more selected from the group consisting of C1–C4 alkyl group, C1–C4 alkoxy group, C1–C4 alkylthio group, C1–C3 haloalkyl group, C1–C3 haloalkoxy group, halogen atoms, nitro group, cyano group and C2–C5 alkoxycarbonyl group on the benzene ring; 5 or 6 membered heterocyclic group optionally substituted by one or more selected from the group consisting of C1–C4 alkyl group, C1–C4 alkoxy group, C1–C4 alkylthio group, C1–C3 haloalkyl group, halogen atoms, nitro group, cyano group and C2–C5 alkoxycarbonyl group; $R^2$ is a hydrogen atom; C1–C6 alkyl group optionally substituted by one or more selected from the group consisting of C1–C4 alkoxy group, C2–C8 dialkylamino group, C1–C4 alkylthio group, C2–C5 alkoxycarbonyl group, cyano group and halogen atoms; C3–C6 alkenyl group optionally substituted by a halogen atom or atoms; C3–C6 alkynyl group optionally substituted by a halogen atom or atoms; C3–C8 cycloalkyl group optionally substituted by one or more selected from the group consisting of C1–C4 alkyl group and halogen atoms; phenyl group or phenyl C1–C2 alkyl group optionally substituted by one or more selected from the group consisting of C1–C4 alkyl group, C1–C4 alkoxy group, C1–C4 alkylthio group, C1–C3 haloalkyl group, C1–C3 haloalkoxy group, halogen atoms, nitro group, cyano group and C2–C5 alkoxycarbonyl group on the benzene ring; 5 or 6 membered heterocyclic group optionally substituted by one or more selected from the group consisting of C1–C4 alkyl group, C1–C4 alkoxy group, C1–C4 alkylthio group, C1–C3 haloalkyl group, halogen atoms, nitro group, cyano group and C2–C5 alkoxycarbonyl group; amino group optionally substituted by one or more selected from the group consisting of C1–C6 alkyl group, pheny group and benzyl group (said pheny group and benzyl group may be substituted by one or more selected from the group consisting of C1–C4 alkyl group, C1–C3 haloalkyl group and halogen atoms on the benzene ring); C1–C4 alkoxy group; phenoxy group; benzyloxy group; or $R^1$ and $R^2$ together with the nitrogen atom bonded with $R^1$ and $R^2$ are 3–8 membered heterocyclic group (said heterocyclic group may be substituted by one or more selected from the group consisting of C1–C4 alkyl group, C1–C4 alkoxy group, C1–C4 alkylthio group, C1–C3 haloalkyl group, C1–C4 acyl group, halogen atoms, hydroxy group, nitro group, cyano group and C2–C5 alkoxycarbonyl group) in the formula [I].

3. The imidazo[1,2-a]pyrimidine according to claim 1, wherein $R^1$ and $R^2$ are independently a hydrogen atom; C1–C6 alkyl group optionally substituted by one or more selected from the group consisting of C1–C4 alkoxy group, C2–C8 dialkylamino group, C1–C4 alkylthio group, C2–C5 alkoxycarbonyl group, cyano group and halogen atoms; C3–C6 alkenyl group optionally substituted by a halogen atom or atoms; C3–C6 alkynyl group optionally substituted by a halogen atom or atoms; C3–C8 cycloalkyl group optionally substituted by one or more selected from the group consisting of C1–C4 alkyl group and halogen atoms; phenyl group or phenyl C1–C2 alkyl group optionally substituted by one or more selected from the group consisting of C1–C4 alkyl group, C1–C4 alkoxy group, C1–C4 alkylthio group, C1–C3 haloalkyl group, C1–C3 haloalkoxy group, halogen atoms, nitro group, cyano group and C2–C5 alkoxycarbonyl group on the benzene ring; 5 or 6 membered heterocyclic group optionally substituted by one or more selected from the group consisting of C1–C4 alkyl group, C1–C4 alkoxy group, C1–C4 alkylthio group, C1–C3 haloalkyl group, halogen atoms, nitro group, cyano group and C2–C5 alkoxycarbonyl group; or $R^1$ and $R^2$ together with the nitrogen atom bonded with $R^1$ and $R^2$ are 3–8 membered heterocyclic group (said heterocyclic group may be substituted by C1–C4 alkylene group or C2–C4 alkenylene group to be polycyclic heterocyclic group, and substituted by one or more selected from the group consisting of C1–C4 alkyl group, C1–C4 alkoxy group, C1–C4 alkylthio group, C1–C3 haloalkyl group, C1–C4 acyl group, halogen atoms, hydroxy group, nitro group, cyano group and C2–C5 alkoxycarbonyl group) in the formula [I].

4. The imidazo[1,2-a]pyrimidine according to claim 1, wherein $R^1$ and $R^2$ are independently a hydrogen atom; C1–C6 alkyl group optionally substituted by one or more selected from the group consisting of C1–C4 alkoxy group, C2–C8 dialkylamino group, C1–C4 alkylthio group, C2–C5 alkoxycarbonyl group, cyano group and halogen atoms; C3–C6 alkenyl group optionally substituted by a halogen atom or atoms; C3–C6 alkynyl group optionally substituted by a halogen atom or atoms; C3–C8 cycloalkyl group optionally substituted by one or more selected from the group consisting of C1–C4 alkyl group and halogen atoms; phenyl group or phenyl C1–C2 alkyl group optionally substituted by one or more selected from the group consisting of C1–C4 alkyl group, C1–C4 alkoxy group, C1–C4 alkylthio group, C1–C3 haloalkyl group, C1–C3 haloalkoxy group, halogen atoms, nitro group, cyano group and C2–C5 alkoxycarbonyl group on the benzene ring; 5 or 6 membered heterocyclic group optionally substituted by one or more selected from the group consisting of C1–C4 alkyl group, C1–C4 alkoxy group, C1–C4 alkylthio group, C1–C3 haloalkyl group, halogen atoms, nitro group, cyano group and C2–C5 alkoxycarbonyl group; or $R^1$ and $R^2$ together with the nitrogen atom bonded with $R^1$ and $R^2$ are 3–8 membered heterocyclic group (said heterocyclic group may be substituted by one or more selected from the group consisting of C1–C4 alkyl group, C1–C4 alkoxy group, C1–C4 alkylthio group, C1–C3 haloalkyl group, C1–C4 acyl group, halogen atoms, hydroxy group, nitro group, cyano group and C2–C5 alkoxycarbonyl group) in the formula [I].

5. The imidazo[1,2-a]pyrimidine according to claim 1, wherein $R^1$ and $R^2$ are independently a hydrogen atom; C1–C6 alkyl group optionally substituted by one or more selected from the group consisting of C1–C4 alkoxy group, C2–C8 dialkylamino group, C1–C4 alkylthio group, C2–C5 alkoxycarbonyl group, cyano group and halogen atoms; C3–C6 alkenyl group optionally substituted by a halogen atom or atoms; C3–C6 alkynyl group optionally substituted by a halogen atom or atoms; C3–C8 cycloalkyl group optionally substituted by one or more selected from the group consisting of C1–C4 alkyl group and halogen atoms; or $R^1$ and $R^2$ together with the nitrogen atom bonded with $R^1$ and $R^2$ are 3–8 membered heterocyclic group (said heterocyclic group may be substituted by C1–C4 alkylene group or C2–C4 alkenylene group to be polycyclic heterocyclic group, and substituted by one or more selected from the group consisting of C1–C4 alkyl group, C1–C4 alkoxy group, C1–C4 alkylthio group, C1–C3 haloalkyl group, C1–C4 acyl group, halogen atoms, hydroxy group, nitro group, cyano group and C2–C5 alkoxycarbonyl group) in the formula [I].

6. The imidazo[1,2-a]pyrimidine according to claim 1, wherein $R^1$ and $R^2$ are independently a hydrogen atom; C1–C6 alkyl group optionally substituted by one or more selected from the group consisting of C1–C4 alkoxy group, C2–C8 dialkylamino group, C1–C4 alkylthio group, C2–C5 alkoxycarbonyl group, cyano group and halogen atoms; C3–C6 alkenyl group optionally substituted by a halogen atom or atoms; C3–C6 alkynyl group optionally substituted by a halogen atom or atoms; C3–C8 cycloalkyl group optionally substituted by one or more selected from the group consisting of C1–C4 alkyl group and halogen atoms; or $R^1$ and $R^2$ together with the nitrogen atom bonded with $R^1$ and $R^2$ are 3–8 membered heterocyclic group (said heterocyclic group may be substituted by one or more selected from the group consisting of C1–C4 alkyl group, C1–C4 alkoxy group, C1–C4 alkylthio group, C1–C3 haloalkyl group, C1–C4 acyl group, halogen atoms, hydroxy group, nitro group, cyano group and C2–C5 alkoxycarbonyl group) in the formula [I].

7. The imidazo[1,2-a]pyrimidine according to claim 1, wherein $R^1$ and $R^2$ are independently a C1–C6 alkyl group optionally substituted by one or more selected from the group consisting of C1–C4 alkoxy group, C2–C8 dialkylamino group, C1–C4 alkylthio group, C2–C5 alkoxycarbonyl group, cyano group and halogen atoms; C3–C6 alkenyl group optionally substituted by a halogen atom or atoms; C3–C6 alkynyl group optionally substituted by a halogen atom or atoms; C3–C8 cycloalkyl group optionally substituted by one or more selected from the group consisting of C1–C4 alkyl group and halogen atoms; or $R^1$ and $R^2$ together with the nitrogen atom bonded with $R^1$ and $R^2$ are 3–8 membered heterocyclic group (said heterocyclic group may be substituted by one or more selected from the group consisting of C1–C4 alkyl group, C1–C4 alkoxy group, C1–C4 alkylthio group, C1–C3 haloalkyl group, C1–C4 acyl group, halogen atoms, hydroxy group, nitro group, cyano group and C2–C5 alkoxycarbonyl group) in the formula [I].

8. The imidazo[1,2-a]pyrimidine according to claim 1, wherein $R^1$ and $R^2$ together with the nitrogen atom bonded with $R^1$ and $R^2$ are 3–8 membered heterocyclic group (said heterocyclic group may be substituted by C1–C4 alkylene group or C2–C4 alkenylene group to be polycyclic heterocyclic group, and substituted by one or more selected from the group consisting of C1–C4 alkyl group, C1–C4 alkoxy group, C1–C4 alkylthio group, C1–C3 haloalkyl group, C1–C4 acyl group, halogen atoms, hydroxy group, nitro group, cyano group and C2–C5 alkoxycarbonyl group) in the formula [I].

9. The imidazo[1,2-a]pyrimidine according to claim 8, wherein the 3–8 membered heterocyclic group represented by $R^1$ and $R^2$ together with the nitrogen atom bonded with $R^1$ and $R^2$ in the formula [I] is pyrrolidin-1-yl group, piperidin-1-yl group, morpholin-4-yl group, thiomorpholin-4-yl group or hexamethylene-1-yl group.

10. The imidazo[1,2-a]pyrimidine according to claim 1, wherein the Ar in the formula [I] is a phenyl group substituted by a halogen atom or atoms at one or more of 2-, 4- and 6-position.

11. The imidazo[1,2-a]pyrimidine according to claim 1, wherein the Ar in the formula [I] is a phenyl group substituted by fluorine atoms or chlorine atoms at two or more of 2-, 4- or 6-position and unsubstituted at 3- and 5-position.

12. The imidazo[1,2-a]pyrimidine according to claim 1, wherein the Ar in the formula [I] is a 2,6-difluorophenyl group, 2,4,6-trifluorophenyl group, 4-chloro-2,6-difluorophenyl group, 2-chloro-6-fluorophenyl group, 2-chloro-4,6-difluorophenyl group or 2,4-dichloro-6-fluorophenyl group.

13. The imidazo[1,2-a]pyrimidine according to claim 1, wherein $R^3$ is a chlorine atom or methyl group; and Ar is a 2,6-difluorophenyl group, 2,4,6-trifluorophenyl group, 4-chloro-2,6-difluorophenyl group, 2-chloro-6-fluorophenyl group, 2-chloro-4,6-difluorophenyl group or 2,4-dichloro-6-fluorophenyl group in the formula [I].

14. A fungicidal composition comprising the imidazo[1,2-a]pyrimidine described in claim 1 as an active ingredient.

15. A method for controlling fungal plant diseases which comprise applying the imidazo[1,2-a]pyrimidine described in claim 1 to a plant or soil for cultivating the plant.

16. An imidazo[1,2-a]pyrimidine given by the following formula [II]:

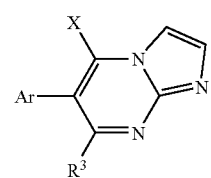

[wherein X represents a halogen atom; $R^3$ represents a halogen atom or C1–C4 alkyl group; and Ar represents a phenyl group optionally substituted by a halogen atoms, or atoms at one or more of 2-, 4- or 6-position.

17. The imidazo[1,2-a]pyrimidine according to claim 16, wherein the Ar in the formula [II] is a 2,6-difluorophenyl group, 2,4,6-trifluorophenyl group, 4-chloro-2,6-difluorophenyl group, 2-chloro-6-fluorophenyl group, 2-chloro-4,6-difluorophenyl group or 2,4-dichloro-6-fluorophenyl group.

18. An imidazo[1,2-a]pyrimidine given by the following formula [III]:

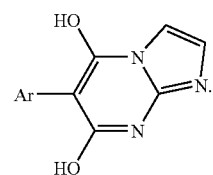

[wherein Ar represents a phenyl group optionally substituted by one or more selected from the group consisting of halogen atoms, C1–C4 alkyl group, C1–C4 alkoxy group and C1–C3 haloalkyl group].

19. The imidazo[1,2-a]pyrimidine according to claim 18, wherein the Ar in the formula [III] is a phenyl group substituted by a halogen atom or atoms at one or more of 2-, 4- or 6-position.

20. The imidazo[1,2-a]pyrimidine according to claim 18, wherein the Ar in the formula [III] is a 2,6-difluorophenyl group, 2,4,6-trifluorophenyl group, 4-chloro-2,6-difluorophenyl group, 2-chloro-6-fluorophenyl group, 2-chloro-4,6-difluorophenyl group or 2,4-dichloro-6-fluorophenyl group.

21. An imidazo[1,2-a]pyrimidine given by the following formula [IV]:

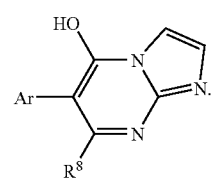

[wherein $R^8$ represents a C1–C4 alkyl group; and Ar represents a phenyl group optionally substituted by one or more selected from the group consisting of halogen atoms, C1–C4 alkyl group, C1–C4 alkoxy group and C1–C3 haloalkyl group].

22. The imidazo[1,2-a]pyrimidine according to claim 21, wherein the Ar in the formula [IV] is a phenyl group substituted by a halogen atom or atoms at one or more of 2-, 4- or 6-position.

23. The imidazo[1,2-a]pyrimidine according to claim 21, wherein the Ar in the formula [IV] is a 2,6-difluorophenyl group, 2,4,6-trifluorophenyl group, 4-chloro-2,6-difluorophenyl group, 2-chloro-6-fluorophenyl group, 2-chloro-4,6-difluorophenyl group or 2,4-dichloro-6-fluorophenyl group.

* * * * *